United States Patent
Ma et al.

(10) Patent No.: US 11,419,952 B2
(45) Date of Patent: Aug. 23, 2022

(54) FUNCTIONALIZED NANOPARTICLES AND METHODS OF MAKING AND USING SAME

(71) Applicant: Cornell University, Ithaca, NY (US)

(72) Inventors: Kai Ma, Belle Mead, NJ (US); Ulrich B. Wiesner, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 16/614,975

(22) PCT Filed: May 21, 2018

(86) PCT No.: PCT/US2018/033755
§ 371 (c)(1),
(2) Date: Nov. 19, 2019

(87) PCT Pub. No.: WO2018/213851
PCT Pub. Date: Nov. 22, 2018

(65) Prior Publication Data
US 2020/0179538 A1    Jun. 11, 2020

Related U.S. Application Data

(60) Provisional application No. 62/508,703, filed on May 19, 2017.

(51) Int. Cl.
| | |
|---|---|
| *A61K 49/00* | (2006.01) |
| *A61K 47/69* | (2017.01) |
| *A61K 9/51* | (2006.01) |
| *A61K 47/02* | (2006.01) |
| *B82Y 5/00* | (2011.01) |

(52) U.S. Cl.
CPC ........ *A61K 49/0093* (2013.01); *A61K 9/5146* (2013.01); *A61K 47/02* (2013.01); *A61K 47/6923* (2017.08); *A61K 49/0032* (2013.01); *A61K 49/0043* (2013.01); *A61K 49/0054* (2013.01); *B82Y 5/00* (2013.01)

(58) Field of Classification Search
CPC ... A61K 49/00; A61K 47/6923; A61K 9/5146
See application file for complete search history.

(56) References Cited

U.S. PATENT DOCUMENTS

| | | | |
|---|---|---|---|
| 2008/0063868 A1 | 3/2008 | Chung et al. | |
| 2013/0039848 A1* | 2/2013 | Bradbury | A61K 51/1255 424/9.4 |
| 2015/0366995 A1* | 12/2015 | Wiesner | A61K 47/6935 424/489 |
| 2016/0018404 A1* | 1/2016 | Iyer | G01N 33/552 435/7.1 |
| 2016/0287717 A1 | 10/2016 | Brinker et al. | |
| 2018/0050115 A1 | 2/2018 | Mou et al. | |
| 2018/0099050 A1 | 4/2018 | Trogler et al. | |
| 2020/0101180 A1 | 4/2020 | Bradbury et al. | |

FOREIGN PATENT DOCUMENTS

| | | |
|---|---|---|
| CN | 105056233 B | 3/2018 |
| EP | 2449379 B1 | 5/2017 |
| JP | 2017031014 A | 2/2017 |
| WO | 2016/149378 A1 | 9/2016 |
| WO | 2016/179260 A1 | 11/2016 |
| WO | 2017/136641 A1 | 8/2017 |
| WO | 2018217528 A1 | 11/2018 |

OTHER PUBLICATIONS

Ma et al., Modular and Orthogonal Post-PEGylation Surface Modifications by Insertion Enabling Penta-functional Ultrasmall Organic-Silica Hybrid Nanoparticles, Chemistry of Materials, Jul. 23, 2017, vol. 29, No. 16, pp. 6840-6855.
Chen et al., Melanocortin-1 Receptor-Targeting Ultrasmall Silica Nanoparticles for Dual-Modality Human Melanoma Imaging, Feb. 7, 2018, vol. 5, No. 10, pp. 4379-4393.
Ma et al., Control of Ultrasmall Sub-10 nm Ligand-Functionalized Fluorescent Core-Shell Silica Nanoparticle Growth in Water, Chemistry of Materials, May 13, 2015, vol. 27, pp. 4119-4133.
Ma et al., Elucidating the Mechanism of Silica Nanoparticle PEGylation Processes Using Fluorescence Correlation Spectroscopies, Chemistry of Materials, Feb. 8, 2016, vol. 28, pp. 1537-1545.
Sun et al., Water-Based Synthesis of Ultrasmall PEGylated Gold-Silica Core-Shell Nanoparticles with Long-Term Stability, Chemistry of Materials, Sep. 5, 2014, vol. 26, pp. 5201-5207.

(Continued)

*Primary Examiner* — Michael G. Hartley
*Assistant Examiner* — Jagadishwar R Samala
(74) *Attorney, Agent, or Firm* — Paul J. Roman, Jr.; Johnson, Marcou, Isaacs & Nix, LLC

(57) ABSTRACT

Described is a versatile surface modification approach to, for example, modularly and orthogonally functionalize nanoparticles (NPs) such as, for example, PEGylated nanoparticles, ith various types of different functional ligands (functional groups) on the NP surface. It enables the synthesis of, for example, penta-functional PEGylated nanoparticles integrating a variety of properties into a single NP, e.g., fluorescence detection, specific cell targeting, radioisotope chelating/labeling, ratiometric pH sensing, and drug delivery, while the overall NP size remains, for example, below 10 nm.

19 Claims, 32 Drawing Sheets

(56) References Cited

OTHER PUBLICATIONS

Ma et al., Ultrasmall Wub-10 nm Near-Infrared Fluorescent Mesoporous Silica Manoparticles, Journal of the American Chemical Society, Jul. 25, 2012, vol. 134, pp. 13180-13183.

Chen et al., Cancer-Targeting Ultrasmall Silica Nanoparticles for Clinical Translation: Physicochemical Structure and Biological Property Correlations, Sep. 15, 2017, vol. 29, pp. 8766-8779.

Schladt, T. D. et al., Multifunctional superparamagnetic MnO@SiO2 core/shell nanoparticles and their application for optical and magnetic resonance imaging, Journal of Materials Chemistry, 2012, vol. 22, pp. 9253-9262.

\* cited by examiner

FUNCTIONALIZED NANOPARTICLES AND METHODS OF MAKING AND USING SAME

CROSS REFERENCE TO RELATED APPLICATIONS

This application claims priority to U.S. Provisional Application No. 62/508,703, filed on May 19, 2017, the disclosure of which is hereby incorporated by reference.

STATEMENT REGARDING FEDERALLY SPONSORED RESEARCH

This invention was made with government support under Grant Number CA199081 awarded by the National Institutes of Health. The government has certain rights in the invention.

FIELD OF THE DISCLOSURE

The disclosure generally relates to surface functionalized nanoparticles and methods of making and using same. More particularly, the disclosure relates to surface functionalized silica and aluminosilicate nanoparticles.

BACKGROUND OF THE DISCLOSURE

While, silica nanoparticles (SNPs) have attracted interest for potential therapeutic/diagnostic applications due to their large surface-area, inertness and high bio-compatibility. However, most SNPs are >10 nm in size.

Particles>12 nm are not effectively cleared from the body in vivo and unfavorably distribute to the liver and other organs/tissues, potentially exposing these tissues to toxic elements (especially if these >10 nm SNPs are modified with drugs and/or radioactivity). Particles about 8 nm in diameter reside in the body for about a day, 10-11 nm about 3-5 days, but if greater than 12 nm do not clear or clear very slowly.

Currently, ultrasmall inorganic nanoparticles are of rapidly increasing interest as nanomedicines for cancer theranostics. Some organic based nanomedicines are already more competitive than conventional chemotherapy drugs due to multifunctionality and multivalency effects. Inorganic nanoparticles further diversify the building elements of nanomedicines and may provide advantages associated with their intrinsic physical properties and lower manufacturing costs. Safe translation of nanoparticles from the laboratory to the clinic requires overcoming a number of substantial scientific and regulatory hurdles. The most important criteria are favorable biodistribution and its time evolution (pharmacokinetics, PK) profiles. The size threshold for renal clearance is below 10 nm. Until today only a small number of inorganic nanoparticle platforms have been synthesized with sizes below 10 nm allowing for efficient renal clearance. Among those only <10 nm sized polyethylene glycol coated (PEGylated) fluorescent core-shell silica nanoparticles (SNPs) referred to as Cornell dots or simply C dots have been approved by the U.S. Food and Drug Administration (FDA) as an investigational new drug (IND) for first in-human clinical trials. Although the first clinical trial results with melanoma patients are encouraging, several synthesis challenges remain for such sub 10 nm sized fluorescent organic-inorganic hybrid SNPs.

First, all previous C dot-type SNP synthesis efforts followed a modified Stober process in which alcohol was used as solvent. For materials for use in biological or clinical applications, however, water as a reaction medium would be preferred. It would greatly simplify synthesis and cleaning protocols leading to less volatile waste, thereby rendering particle production substantially faster and more cost effective. Furthermore, although the Stober process is widely used to produce SNPs with diameters from tens of nm to microns, particle sizes of 10 nm and below are at the limit of size control of this synthesis process due to reaction kinetics limitations in alcohol.

Second, covalently covering silica particle surfaces with PEG can be tricky as the loss of surface charge during PEGylation may result in particle aggregation or at least broadening of the particle size distribution. This effect is more pronounced for ultrasmall particles due to the increase of particle surface energy, and thus limits the particle monodispersity and size control ability.

Third, as a result of the negative surface charge of silica above its isoelectric point at pH 2-3, covalent encapsulation efficiencies for silane-conjugated organic fluorescent dyes with negatively charged groups into SNPs are low as a result of electrostatic repulsion between silica and fluorophore. This is particularly true for near-infrared (NIR) emitting dyes most desirable for imaging applications in living tissue. NIR dyes have large delocalized $\pi$-electron systems and to be soluble in water typically require multiple negatively charged functional groups (e.g. sulfates) on their periphery. Low incorporation efficiencies are a problem for these dyes as their typical costs are of order $200-$300 per mg and re-use of typically employed silane-dye conjugates after the initial synthesis is problematic.

Finally, no inorganic elemental compositions other than silica have been reported for <10 nm sized fluorescent SNPs and core-shell SNPs. In particular, compositions are of interest leading to higher rigidity of the organic dye environments as increases in rigidity have directly been correlated with increases in per dye fluorescence yield as a result of decreases in non-radiative rates. Here silica compositions derived from aluminum alkoxides as additives are particularly interesting as they are known hardening components in alkoxysilane derived silica and alumina is an approved adjuvant added to high-volume vaccinations injected intramuscularly and subcutaneously.

These challenges suggest revisiting the original fluorescent core-shell SNP (C dot) synthesis in order to systematically develop a water based approach to <10 nm organic-inorganic hybrid dots with improved size control, previously unknown compositions, and enhanced performance characteristics.

SUMMARY OF THE DISCLOSURE

The present disclosure provides nanoparticles (e.g., core or core-shell nanoparticles). The present disclosure also provides methods of making and using the nanoparticles.

In an aspect, the present disclosure provides a method of making functionalized nanoparticles (e.g., ultrasmall functionalized nanoparticles). The methods can include a post-PEGylation surface modification by insertion (PPSMI) approach such as, for example, a (PPSMI) approach as described herein.

The methods are based on reaction of a nanoparticle (e.g., having a size such as, for example, a longest dimension) of 2 to 15 nm (e.g., 2 to 10 nm), which may be ultrasmall nanoparticles less than 10 nm in size (e.g., 2 to 9.99 nm in size) that comprises a plurality of polyethylene glycol (PEG) groups, some or all of which may be functionalized with one or more functional groups or groups that can be reacted to form functional groups, covalently bound to the surface of the nanoparticle (which may be referred to as a PEGylated nanoparticle) with one or more functionalizing precursor comprising at least one reactive group. The resulting nanoparticles with one or more reactive groups covalently bound to the surface of the nanoparticle are subsequently reacted with a functional group precursor that reacts with a reactive group resulting in a nanoparticle with one or more functional group covalently bound to the surface of the nanoparticle.

In an aspect, the present disclosure provides compositions comprising nanoparticles of the present disclosure. The compositions can comprise one or more types (e.g., having different average size and/or one or more different compositional feature). The compositions can comprise functionalized nanoparticles with one to five (e.g., 1, 2, 3, 4, or 5) types of different functional ligands disposed on (e.g., covalently bonded to) a NP surface.

In an aspect, the present disclosure provides uses of the nanoparticles and compositions of the present disclosure. The ligands (functional groups) carried by the nanoparticles can include diagnostic and/or therapeutic agents (e.g., drugs). Accordingly, nanoparticles or a composition comprising the nanoparticles are used in delivery (e.g., therapeutic methods) and/or imaging methods.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
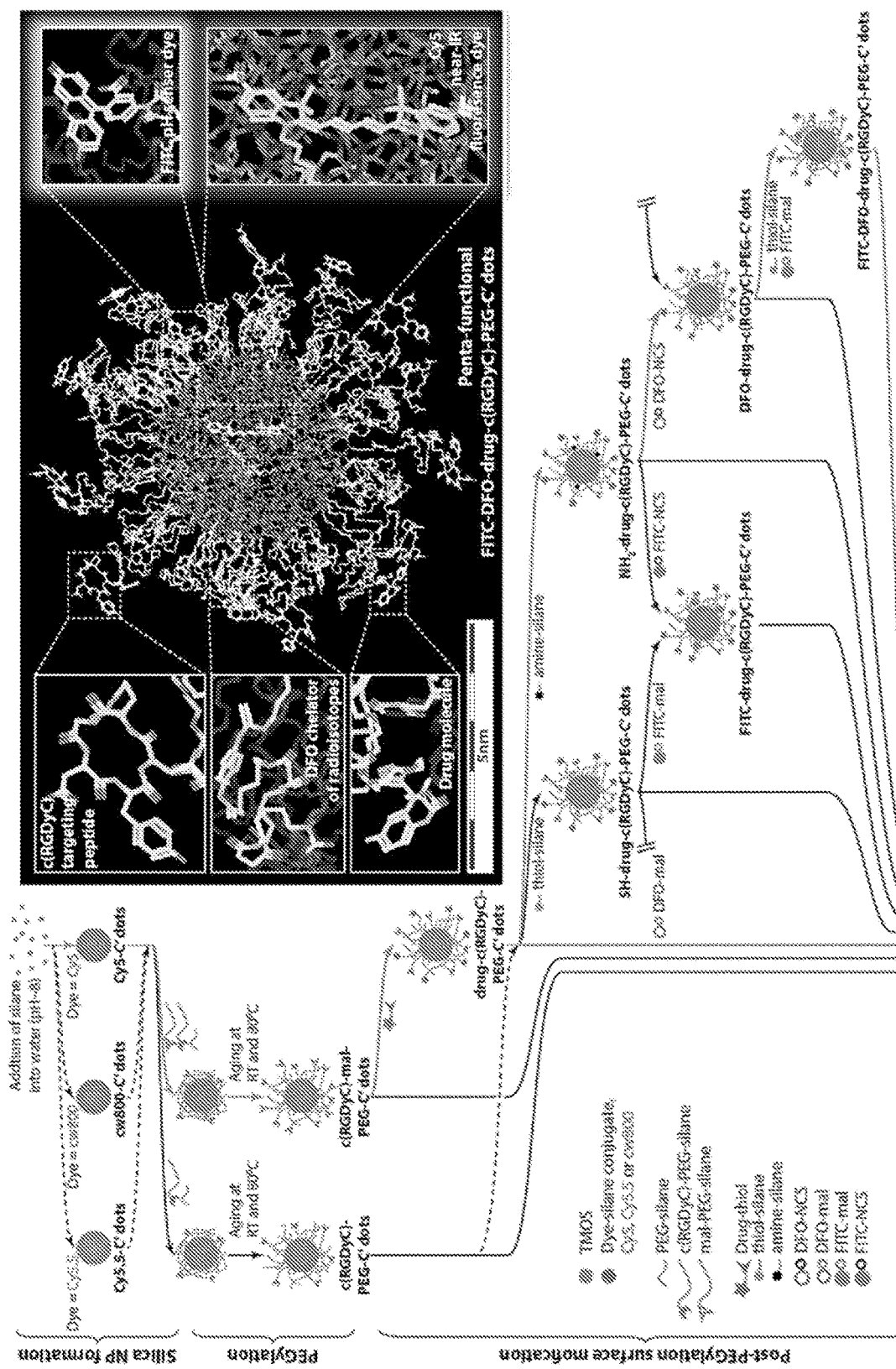
FIG. 1 shows an illustration of C' dot synthesis system introducing post-PEGylation surface modification by insertion (PPSMI) method. Surface modification of C' dots with additional functional ligands is either achieved by (i) co-condensing different heterobifunctional PEG-silanes during the PEGylation step and then covalently attaching functional ligands to the heterobifunctional PEGs after PEGylation, or by (ii) covalently inserting silanes with functional groups, e.g. amines or thiols, between the PEG chains and onto the silica surface in post-PEGylation step(s) (PPSMI). Alternative pathways in each reaction step are displayed using dashed lines. Specific choices of reaction pathways towards different multifunctional C' dots depend on application requirements. The thiol-ene reaction used to convert SH-drug-c(RGDyC)-PEG-C' dots to DFO-drug-c(RGDyC)-PEG-C' dots is shown using a break in the solid black line (bottom right). The top right insert shows a molecular rendering of a penta-functional C' dot whose synthesis pathway is highlighted with light blue color. The five functions include fluorescence via NIR fluorescent Cy5 dye inside the silica core, cancer cell targeting via specific c(RGDyC) peptides, small therapeutic EFV drugs attached to some of the PEG chains, radioisotope labeling via specific DFO chelators, and pH sensing via attachment of a second sensor FITC dye, the latter two between the PEG chains. Silicon, oxygen, carbon, nitrogen, sulfur, chlorine and fluorine atoms are colored in purple, red, gray, blue, yellow, green and light green, respectively. Hydrogen atoms are not displayed for better visualization.

The present disclosure provides nanoparticles (e.g., core or core-shell nanoparticles). In various examples, the nanoparticles are ultrasmall nanoparticles. The present disclosure also provides methods of making and using the nanoparticles.

All ranges provided herein include all values that fall within the ranges to the tenth decimal place, unless indicated otherwise.

As used herein, unless otherwise stated, the term "group," when used in the context of a chemical structure, refers to a chemical entity that has one or more terminus that can be covalently bonded to other chemical species. Non-limiting illustrative examples of groups include:

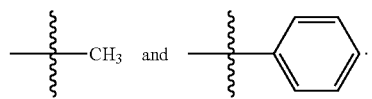

Additional non-limiting illustrative examples of groups include:

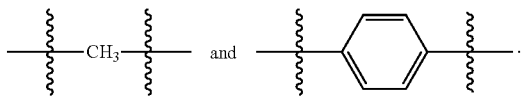

As used herein, unless otherwise indicated, the term "alkyl" refers to branched or unbranched saturated hydrocarbon groups. Examples of alkyl groups include, but are not limited to, methyl groups, ethyl groups, propyl groups, butyl groups, isopropyl groups, tert-butyl groups, and the like. For example, the alkyl group can be a $C_1$ to $C_8$, alkyl group including all integer numbers of carbons and ranges of numbers of carbons therebetween (e.g., $C_1$, $C_2$, $C_3$, $C_4$, $C_5$, $C_6$, $C_7$, and $C_8$). The alkyl group can be unsubstituted or substituted with one or more substituent. Examples of substituents include, but are not limited to, various substituents such as, for example, halogens (—F, —Cl, —Br, and —I), aliphatic groups (e.g., alkyl groups, alkenyl groups, alkynyl groups), aryl groups, alkoxide groups, amine groups, carboxylate groups, carboxylic acids, ether groups, alcohol groups, alkyne groups (e.g., acetylenyl groups), and the like, and combinations thereof.

The techniques disclosed herein provide an aqueous synthesis approach to ultrasmall functional PEGylated fluorescent silica nanoparticles with improved control in multiple aspects, including particle size, particle size distribution, fluorescence wavelength, fluorescence brightness, compositions, particle PEGylation, particle surface functionalization, synthesis yield, product purity and manufacture reliability. The systematic and precise control covering these aspects in a single organic-inorganic hybrid nanomaterials synthesis system has never been achieved before, preventing the safe translation of organic-inorganic hybrid nanomaterials from the laboratory to the clinic. Therefore, the techniques disclosed herein provide access to well-defined and systematically tunable silica-based nanomaterials that show significant potential in nanomedicine applications.

Disclosed herein is a versatile surface modification approach to, for example, modularly and orthogonally functionalize nanoparticles (e.g., Cornell prime dots (C' dots), which can be, for example, nanoparticles of the present disclosure (e.g., ultrasmall sub-10 nm PEGylated core or core-shell silica or aluminosilca nanoparticles) with one to five (e.g., 1, 2, 3, 4, or 5) types of different functional ligands on the NP surface. The surface modification approach takes advantage of gaps in the PEG groups disposed on a nanoparticle surface and inserted anchoring groups using, for example, amine and/or thiol functionalized silane molecules that can be functionalized with various functional ligands.

In an example, the modification approach provides a synthesis of penta-functional nanoparticles (e.g., C' dots) integrating a variety of properties into a single NP, e.g., fluorescence detection, specific cell targeting, radioisotope chelating/labeling, ratiometric pH sensing, drug delivery or a combination thereof, while the overall NP size remains, for example, below 10 nn (e.g., below 8 nm or below 7 nm). This is achieved by taking advantage of the fact that the PEG layer of C' dots is penetrable to small molecules.

For example, amine- and/or thiol-functionalized silane molecules can be inserted between PEG chains and onto the silica surface of nanoparticles (e.g., C' dots), to which additional functional ligands can subsequently be attached. This post-PEGylation surface modification by insertion (PPSMI) approach only requires a few extra steps sandwiched between nanoparticle (e.g., C' dot) PEGylation and purification in a one-pot type water-based synthesis without diminishing high quality NP generation. The resulting nanoparticles (e.g., C' dots) with additional functionalities exhibit physico-chemical properties like their size and PEG density close to clinically translated nanoparticles (e.g., C dots), opening a gate to the diversification of their clinical applications. Modification of a nanoparticle synthesis (e.g., a C' dot synthesis) enables, for example, large numbers of targeting peptides per particle, as well as a facile and versatile spectroscopic approach to quantitatively assess the specific numbers of the different surface ligands by deconvolution of absorption spectra into individual components.

In an aspect, the present disclosure provides a method of making functionalized nanoparticles (e.g., ultrasmall functionalized nanoparticles). The methods can include a PPSM) approach such as, for example, a PPSMI approach as described herein. The methods are based on use of aqueous reaction medium (e.g. water). In an example, a nanoparticle or nanoparticles (e.g., nanoparticles of a composition) of the present disclosure are made by a method of the present disclosure.

The methods are based on reaction of a nanoparticle (e.g., having a size such as, for example, a longest dimension) of 2 to 15 nm (e.g., 2 to 10 nm), which may be ultrasmall nanoparticles less than 10 nm in size (e.g., 2 to 9.99 nm in size) that comprises a plurality of polyethylene glycol (PEG) groups, some or all of which may be functionalized with one or more functional groups or groups that can be reacted to form functional groups, covalently bound to the surface of the nanoparticle (which may be referred to as a PEGylated nanoparticle) with one or more functionalizing precursor comprising at least one reactive group. The resulting nanoparticles with one or more reactive groups covalently bound to the surface of the nanoparticle are subsequently reacted with a functional group precursor that reacts with a reactive group resulting in a nanoparticle with one or more functional group covalently bound to the surface of the nanoparticle.

The methods may be "one-pot" reactions. The methods may also comprise individual reactions. The individual reactions may have reaction mixtures with the same or different reactants (e.g., nanoparticles, functionalizing precursor(s), functional group precursor(s), solvent(s), etc., and various combinations thereof). The nanoparticles may be isolated between any individual reaction(s).

In an example, a PEGylated nanoparticle is reacted with one or more functionalizing precursors and one or more functional group precursor. The reactions can be carried out in any order, so long as the nanoparticle is first reacted with at least one functionalizing precursor. For example, a nanoparticle with a single type of reactive group is reacted with one or more functional group precursor. In another example, a nanoparticle with two or more structurally and/or chemically different reactive groups (e.g., 2, 3, 4, or 5 structurally and/or chemically different reactive groups) is reacted with two or more different functional group precursors (e.g., 2, 3, 4, or 5 structurally and/or chemically different functional group precursors), where the individual reactive groups/functional group precursors may have orthogonal reactivity.

Various conjugation chemistries/reactions can be used to covalently link a functional group to the surface of a nanoparticle. Accordingly, a functionalizing precursor can comprise various reactive groups. Numerous suitable conjugation chemistries and reactions are known in the art. In various examples, a reactive group is one that reacts in particular conjugation chemistry or reaction known in the art and the functional group precursor comprises a complementary group of the particular conjugation chemistries/reactions known in the art.

Functionalizing precursors comprise one or more reactive group and a group (e.g., a silane group) that can react with the surface of the nanoparticle to form a covalent bond. The reactive group(s) can react with a functional group precursor to form a functional group that is covalently bound to the surface of the nanoparticle. Non-limiting examples of reactive groups include an amine group, a thiol group, a carboxylic acid group, a carboxylate group, an ester group (e.g., an activated ester group), a maleimide group, an allyl group, a terminal alkyne group, an azide group, a thiocyanate group, and combinations thereof. Examples of functionalizing precursors are known in the art and are commercially available or can be made using methods known in the art.

In various examples, a functionalizing precursor comprises a silane group that comprises one or more —Si—OH group (e.g., 1, 2, or 3 Si—OH groups) and at least one reactive group (e.g., 1, 2, or 3 reactive groups). The silane group(s) and reactive group(s) may be coventlly bonded via a linking group such as, for example, an alkyl group (e.g., a $C_1$, $C_2$, $C_3$, $C_4$, $C_5$, $C_6$, $C_7$, or $C_8$ alkyl group). Without intending to be bound by any particular theory, it is considered that the Si—OH group of the functionalizing precursor reacts with a surface hydroxyl group of the nanoparticle (e.g., a surface Si—OH group).

A nanoparticle or a plurality of nanoparticles can be reacted to form various numbers of reactive groups and/or functional groups. For example, a nanoparticle or a plurality of nanoparticles is reacted to form 1 to 100 reactive group(s) and/or functional group(s), including all integer number of reactive groups and ranges therebetween, (e.g., plurality of nanoparticles is reacted to form an average of 1 to 100 group(s) and/or functional group(s), including all integer number of reactive groups and ranges therebetween, per nanoparticle for a plurality of nanoparticles) covalently bound to the surface of the nanoparticle or plurality of nanoparticles. In various examples, a nanoparticle or a plurality of nanoparticles is reacted to form 20 to 100, 25 to 100, 30 to 100, 35 to 100, 40 to 100, or 50 to 100 group(s) and/or functional group(s) (e.g., plurality of nanoparticles can be reacted to form an average of 20 to 100, 25 to 100, 30 to 100, 35 to 100, 40 to 100, or 50 to 100 group(s) and/or functional group(s) covalently bound to the surface of each of the nanoparticles. Determining reaction conditions (e.g., reactant concentrations, reaction time, reaction temperature, and the like, or a combination thereof) to form a desired number of group(s) and/or functional group(s) is within the purview of one having skill in the art.

A functional group precursor can react with a reactive group of a nanoparticle to form a functional group covalently bound to a surface of the nanoparticle. A functional group pecursor comprises a functional group (e.g., a dye group, chelator group, targeting group, drug group, radio label/isotope group, and the like, which may be derived from a dye molecule, chelator molecule, targeting molecule, etc.) and a group that can react with a reactive group of a nanoparticle. Non-limiting examples of groups that react with a reactive group include an amine group, a thiol group, a carboxylic acid group, a carboxylate group, an ester group (e.g., an activated ester group), a maleimide group, an allyl group, a terminal alkyne group, an azide group, a thiocyanate group, and combinations thereof. In various examples, a functional group precursor comprises one or more group that react in a particular conjugation chemistry or reaction known in the art (e.g., the functional group precursor comprises one or more group, such as, for example, an azide, that is complementary to a reactive group of the nanoparticle, such as for example, a terminal alkyne, in a particular conjugation chemistry/reaction, such as, for example, click chemistry, known in the art). Examples of functional group precursors are known in the art and are commercially available or can be made using methods known in the art.

Various functional groups are known in the art. A functional group may also be referred to herein as a ligand. The functional groups have various functionality (e.g., absorption/emission behavior such as, for example, fluorescence and phosphorescence, which can be used for imaging, sensing functionality (e.g., pH sensing, ion sensing, oxygen sensing, biomolecules sensing, temperature sensing, and the like), chelating ability, targeting ability (e.g., antibody fragments, apatmers, proteins/peptides (natural, truncated, or synthetic), nucleic acids such as, for example, DNA and RNA, and the like), diagnostic ability (e.g., radioisotopes), therapeutic ability (e.g, drugs, nucleic acids and the like), and the like and combinations thereof. A functional group may have both imaging and therapeutic functionality. A functional group can be formed from a compound exhibiting functionality by derivatization of the compound using conjugation chemistry and reactions known in the art.

The functional group(s) carried by the nanoparticles can include diagnostic and/or therapeutic agents (e.g., radioisotopes, drugs, nucleic acids, and the like). A nanoparticle may comprise a combination of different functional groups.

Non-limiting examples of therapeutic agents, which may be drugs, include, but are not limited to, chemotherapeutic agents, antibiotics, antifungal agents, antiparasitic agents, antiviral agents, and combinations thereof, and groups derived therefrom. Examples of suitable drugs/agents are known in the art.

A nanoparticle can comprise various dyes (e.g., functional groups formed from various dyes). In various examples, the dyes are organic dyes. In an example, a dye does not comprise a metal atom. Non-limiting examples of dyes include fluorescent dyes (e.g, near infrared (NIR) dyes), phosphorescent dyes, non-fluorescent dyes (e.g., non-fluorescent dyes exhibiting less than 1% fluorescence quantum yield), fluorescent proteins (e.g., EBFP2 (variant of blue fluorescent protein), mCFP (Cyan fluorescent protein), GFP (green fluorescent protein), mCherry (variant of red fluorescent protein), iRFP720 (Near Infra-Red fluorescent protein)), and the like, and groups derived therefrom. In various examples, a dye absorbs in the UV-visible portion of the electromagnetic spectrum. In various examples, a dye has an excitation and/or emission in the near-infrared portion of the electromagnetic spectrum (e.g., 650-900 nm).

Non-limiting examples of organic dyes include cyanine dyes (e.g., Cy5®, Cy3®, Cy5.5®, Cy7®, and the like), carborhodamine dyes (e.g., ATTO 647N (available from ATTO-TEC and Sigma Aldrich®), BODIPY dyes (e.g., BODIPY 650/665 and the like), xanthene dyes (e.g., fluorescein dyes such as, for example, fluorescein isothiocyanate (FITC), Rose Bengal, and the like), eosins (e.g. Eosin Y and the like), and rhodamines (e.g. TAMRA, tetramethylrhodamine (TMR), TRITC, DyLight® 633, Alexa 633, HiLyte 594, and the like), Dyomics® DY800, Dyomics® DY782 and IRDye® 800CW, and the like, and groups derived therefrom.

A nanoparticle can comprise various sensor groups. Non-limiting examples of sensor groups include pH sensing groups, ion sensing groups, oxygen sensing groups, biomolecule sensing groups, temperature sensing groups, and the like. Examples of suitable sensing compounds/groups are known in the art.

A nanoparticle can comprise various chelator groups. Non-limiting examples of chelator groups include desferoxamine (DFO), 1,4,7,10-Tetraazacyclododecane-1,4,7,10-tetraacetic acid (DOTA), 1,4,7-triazacyclononane-1,4,7-triacetic acid (NOTA), ethylenediaminetetraacetic acid (EDTA), diethylenetriaminepentaacetic acid (DTPA), porphyrins, and the like, and groups derived therefrom. A chelator group may comprise a radioisotope. Examples of radioisotopes are described herein and are known in the art.

A radioisotope can be a functional group. A radioisotope can be a diagnostic agent and/or a therapeutic agent. For example, a radioisotope, such as for example, $^{124}$I, is used for positron emission tomography (PET). Non-limiting examples of radioisotopes include $^{124}$I, $^{131}$I, $^{225}$Ac, $^{177}$Lu, and the like. A radioisotope may be chelated to a chelating group.

A targeting group may also be conjugated to the nanoparticle to allow targeted delivery of a nanoparticle or nanoparticles. A targeting group can be formed from (derived from) a targeting molecule. For example, a targeting group, which is capable of binding to a cellular component (e.g., on the cell membrane or in the intracellular compartment) associated with a specific cell type, is conjugated to the nanoparticle. The targeting group may be a tumor marker or a molecule in a signaling pathway. The targeting group may have specific binding affinity to certain cell types, such as, for example, tumor cells. In certain examples, the targeting group may be used for guiding the nanoparticles to specific areas, such as, for example, liver, spleen, brain or the like. Imaging can be used to determine the location of the nanoparticles in an individual. Examples of targeting groups include, but are not limited to, linear and cyclic peptides (e.g., 43 integrin-targeting cyclic (arginine-glycine-aspartic acid, tyrosine-cysteine) peptides, c(RGDyC), and the like), antibody fragments, various DNA and RNA segments (e.g. siRNA).

As used herein, unless otherwise stated, the term "derived" refers to formation of a group by reaction of a native functional group of a compound (e.g., formation of a group via a reaction of an amine of a compound and a carboxylic acid to form a group) or chemical modification of a compound to introduce a new chemically reactive group on the compound that is reacted to form a group.

The methods as described herein can be linearly scaled up, e.g., from 10 ml reaction to 1000 ml or greater without any substantial change in product quality. This scalability is important for large scale manufacture of the nanoparticles.

The methods may carried out in an aqueous reaction medium (e.g., water). For example, the aqueous medium comprises water. Certain reactants are added to the various reaction mixtures as solutions in a polar aprotic solvent (e.g., DMSO or DMF). In various examples, the aqueous medium does not contain organic solvents (e.g., alcohols such as $C_1$ to $C_6$ alcohols) other than polar aprotic solvents at 10% or greater, 20% or greater, or 30% or greater. In an example, the aqueous medium does not contain alcohols at 1% or greater, 2% or greater, 3% or greater, 4% or greater, or 5% or greater. In an example, the aqueous medium does not contain any detectable alcohols. For example, the reaction media of any of the steps of any of the methods disclosed herein consists essentially of water and, optionally, a polar aprotic solvent.

At various points in the methods the pH can be adjusted to a desired value or within a desired range. The pH the reaction mixture can be increased by addition of a base. Non-limiting examples of suitable bases include ammonium hydroxide.

Various nanoparticles can be used. Non-limiting examples of nanoparticles include silica nanoparticles and aluminosilicate nanoparticles. The nanoparticles may be core-shell nanoparticles. The nanoparticles are surface functionalized with polyethylene glycol groups (e.g., PEGylated), some or all of which may be functionalized with one or more functional groups or groups that can be reacted to form functional groups. The nanoparticles may comprise PEG groups with groups that can be reacted to form functional groups. These nanoparticles may be functionalized with one or more functional groups. For example, a functionalized ligand (functional group precursor) is reacted with a reactive group of a PEG group. Examples of suitable reaction chemistries and conditions for post-nanoparticle synthesis functionalization of PEG groups are known in the art. Suitable nanoparticles and methods of making such nanoparticles are disclosed in U.S. patent application Ser. No. 15/571,420, filed Nov. 2, 2017, the disclosure of which with respect to such nanoparticles and methods is incorporated herein by reference.

For example, a method of making nanoparticles or core-shell nanoparticles surface, which are surface functionalized with polyethylene glycol groups (i.e., PEGylated) comprises: a) forming a reaction mixture at room temperature (e.g., 15° C. to 25° C. depending on the location) comprising water and TMOS (a silica core forming monomer) (e.g., at a concentration of 11 mM to 270 mM), wherein the pH of the reaction mixture (which can be adjusted using a base such as, for example, ammonium hydroxide) is 6 to 9 (which results in formation of core precursor nanoparticles having an average size (e.g., longest dimension) of, for example, 1 nm to 2 nm); b) either i) holding the reaction mixture at a time ($t^1$) and temperature ($T^1$) (e.g., ($t^1$) 0.5 days to 7 days at room temperature to 95° C. (T')), whereby nanoparticles (core nanoparticles) having an average size (e.g., longest dimension) of 2 to 15 nm are formed, or ii) cooling the reaction mixture to room temperature, if necessary, and adding a shell forming monomer (e.g., tetraethyl orthosilicates, other than TMOS, such as, for example, TEOS or TPOS) (the addition is carried out such that the shell forming monomer concentration is below the threshold for secondary nucleation) to the reaction mixture from a), whereby core-shell nanoparticles having an average size (e.g., longest dimension) of 2 to 50 nm (e.g., 2 to 15 nm) are formed; c) adjusting, if necessary, the pH of the reaction mixture to a pH of 6 to 10 comprising the core nanoparticles or core-shell nanoparticles from b) i) or b) ii), respectively; and d) optionally (PEGylating the core nanoparticles or core-shell nanoparticles by) adding at room temperature to the reaction mixture comprising the core nanoparticles or core-shell nanoparticles from b) i) or b) ii), respectively, a PEG-silane conjugate (comprising a PEG group covalently bound to a silane group) (e.g., at a concentration of 10 mM to 60 mM) (e.g., PEG-silane conjugate dissolved in a polar aprotic solvent such as, for example, DMSO or DMF) and holding the resulting reaction mixture at a time ($t^2$) and temperature ($T^2$) (e.g., ($t^2$) 0.5 minutes to 24 hours at room temperature ($T^2$)) (whereby at least a portion of the PEG-silane conjugate molecules are adsorbed on at least a portion of the surface of the core nanoparticles or core-shell nanoparticles from b)); e) heating the mixture from d) at a time ($t^3$) and temperature ($T^3$) (e.g., ($t^3$) 1 hour to 24 hours at 40° C. to 100° C. ($T^3$)), whereby the nanoparticles surface functionalized with polyethylene glycol groups or the core-shell nanoparticles surface functionalized with polyethylene glycol groups are formed.

The nanoparticles can be subjected to post-synthesis processing steps. For example, after synthesis (e.g., after e) in the example above) the solution is cooled to room temperature and then transferred into a dialysis membrane tube (e.g. a dialysis membrane tube having a Molecular Weight cut off of 10,000, which are commercially available (e.g., from Pierce)). The solution in the dialysis tube is dialyzed in DI-water (volume of water is 200 times more than the reaction volume, e.g. 2000 ml water for a 10 ml reaction) and the water is changed every day for one to six days to wash away remaining reagents, e.g. ammonium hydroxide and free silane molecules. The particles are then filtered through a 200 nm syringe filter (fisher brand) to remove aggregates or dust. If desired, additional purification processes, including gel permeation chromatography and high-performance liquid chromatography, can be applied to the nanoparticles to further ensure the high purify of the synthesized particles (e.g., 1% or less unreacted reagents or aggregates). After any purification processes, the purified nanoparticles can be transferred back to deionized water if other solvent is used in the additional processes.

The cores can be silicon cores. The reaction mixture used in silicon core formation can comprise TMOS as the only silicon core forming monomer.

The cores can be aluminosilicate cores. The reaction mixture used in aluminosilicate core formation can comprise TMOS as the only silicon core forming monomer and one or more alumina core forming monomer (e.g., an aluminum alkoxide such as, for example, aluminum-tri-sec-butoxide or a combination of aluminum alkoxides).

In the case of aluminosilicate core synthesis, the pH of the reaction mixture is adjusted to a pH of 1 to 2 prior to addition of the alumina core forming monomer. After aluminosilicate core formation, the pH of the solution is adjusted to a pH of 7 to 9 and, optionally, PEG with molecular weight between 100 and 1,000 g/mol, including all integer values and ranges therebetween, at concentration of 10 mM to 75 mM, including all integer mM values and ranges therebetween, is added to the reaction mixture prior to adjusting the pH of the reaction mixture to a pH of 7 to 9.

The reaction mixture used to form core nanoparticles can also comprise a dye precursor. In this case, the resulting core or core-shell nanoparticles have one or more dye molecules encapsulated or incorporated therein. For example, core nanoparticle has 1, 2, 3, 4, 5, 6, or 7 dye molecules encapsulated therein. Mixtures of dye precursors can be used. The dye precursor is a dye conjugated to a silane. For example, a dye with maleimido functionality is conjugated to thiol-functionalized silane. In another example, a dye with NHS ester functionality is conjugated to amine-functionalized silane. Examples of suitable silanes and conjugation chemistries are known in the art. The dye can have an emission (e.g., fluorescence) wavelength of 400 nm (blue) to 800 nm (near-infrared). For example, the dye is a NIR-dye. Examples of suitable dyes are described herein. In various examples, the nanoparticles surface functionalized with polyethylene glycol groups or the core-shell nanoparticles surface functionalized with polyethylene glycol groups have one or more fluorescent dye molecules encapsulated therein.

A silica shell can be formed on the core nanoparticles. The silica shell is formed after, for example, core formation is complete. Examples of silica shell forming precursors include tetraalkylorthosilicates such as, for example, TEOS and TPOS. Mixtures of silica shell forming precursors can be used. TMOS is not a silica shell forming precursor. The silica shell forming precursor can be added to the reaction mixture as a solution in a polar aprotic solvent. Examples, of suitable polar aprotic solvents include DMSO and DMF.

It is desirable to add the silica shell forming precursors in separate aliquots. For example the shell forming monomer(s) is/are added in separate aliquots (e.g., 40 to 500 aliquots) The aliquots can include one or more shell forming precursor (e.g., TEOS and/or TPOS) and a polar aprotic solvent e.g., DMSO. Each aliquot can have 1 to 20 micromoles of shell forming monomer. The interval between aliquot addition can be 1 to 60 minutes, including all integer minute values and ranges therebetween. The pH of the reaction mixture can vary during the silica shell forming process. It is desirable to adjust the pH to maintain a pH of 7-8.

After core or core-shell nanoparticle formation, the core or core-shell nanoparticles can by reacted with one or more PEG-silane conjugates. Various PEG-silane conjugates can be added together or in various orders. This process is also referred to herein as PEGylation. The conversion percentage of PEG-silane is between 5% and 40% and the polyethylene glycol surface density is 1.3 to 2.1 polyethylene glycol molecules per $nm^2$. The conversion percentage of ligand-functionalized PEG-silane is 40% to 100% and the number of ligand-functionalized PEG-silane precursors reacted with each particle is 3 to 90.

PEGylation can be carried out at a variety of times and temperatures. For example, in the case of silica core or core-shell nanoparticles, PEGylation can be carried out by contacting the nanoparticles at room temperature for 0.5 minutes to 24 hours (e.g., overnight). For example, in the case of alumina-silicate nanoparticles (e.g., alumina-silicate core nanoparticles or silica core silica shell nanoparticles) the temperature is 80° C. overnight.

The chain length of the PEG group of the PEG-silane (i.e., the molecular weight of the PEG group) can be tuned from 3 to 24 ethylene glycol monomers (e.g., 3 to 6, 3 to 9, 6 to 9, 8 to 12, or 8 to 24 ethylene glycol monomers). The PEG chain length of PEG-silane can be selected to tune the thickness of the PEG layer surrounding the particle and the pharmaceutical kinetics profiles of the PEGylated particles. The PEG chain length of ligand-functionalized PEG-silane can be used to tune the accessibility of the ligand groups on the surface of the PEG layer of the particles resulting in varying binding and targeting performance.

PEG-silane conjugates can comprise a ligand. The ligand is covalently bound to the PEG group of the PEG-silane conjugates (e.g., via though the hydroxy terminus of the PEG-silane conjugates). The ligand can be conjugated to a terminus of the PEG group opposite the terminus conjugated to the silane group. The PEG-silane conjugate can be formed using a heterobifunctional PEG compound (e.g., maleimido-functionalized heterobifunctional PEGs, NHS ester-functionalized heterobifunctional PEGs, amine-functionalized heterobifunctional PEGs, thiol-functionalized heterobifunctional PEGs, etc.). Examples of suitable ligands (functional groups) are described herein.

For example, PEG-silane conjugate comprising a ligand is added in addition to PEG-silane (e.g., in d) in the example above). In this case, nanoparticles surface functionalized with polyethylene glycol groups and polyethylene groups comprising a ligand or core-shell nanoparticles surface functionalized with polyethylene glycol groups and polyethylene groups comprising a ligand are formed. The conversion percentage of ligand-functionalized or reactive group-functionalized PEG-silane is 40% to 100% and the number of ligand-functionalized PEG-silane precursors reacted with each particle is 3 to 600.

For example, before or after (e.g., 20 seconds to 5 minutes before or after) the PEG-silane conjugate is added (e.g., in d) in the example above) a PEG-silane conjugate comprising a ligand (e.g., at concentration between 0.05 mM and 2.5 mM) is added at room temperature to the reaction mixture comprising the core nanoparticles or core-shell nanoparticles (e.g., from b) i) or b) ii), respectively, in the example above). The resulting reaction mixture is held at a time ($t^4$) and temperature ($T^4$) (e.g., ($t^4$) 0.5 minutes to 24 hours at room temperature ($T^4$)), where at least a portion of the PEG-silane conjugate molecules are adsorbed on at least a portion of the surface of the core nanoparticles or core-shell nanoparticles (e.g., from b) in the example above). Subsequently, the reaction mixture is heated at a time ($t^5$) and temperature ($T^5$) (e.g., ($t^5$) 1 hour to 24 hours at 40° C. to 100° C. ($T^5$)), where nanoparticles surface functionalized with polyethylene glycol groups comprising a ligand or core-shell nanoparticles surface functionalized with polyethylene glycol groups comprising a ligand are formed. Optionally, subsequently adding at room temperature to the resulting reaction mixture comprising nanoparticles surface functionalized with polyethylene glycol groups comprising a ligand or core-shell nanoparticles surface functionalized with polyethylene glycol groups comprising a ligand a PEG-silane conjugate (the concentration of PEG-silane no ligand is between 10 mM and 75 mM) (e.g., PEG-silane conjugate dissolved in a polar aprotic solvent such as, for example, DMSO or DMF), holding the resulting reaction mixture at a time ($t^6$) and temperature ($T^6$) (e.g., ($t^6$) 0.5 minutes to 24 hours at room temperature ($T^6$)) (whereby at least a portion of the PEG-silane conjugate molecules are adsorbed on at least a portion of the surface of the nanoparticles surface functionalized with polyethylene glycol groups comprising a ligand or at least a portion of the core-shell nanoparticles surface functionalized with polyethylene glycol groups comprising a ligand a PEG-silane conjugate, and heating the resulting mixture from at a time (f) and temperature ($T^7$) (e.g., (f) 1 hour to 24 hours at 40° C. to 100° C. ($T^7$)), whereby nanoparticles surface functionalized with polyethylene glycol groups and polyethylene glycol groups comprising a ligand or core-shell nanoparticles surface functionalized with polyethylene glycol groups and polyethylene groups comprising a ligand are formed.

In another example, at least a portion of or all of the PEG-silane has a reactive group on a terminus of the PEG group opposite the terminus conjugated to the silane group of the PEG-silane conjugate (is formed from a heterobifunctional PEG compound) and after formation of the nanoparticles surface functionalized with polyethylene glycol groups having a reactive group, and, optionally, polyethylene glycol groups, core-shell nanoparticles surface functionalized with polyethylene glycol groups having a reactive group. Optionally, polyethylene glycol groups are reacted with a second ligand (which can be the same or different than the ligand of the nanoparticles surface functionalized with polyethylene glycol groups and polyethylene glycol group comprising a ligand or the core-shell nanoparticles surface functionalized with polyethylene glycol groups and polyethylene groups comprising a ligand) functionalized with a second reactive group (which can be the same or different than the reactive group of the nanoparticles surface functionalized with polyethylene glycol groups and polyethylene glycol group comprising a ligand or the core-shell nanoparticles surface functionalized with polyethylene glycol groups and polyethylene groups comprising a ligand) thereby forming nanoparticles surface functionalized with polyethylene groups functionalized with a second ligand and, optionally, polyethylene glycol groups, core-shell nanoparticles surface functionalized with polyethylene groups functionalized with a second ligand and polyethylene glycol groups and, optionally, polyethylene glycol groups.

In another example, at least a portion of or all of the PEG-silane has a reactive group on a terminus of the PEG group opposite the terminus conjugated to the silane group of the PEG-silane conjugate (is formed from a heterobifunctional PEG compound) and after formation of the nanoparticles surface functionalized with polyethylene glycol groups and, optionally having a reactive group, and, optionally, polyethylene glycol groups, core-shell nanoparticles surface functionalized with polyethylene glycol groups having a reactive group, and, optionally, polyethylene glycol groups, are reacted with a second ligand (which can be the same or different than the ligand of the nanoparticles surface functionalized with polyethylene glycol groups and polyethylene glycol group comprising a ligand or the core-shell nanoparticles surface functionalized with polyethylene glycol groups and polyethylene groups comprising a ligand) functionalized with a second reactive group (which can be the same or different than the reactive group of the nanoparticles surface functionalized with polyethylene glycol groups and polyethylene glycol group comprising a ligand or the core-shell nanoparticles surface functionalized with polyethylene glycol groups and polyethylene groups comprising a ligand) thereby forming nanoparticles surface functionalized with polyethylene groups functionalized with a second ligand and, optionally, polyethylene glycol groups, core-shell nanoparticles surface functionalized with polyethylene groups functionalized with a second ligand and polyethylene glycol groups and, optionally, polyethylene glycol groups, where at least a portion of the PEG-silane has a reactive group on a terminus of the PEG group opposite the terminus conjugated to the silane group of the PEG-silane conjugate (is formed from a heterobifunctional PEG compound) and after formation of the nanoparticles surface functionalized with polyethylene glycol groups having a reactive group, core-shell nanoparticles surface functionalized with polyethylene glycol groups having a reactive group, nanoparticles surface functionalized with polyethylene glycol groups having a reactive group and polyethylene glycol groups comprising a ligand, or core-shell nanoparticles surface functionalized with polyethylene glycol groups having a reactive group and polyethylene groups comprising a ligand the reactive group are reacted with a second ligand functionalized with a reactive group (which can be the same or different than the ligand of the nanoparticles surface functionalized with polyethylene glycol groups and polyethylene glycol group comprising a ligand, or core-shell nanoparticles surface functionalized with polyethylene glycol groups and polyethylene groups comprising a ligand) thereby forming nanoparticles surface functionalized with polyethylene glycol groups and polyethylene groups functionalized with a second ligand, core-shell nanoparticles surface functionalized with polyethylene glycol groups and polyethylene groups functionalized with a second ligand, nanoparticles surface functionalized with polyethylene glycol groups comprising a ligand, or core-shell nanoparticles surface functionalized with polyethylene glycol groups and polyethylene groups comprising a ligand that is functionalized with the second ligand.

The nanoparticles can have a narrow size distribution. In various examples, the nanoparticle size distribution (before or after PEGylation), not including extraneous materials such as, for example, unreacted reagents, dust particles/aggregates, is +/−5, 10, 15, or 20% of the average particle size (e.g., longest dimension). The particle size can be determined by methods known in the art. For example, the particle size is determined by TEM, GPS, or DLS. DLS contains systematic deviation and, therefore, the DLS size distribution may not correlate with the size distribution determined by TEM or GPS.

A nanoparticle may comprise one or more groups (e.g., 1 to 7 dyes per nanoparticle) derived from a dye molecule other than a functional group. For example, a dye molecule or a derivative of a dye molecule as described herein is covalently bonded to the network of a nanoparticle (e.g., via a linker moiety, which may be a moiety of a dye precursor). The resulting covalently bonded dye group is derived from an original dye molecule. Illustrative, non-limiting examples of groups derived from a dye molecule are described herein. In an example, a dye is incorporated into the silica or aluminosilicate network using a dye precursor that comprises a dye conjugated to a sol-gel silica precursor (e.g., a —Si(OR)$_3$ group, where R is an alkyl group).

In an aspect, the present disclosure provides compositions comprising nanoparticles of the present disclosure. The compositions can comprise one or more types (e.g., having different average size and/or one or more different compositional feature). The compositions can comprise functionalized nanoparticles with one to five (e.g., 1, 2, 3, 4, or 5) types of different functional ligands disposed on (e.g., covalently bonded to) a NP surface. (e.g., penta-functional nanoparticles (e.g., C' dots) integrating a variety of properties into a single NP, i.e. fluorescence detection, specific cell targeting, radioisotope chelating/labeling, ratiometric pH sensing, and drug delivery, while the overall NP size remains below 7 nm).

For example, a composition comprises a plurality of core and/or core-shell nanoparticles (e.g., silica core nanoparticles, silica core-shell nanoparticles, aluminosilicate core nanoparticles, aluminosilicate core-shell nanoparticles. Any of the nanoparticles may be surface functionalized with one or more type of polyethylene glycol groups (e.g., polyethylene glycol groups, functionalized (e.g., functionalized with one or more ligand and/or a reactive group) polyethylene glycol groups, or a combination thereof). Any of the nanoparticles may have a dye or combination of dyes (e.g., a NIR dye) encapsulated therein. The dye molecules are covalently bound to the nanoparticles. The nanoparticles can be made by a method of the present disclosure.

The nanoparticles in a composition can have a variety of sizes. The nanoparticles can have a core size of 2 to 15 nm, including all 0.1 nm values and ranges therebetween. In various examples, the nanoparticles have a core size of 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 nm. In various examples, at least 90%, 95%, 96%, 97%, 98%, 99%, 99.5% 99.9%, or 100% of the nanoparticles (e.g., core and/or core-shell nanoparticles) have a size (e.g., longest dimension) of 2 to 15 nm. The nanoparticles may be ultrasmall nanoparticles. In various examples, ultrasmall nanoparticles (e.g., ultrasmall core and/or core-shell nanoparticles) have a size of 10 nm or less (e.g., 2-8 nm or 2-7 nm). In various examples, at least 90%, 95%, 96%, 97%, 98%, 99%, 99.5% 99.9%, or 100% of the ultrasmall nanoparticles (e.g., ultrasmall core and/or core-shell nanoparticles) have a size (e.g., longest dimension) 10 nm or less (e.g., 2-8 nm or 2-7 nm). For the exemplary size distributions, the composition may not be subjected to any particle-size discriminating (particle size selection/removal) processes (e.g., filtration, dialysis, chromatography (e.g., GPC), centrifugation, etc.). For example, the nanoparticles of the present disclosure are the only nanoparticles in the composition.

The composition can comprise additional components. For example, the composition can also comprise a buffer suitable for administration to an individual (e.g., a mammal such as, for example, a human). The buffer may be a pharmaceutically-acceptable carrier.

The compositions, as synthesized and before any post-synthesis processing/treatment, can have nanoparticles, particles (e.g. 2-15 nm), dust particles/aggregates (>20 nm), unreacted reagents (<2 nm).

In an aspect, the present disclosure provides uses of the nanoparticles and compositions of the present disclosure. For example, nanoparticles or a composition comprising the nanoparticles are used in therapeutic (e.g., delivery) and/or diagnostic (e.g., imaging) methods.

The ligands (functional groups) carried by the nanoparticles can include diagnostic and/or therapeutic agents (e.g., drugs). Examples of therapeutic agents include, but are not limited to, chemotherapeutic agents, antibiotics, antifungal agents, antiparasitic agents, antiviral agents, and combinations thereof. An affinity ligand may be also be conjugated to the nanoparticle to allow targeted delivery of the nanoparticles. For example, the nanoparticle may be conjugated to a ligand which is capable of binding to a cellular component (e.g., on the cell membrane or in the intracellular compartment) associated with a specific cell type. The targeted molecule can be a tumor marker or a molecule in a signaling pathway. The ligand can have specific binding affinity to certain cell types, such as, for example, tumor cells. In certain examples, the ligand may be used for guiding the nanoparticles to specific areas, such as, for example, liver, spleen, brain or the like. Imaging can be used to determine the location of the nanoparticles in an individual.

The nanoparticles or compositions comprising nanoparticles can be administered to individuals for example, in pharmaceutically-acceptable carriers, which facilitate transporting the nanoparticles from one organ or portion of the body to another organ or portion of the body. Examples of individuals include animals such as human and non-human animals. Examples of individuals also include mammals.

Pharmaceutically acceptable carriers are generally aqueous based. Some examples of materials which can be used in pharmaceutically-acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. (See REMINGTON'S PHARM. SCI., 15th Ed. (Mack Publ. Co., Easton (1975)). For example, additional suitable carriers or excipients that are nontoxic can include buffers such as, for example, acetate, Tris, phosphate, citrate, and other organic acids; antioxidants including ascorbic acid and methionine; preservatives such as, for example, octadecyldimethylbenzyl ammonium chloride; hexamethonium chloride; benzalkonium chloride, benzethonium chloride; phenol, butyl or benzyl alcohol; alkyl parabens such as, for example, methyl or propyl paraben; catechol; resorcinol; cyclohexanol; 3-pentanol; and m-cresol; amino acids such as, for example, glycine, glutamine, asparagine, histidine, arginine, or lysine; monosaccharides, disaccharides, and other carbohydrates including glucose, mannose, or dextrins; chelating agents such as, for example, EDTA; tonicifiers such as, for example, trehalose and sodium chloride; sugars such as, for example, sucrose, mannitol, trehalose or sorbitol; surfactant such as, for example, polysorbate; salt-forming counter-ions such as, for example, sodium; and/or non-ionic surfactants such as, for example, Tween or polyethylene glycol (PEG). The pharmaceutical compositions may comprise other therapeutic agents.

Compositions comprising the present nanoparticles can be administered to an individual by any suitable route—either alone or as in combination with other agents. Administration can be accomplished by any means, such as, for example, by parenteral, mucosal, pulmonary, topical, catheter-based, or oral means of delivery. Parenteral delivery can include, for example, subcutaneous, intravenous, intramuscular, intra-arterial, and injection into the tissue of an organ. Mucosal delivery can include, for example, intranasal delivery. Pulmonary delivery can include inhalation of the agent. Catheter-based delivery can include delivery by iontophoretic catheter-based delivery. Oral delivery can include delivery of an enteric coated pill, or administration of a liquid by mouth. Transdermal delivery can include delivery via the use of dermal patches.

Following administration of a composition comprising the present nanoparticles, the path, location, and clearance of the NPs can be monitored using one or more imaging techniques. Examples of suitable imaging techniques include Artemis Fluorescence Camera System.

This disclosure provides a method for imaging biological material such as cells, extracellular components, or tissues comprising contacting the biological material with nanoparticles comprising one or more dyes, or compositions comprising the nanoparticles; directing excitation electromagnetic (e/m) radiation, such as light, on to the tissues or cells thereby exciting the dye molecules; detecting e/m radiation emitted by the excited dye molecules; and capturing and processing the detected e/m radiation to provide one or more images of the biological material. One or more of these steps can be carried out in vitro or in vivo. For example, the cells or tissues can be present in an individual or can be present in culture. Exposure of cells or tissues to e/m radiation can be effected in vitro (e.g., under culture conditions) or can be effected in vivo. For directing e/m radiation at cells, extracellular materials, tissues, organs and the like within an individual or any portion of an individual's body that are not easily accessible, fiber optical instruments can be used.

For example, a method for imaging of a region within an individual comprises (a) administering to the individual nanoparticles or a composition of the present disclosure comprising one or more dye molecules; (b) directing excitation light into the subject, thereby exciting at least one of the one or more dye molecules; (c) detecting excited light, the detected light having been emitted by said dye molecules in the individuals as a result of excitation by the excitation light; and (d) processing signals corresponding to the detected light to provide one or more images (e.g. a real-time video stream) of the region within the subject.

Since the fluorescent particles are brighter than free dye, fluorescent particles can be used for tissue imaging, as well as to image the metastasis tumor. Additionally or alternatively, radioisotopes can be further attached to the ligand groups (e.g., tyrosine residue or chelator) of the ligand-functionalized particles or to the silica matrix of the PEGylated particles without specific ligand functionalization for photoinduced electron transfer imaging. If the radioisotopes are chosen to be therapeutic, such as, for example, $^{225}$Ac or $^{177}$Lu, this in turn would result in particles with additional radiotherapeutic properties.

For example, drug-linker conjugate, where the linker group can be specifically cleaved by enzyme or acid condition in tumor for drug release, can be covalently attached to the functional ligands on the particles for drug delivery. For example, drug-linker-thiol conjugates can be attached to maleimido-PEG-particles through thiol-maleimido conjugation reaction post the synthesis of maleimido-PEG-particles. Additionally, both drug-linker conjugate and cancer targeting peptides can be attached to the particle surface for drug delivery specifically to tumor.

The steps of the method described in the various embodiments and examples disclosed herein are sufficient to carry out the methods and produce the compositions of the present disclosure. Thus, in an embodiment, the method consists essentially of a combination of the steps of the methods disclosed herein. In another embodiment, the method consists of such steps.

In the following Statements, various examples of the methods and compositions, and methods of using the compositions of the present disclosure are described:

Statement 1. A method of forming a functionalized nanoparticle of the present disclosure comprising contacting a nanoparticle such as, for example, a silica nanoparticle or an aluminosilicate particle, (e.g, having a size (e.g., a longest dimension) of 2 to 15 nm (e.g., 10 nm or smaller, such as, for example, 2 to 10 nm or 2 to 9.99 nm)) comprising a plurality of polyethylene glycol (PEG) groups covalently bound to the surface of the nanoparticle with one or more functionalizing precursor comprising at least one reactive group, where a functionalized nanoparticle comprising at least one reactive group covalently bound to a surface of the functionalized nanoparticle is formed.

Statement 2. A method according to Statement 1, where the contacting is carried out in an aqueous medium (e.g., water).

Statement 3. A method according to Statement 1 or 2, where, if the nanoparticle is contacted with two or more functionalizing precursors (e.g., 2, 3, 4, or 5 functionalizing precursors each having at least one reactive group, wherein, at least two or all of the reactive group(s) of each individual functionalizing precursor are structurally distinct from the reactive group(s) of the other functionalizing precursor(s)), the contacting is carried out in a single reaction mixture.

Statement 4. A method according to any one of the preceding Statements, where if the nanoparticle is contacted with two or more functionalizing precursors (e.g., 2, 3, 4, or 5 functionalizing precursors each having at least one reactive group, where, at least two or all of the reactive group(s) of each individual functionalizing precursor are structurally distinct from the reactive group(s) of the other functionalizing precursor(s)), the contacting is carried out in at least two different reaction mixtures.

Statement 5. A method according to any one of the preceding Statements, further comprising contacting the functionalized nanoparticle with at least one additional functionalizing precursor comprising at least one at least two or all of the reactive group(s) of each individual functionalizing precursor are structurally distinct from the reactive group(s) of the other functionalizing precursor(s) group, where the functional group(s) of the at least one additional functionalizing precursor is/are structurally distinct from the reactive group(s) of the functionalizing precursor, and in the case where the functionalized nanoparticle is contacted with two or more additional functionalizing precursors, the reactive group(s) of each individual functionalizing precursor is/are structurally distinct from the reactive group(s) of the other functionalizing precursor(s), and a functionalized nanoparticle comprising two or more reactive groups covalently bound to a surface of the functionalized nanoparticle is formed.

Statement 6. A method according to any one of the preceding Statements, further comprising contacting the functionalized nanoparticle with one or more functional group precursor comprising one or more functional group, where a functionalized nanoparticle comprising the functional group(s) is formed and each functional group is covalently bound to the surface of the functionalized nanoparticle.

Statement 7. A method according to Statement 6, where the contacting for each functional group precursor is carried out in a single reaction mixture.

Statement 8. A method according to Statement 6, where for each contacting for an individual functional group precursor the contacting is carried out in a separate reaction mixture.

Statement 9. A method according to any one of the preceding Statements, where the nanoparticle surface functionalized with polyethylene glycol (PEG) is contacted with a first functionalizing precursor comprising at least one first reactive group, where a first functionalized nanoparticle comprising the at least one reactive group covalently bound to the surface of the functionalized nanoparticle is formed.

Statement 10. A method according to Statement 9, further comprising contacting the functionalized nanoparticle with a second functionalizing precursor comprising at least one second reactive group, where the first reactive group(s) and the second reactive group(s) are structurally distinct, where a second functionalized nanoparticle comprising the at least one first reactive group and the at least one second reactive group each covalently bound to the surface of the functionalized nanoparticle is formed.

Statement 11. A method according to Statement 10, further comprising contacting the second functionalized nanoparticle with a third functionalizing precursor comprising at least one third reactive group, wherein the first reactive group(s), second reactive group(s), and the third reactive groups(s) are structurally distinct from each other, where a third functionalized nanoparticle comprising the at least one first reactive group, the at least one second reactive group, and the at least one third reactive group each covalently bound to the surface of the functionalized nanoparticle is formed.

Statement 12. A method according to Statement 11, further comprising contacting the third functionalized nanoparticle with a third functionalizing precursor comprising at least one third reactive group, wherein the first reactive group(s), the second reactive group(s), and the third reactive groups(s) are structurally distinct from each other, where a third functionalized nanoparticle comprising the at least one first reactive group, the at least one second reactive group, and at least one third reactive group each covalently bound to the surface of the functionalized nanoparticle is formed.

Statement 13. A method according to Statement 12, further comprising contacting the third functionalized nanoparticle with a fourth functionalizing precursor comprising at least one fourth reactive group, wherein the first reactive group(s), the second reactive group(s), the third reactive groups(s), and the fourth reactive group(s) are structurally distinct from each other, where a fourth functionalized nanoparticle comprising the at least one first reactive group, the at least one second reactive group, and the at least one third reactive group, and the at least one fourth reactive group each covalently bound to the surface of the functionalized nanoparticle is formed.

Statement 14. A method according to Statement 13, further comprising contacting the fourth functionalized nanoparticle with a fifth functionalizing precursor comprising at least one fifth reactive group, wherein the first reactive group(s), the second reactive group(s), the third reactive groups(s), the fourth reactive group(s), and fifth reactive group(s) are structurally distinct from each other, where a fifth functionalized nanoparticle comprising the at least one first reactive group, the at least one second reactive group, and the at least one third reactive group, the at least one fourth reactive group, and the at least one fifth reactive group each covalently bound to the surface of the functionalized nanoparticle is formed.

Statement 15. A method according to any one of Statements 9-14, further comprising contacting the functionalized nanoparticle with one or more functional group precursor (e.g., a first functional group precursor, a second functional group precursor, a third functional group precursor, a fourth functional group precursor, a fifth functional group precursor, or a combination thereof) comprising one or more functional group, where a functionalized nanoparticle comprising the functional group(s) is formed and each functional group is covalently bound to the surface of the functionalized nanoparticle.

Statement 16. A method according to Statement 15, wherein the contacting for each functional group precuror is carried out in a single reaction mixture.

Statement 17. A method according to Statement 15, wherein for each contacting for an individual functional group precursor the contacting is carried out in a separate reaction mixture.

Statement 18. A method according to any one of the preceding Statements, where the functionalizing precursor comprises a reactive group chosen from an amine group, a thiol group, a carboxylic acid group, a carboxylate group, an ester group (e.g., an activated ester group), a maleimide group, an allyl group, a terminal alkyne group, an azide group, a thiocyanate group, and combinations thereof.

Statement 19. A method according to any one of the preceding Statements, where the functionalizing group precursor comprises one or more silane group and one or more reactive group.

Statement 20. A method according to any one of the preceding Statements, where the silane group is chosen from the following:

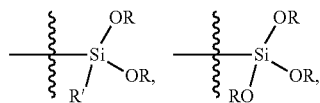

and combinations thereof, where R is, independently at each occurance, an alkyl group (e.g., a $C_1$, $C_2$, $C_3$, or $C_4$ alkyl group) and R is, independently at each occurance, a H or an alkyl group (e.g a $C_1$, $C_2$, $C_3$, or $C_4$ alkyl group).

Statement 21. A method according to any one of the preceding Statements, where one or more of the functionalizing precursors has the following structure:

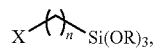

where X is a reactive group described herein (e.g., an amine group, a thiol group, a carboxylic acid group, a carboxylate group, an ester group (e.g., an activated ester group), a maleimide group, an allyl group, a terminal alkyne group, an azide group, or a thiocyanate group), n is, for example, 1, 2, 3, 4, 5, 6, 7, or 8, and R is, independently at each occurance, an alkyl group (e.g., a a $C_1$, $C_2$, $C_3$, or $C_4$ alkyl group).

Statement 22. A method according to any one of Statements 6-8 and 15-20, where at least one functional group or all of the functional groups is/are covalently bound to the surface of the nanoparticle through a linker group.

Statement 23. A method according to Statement 22, where the linker group at each individual instance is chosen from alkyl groups (e.g., $C_1$, $C_2$, $C_3$, or $C_4$ alkyl groups).

Statement 24. A method according to any one of Statements 6-8 and 15-20, where the functional group(s) is/are chosen from functional groups described herein and combinations thereof.

Statement 25. A composition comprising a plurality of nanoparticles described herein (e.g., a plurality of nanoparticles, each nanoparticle comprising a plurality of polyethylene glycol (PEG) groups covalently bound to the surface of the nanoparticle and at least one functional group (e.g., 1, 2, 3, 4, or 5 different types of functional groups) covalently bound to a surface of the functionalized nanoparticle), where at least 95% (e.g., at least 96%, at least 97%, at least 98%, at least 99%, or 100%) of the nanoparticles have a size described herein (e.g., a size of 2 to 15 nm (e.g., 10 nm or smaller, such as, for example, 2-8 or 2-7 nm), or 2 to 10 nm or 2 to 9.99 nm)) and the composition has not been subjected to any particle-size discriminating processes.

Statement 26. A composition according to Statement 25, where the nanoparticles are core nanoparticles (e.g., having a size (e.g., longest dimension) of 2 to 15 nm (e.g., 10 nm or smaller, such as, for example, 2 to 10 nm or 2 to 9.99 nm), core-shell nanoparticles (e.g., having a size (e.g., longest dimension) of 2 to 15 nm (e.g., 10 nm or smaller, such as, for example, 2 to 10 nm or 2 to 9.99 nm), or a combination thereof.

Statement 27. A composition according to Statement 26, where the core nanoparticles are aluminosilicate core nanoparticles or a silica core nanoparticles.

Statement 28. A composition according to Statement 26 or 27, where the core is a silica core or the core and shell of the core-shell nanoparticles is a silica shell.

Statement 29. A composition according to any one of Statements 26-28, where the core of the core shell nanoparticles is an aluminosilicate core and the shell of the core-shell nanoparticles is a silica shell.

Statement 30. A composition according to any one of Statements 25-29, where the functional group(s) is/are chosen from functional groups described herein and combinations thereof.

Statement 31. A method according to any one of Statements 25-30, where at least one or all of the functional group(s) is/are covalently bound to the surface of the nanoparticle through a linker group.

Statement 32. A method according to Statement 31, where the linker group at each individual instance is chosen from alkyl groups (e.g., $C_1$ to $C_4$ alkyl groups).

Statement 33. A composition according to any one of Statements 25-32, where 1 to 100 (e.g., 20 to 100, 25 to 100, 30 to 100, 35 to 100, 40 to 100, or 50 to 100) functional group(s) (e.g., an average of 1 to 100 functional group(s)) are covalently bound to the surface of each of the nanoparticles.

Statement 34. A composition according to any one of Statements 25-33, where at least a portion of or all of the polyethylene groups comprise one or more functional group.

Statement 35. A method according to Statement 34, where the functional group(s) is/are chosen from functional groups described herein and combinations thereof.

Statement 36. A composition according to any one of Statements 25-35, where the nanoparticles further comprise one or more dye molecule described herein or a combination thereof encapsulated therein.

Statement 37. A composition according to Statement 36, wherein the number of dye molecules per core is 1 to 7.

Statement 38. A composition according to any one of Statements 25-37, where the composition is stable (e.g., where no aggregation and/or decomposition (e.g., loss of functional groups) is observed, for example, by gel-permeation chromatography (GPC) or a combination of fluorescence correlation spectroscopy (FCS) and GPC) (e.g., for at least 1, 2, 3, 4, 5, 6, 7, 8, 9, 10, 11, 12, 18, or 24 months).

Statement 39. A diagnostic method (e.g., an imaging method) disclosed herein using a composition according to any of Statements 25-38 (e.g., a method for imaging of a region within an individual disclosed herein comprising administering to the individual the composition according to any one of Statements 25-38, wherein the nanoparticles comprise one or more dye molecules and/or one or more dye groups; directing excitation electromagnetic radiation into the subject, thereby exciting at least one of the one or more dye molecules and/or one or more dye groups; detecting excited electromagnetic radiation, the detected electromagnetic radiation having been emitted by the dye molecule(s) in the individuals as a result of excitation by the excitation electromagnetic radiation; and processing signals corresponding to the detected electromagnetic radiation to provide one or more images of the region within the subject).

Statement 40. A therapeutic method (e.g., a method of delivering a drug to an individual) disclosed herein using a composition according to any one of Statements 25-38 comprising one or more nanoparticle with functional groups comprising a drug or functional groups derived from a drug (e.g., a method for delivering a drug to an individual disclosed herein comprising administering to the individual the composition according to any one of Statements 25-38 comprising one or more nanoparticle with functional groups comprising a drug or functional groups derived from a drug, where the drug is released within the individual.

Statement 41. A therapeutic method according to Statement 40, the method further comprising imaging of a region within the individual disclosed herein (e.g., a method according to Statement 39).

The following Examples are presented to illustrate the present disclosure. They are not intended to limiting in any matter.

Example 1

This example provides examples of methods and compositions of the present disclosure and uses of same.

Multifunctional nanoparticles (NPs) combining different functional components into a single NP platform are of great interest in the fields of nanobiotechnology and nanomedicine. In this example, we describe a versatile surface modification approach to modularly and orthogonally functionalize Cornell prime dots (C' dots), ultrasmall sub-10 nm PEGylated fluorescent core-shell silica nanoparticles, with up to four types of different functional ligands on the NP surface. It enables the synthesis of penta-functional C' dots integrating a variety of properties into a single NP, i.e. fluorescence detection, specific cell targeting, radioisotope chelating/labeling, ratiometric pH sensing, and drug delivery, while the overall NP size remains below 7 nm. This is achieved by taking advantage of the fact that the PEG layer of C' dots is penetrable to small molecules. Amine- and/or thiol-functionalized silane molecules can be inserted between PEG chains and onto the silica surface of C' dots, to which additional functional ligands can subsequently be attached. This post-PEGylation surface modification by insertion (PPSMI) approach only requires a few extra steps that occur between C' dot PEGylation and purification in the one-pot type water-based synthesis without diminishing high quality NP generation. The resulting C' dots with additional functionalities exhibit physico-chemical properties like their size and PEG density close to clinically translated C dots, opening a gate to the diversification of their clinical applications. We further demonstrate a modification of the C' dot synthesis enabling large numbers of targeting peptides per particle, as well as a facile and versatile spectroscopic approach to quantitatively assess the specific numbers of the different surface ligands by deconvolution of absorption spectra into individual components. Insights gained from this study of synthetic PEGylation and post-PEGylation surface modification methods may be transferred to the development of other PEGylated NP platforms for biomedical applications and clinical translation.

In this example, we describe a modular and orthogonal post-PEGylation surface modification by insertion (PPSMI) method that achieves this goal (FIG. 1). It consists of covalently inserting silanes with orthogonal functional groups, e.g. amines and thiols, between the PEG chains and onto the silica surface of C' dots in a synthesis step that occurs between NP PEGylation and purification (FIG. 1). We demonstrate that in this way limitations of existing functionalization strategies can be overcome, including particle aggregation observed when these groups are introduced during PEGylation. The PPSMI method preserves the one-pot nature of the C' dot synthesis in aqueous media. Furthermore, we will show that these modular and orthogonal surface modification reactions have only minor effects on the overall physicochemical properties of the particles including size and PEG density, thereby maximizing chances for their clinical translation. Using this approach, a variety of multifunctional C' dots can be produced (Table 1). In particular, a penta-functional C' dot particle with a total of four functional ligands attached to the NP surface is synthesized enabling simultaneous fluorescence tracing, tumor targeting, ratiometric pH sensing, radioisotope chelating and disease treatment (FIG. 1). This surface modification approach takes advantage of the fact that the PEG layer of well-PEGylated NPs is still penetrable by other molecules. In order to properly account for the chemical complexity of such particles, and to distinguish different multifunctional NP chemistries from one another, we develop a nomenclature system containing information on (i) NP platform, e.g. C' dots versus mesoporous C dots (mC dots), (ii) encapsulated fluorescent dye, (iii) specific surface functionality and its connectivity to the particle, (iv) specific attachment chemistry, (v) specific PEG chain length, and more (e.g., FIG. 7). We finally demonstrate a spectroscopic approach to quantitatively assess the specific numbers of different ligands introduced to the particle surface by deconvolution of absorption spectra into individual components. We expect that insights gained in this study may also provide pathways to the development of other PEGylated NP platforms for biomedical applications.

TABLE 1

Summary of the characterization results of all synthesized C' dots with different functionalities

| C' dot products | Complete nomenclature | Additions in core formation | Additions in PEGylation | Additions in Post-PEGylation surface modification | Hydrodynamic size | #of functional ligand per NP |
|---|---|---|---|---|---|---|
| c(RGDyC)-PEG-Cy5.5-C' dots | C'Dot(Cy5.5)-PEG12-mal-thiol-c(RGDyC)_PEG6 | Cy5.5 | c(RGDyC)-PEG-silane PEG-silane | NA | 6.4 nm | 1.6 Cy5.5, 24 c(RGDyC) |
| c(RGDyC)-PEG-Cy5.5-C' dots | C'Dot(Cy5.5)-PEG12-mal-thiol-c(RGDyC)_PEG6 | Cy5.5 | c(RGDyC)-PEG-silane (high concentration) PEG-silane | NA | 6.8 nm | 1.7 Cy5.5, 58 c(RGDyC) |
| c(RGDyC)-PEG-Cy5-C' dots | C'Dot(Cy5)-PEG12-mal-thiol-c(RGDyC)_PEG6 | Cy5 | c(RGDyC)-PEG-silane PEG-silane | N/A | 6.5 nm | 1.7 Cy5, 21 c(RGDyC) |
| c(RGDyC)-PEG-cw800-C' dots | C'Dot(cw800)-PEG12-mal-thiol-c(RGDyC)_PEG6 | cw800 | c(RGDyC)-PEG-silane PEG-silane | NA | 6.1 nm | 1.4 cw800, 8 c(RGDyC) |
| c(RGDyC)-mal-PEG-Cy5-C' dots | C'Dot(Cy5)-PEG12-mal-thiol-c(RGDyC)_PEGU-mal_PEG6 | Cy5 | mal-PEG-silane c(RGDyC)-PEG-silane PEG-silane | NA | 6.8 nm | 1.6 Cy5, 22 c(RGDyC), NA mal |
| c(RGDyC)-DFO-PEG-Cy5-C' dots | C'Dot(Cy5)-PEG12-mal-thiol-c(RGDyC)_amine-NCS-DFO-PEG6 | Cy5 | DFO-PEG-silane c(RGDyC)-PEG-silane PEG Silane | NA | 6.4 nm | 1.7 Cy5, 21 c(RGDyC), 2 DFO |
| c(RGDyC)-DBCO-PEG-Cy5-C' dots | C'Dot(Cy5)-PEG12-mal-thiol-c(RGDyC)_PEG4-DBCO_PEG6 | Cy5 | DBCO-PEG-silane c(RGDyC)-PEG-silane PEG-silane | NA | 6.8 nm | 1.8 Cy5, 21 c(RGDyC), 3 DBCO |
| c(RGDyC)-NH$_2$-PEG-Cy5-C' dots | C'Dot(Cy5)-amine PEG12-mal-thiol-c(RGDyC)_PEG6 | Cy5 | amine-silane c(RGDyC)-PEG-silane PEG-silane | NA | 6.8 nm | 1.9 Cy5, 22 c(RGDyC) |

TABLE 1-continued

Summary of the characterization results of all synthesized C' dots with different functionalities

| C' dot products | Complete nomenclature | Additions in core formation | Additions in PEGylation | Additions in Post-PEGylation surface modification | Hydro-dynamic size | #of functional ligand per NP |
|---|---|---|---|---|---|---|
| $NH_2$c(RGDyC)-PEG-Cy5-C' dots | C'Dot(Cy5)-PEG12-mal-thiol-c(RGDyC)_PEG6_amine | Cy5 | c(RGDyC)-PEG-silane PEG-silane | amine-silane | 6.6 nm | 1.5 Cy5, 22 c(RGDyC) |
| DFO-c(RGDyC)-PEG-Cy5-C' dots | C'Dot(Cy5)-PEG12-mal-thiol-c(RGDyC)_PEG6_amine-NCS-DFO | Cy5 | c(RGDyC)-PEG-silane PEG-silane | amine-silane DFO-NCS | 6.4 nm | 1.6 Cy5, 23 c(RGDyC), 4 DFO |
| DOTA-c(RGDyC)-PEG-Cy5-C' dots | C'Dot(Cy5)-PEG12-mal-thiol-c(RGDyC)_PEG6_anime-NCS-DOTA | Cy5 | c(RGDyC)-PEG-silane PEG-silane | amine-silane DOTA-NCS | 6.5 nm | 1.6 Cy5, 21 c(RGDyC), 6 DOTA |
| SH-PEG-Cy5-C' dots | C'Dot(Cy5)-PEG6_thiol | Cy5 | PEG-silane | thiol-silane | 6.6 nm | 1.6Cy5 |
| FITC-PEG-Cy5-C' dots | C'Dot(Cy5)-PEG6_thiol-mal-FITC | Cy5 | PEG-silane | thiol-silane FITC-mal | 6.7 nm | 1.6Cy5, 6 FITC |
| FITC-DFO-c(RGDyC)-PEG-Cy5-C' dots | C'Dot(Q5)-PEG12-mal-thiol-c(RGDyC)_PEG6_amine-NCS-DFOthiol-mal-FITC | Cy5 | c(RGDyC)-PEG-silane PEG-silane | amine-silane DFO-NCS thiol-silane FITC-mal | 6.8 nm | 1.7 Cy5, 23c(RGDyC), 19 DFO, 4 FITC |
| FITC-DFO-EFV-c(RGDyC)-PEG-Cy5-C' dots | C'Dot(Q5)-PEG12-mal-thiol-c(RGDyC) PEG12-mal-thiol-PEGl0-E'EP_PEG6_amine-NCS-DFO thiol-mal-FITC | Cy5 | c(RGDyC)-PEG-silane mal-PEG-silane PEG-silane | EFV-PEG-thiol amine-silane DFO-NCS thiol-silane FITC-mal | 6.9 nm | 1.9 Cy5, 25 c(RGDyC), 3 DFO, 4 FITC, 25 EFV |

Figure 8:
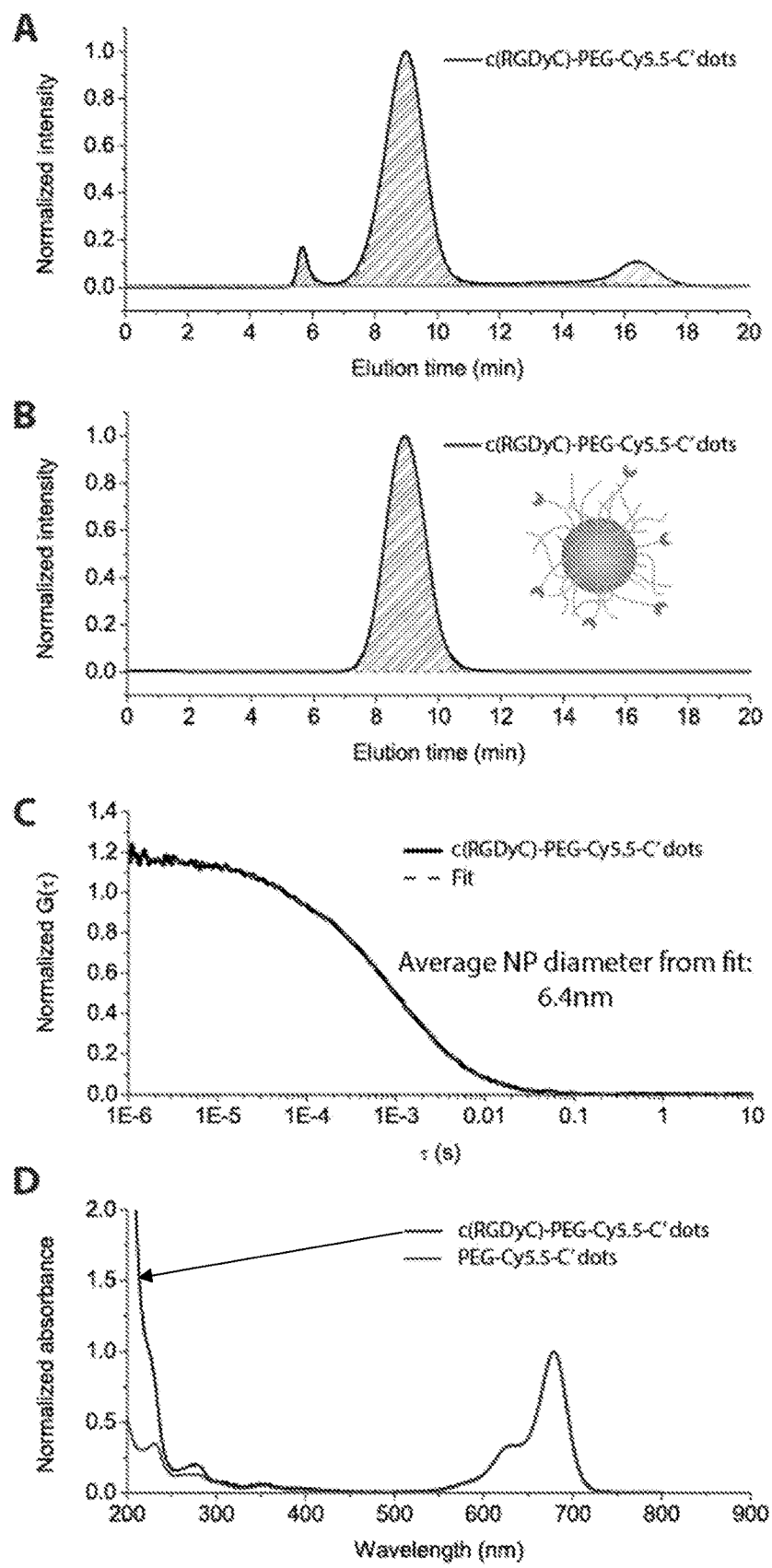
FIG. 8 shows cancer targeting c(RGDyC)-PEG-C' dots functionalized with different NIR dyes. (A and B) GPC elugram before (A) and after (B) purification of c(RGDyC)-PEG-Cy5.5-C' dots with encapsulated Cy5.5 dye. (C) FCS correlation curve and fit of purified c(RGDyC)-PEG-Cy5.5-C' dots. (D) Comparison of UV-vis absorbance of PEG-Cy5.5-C' dots with and without c(RGDyC) functionalization. (E and F) GPC elugram before (E) and after (F) NP purification of c(RGDyC)-PEG-Cy5-C' dots with encapsulated Cy5 dye. (G) FCS correlation curve and fit of purified c(RGDyC)-PEG-Cy5-C' dots. (H) Comparison of UV-vis absorbance of PEG-Cy5-C' dots with and without c(RGDyC) functionalization. (I and J) GPC elugram before (I) and after (J) NP purification of c(RGDyC)-PEG-CW800-C' dots with encapsulated CW800 dye. (K) FCS correlation curve and fit of purified cRGDY-PEG-CW800-C' dots. (L) Comparison of UV-vis absorbance of PEG-CW800-C' dots with and without c(RGDyC) functionalization. The different absorbance peaks at around 655 nm (D), 657 nm (H) and 795 nm (L) indicate the successful encapsulation of different types of NIR dyes.
Figure 8:
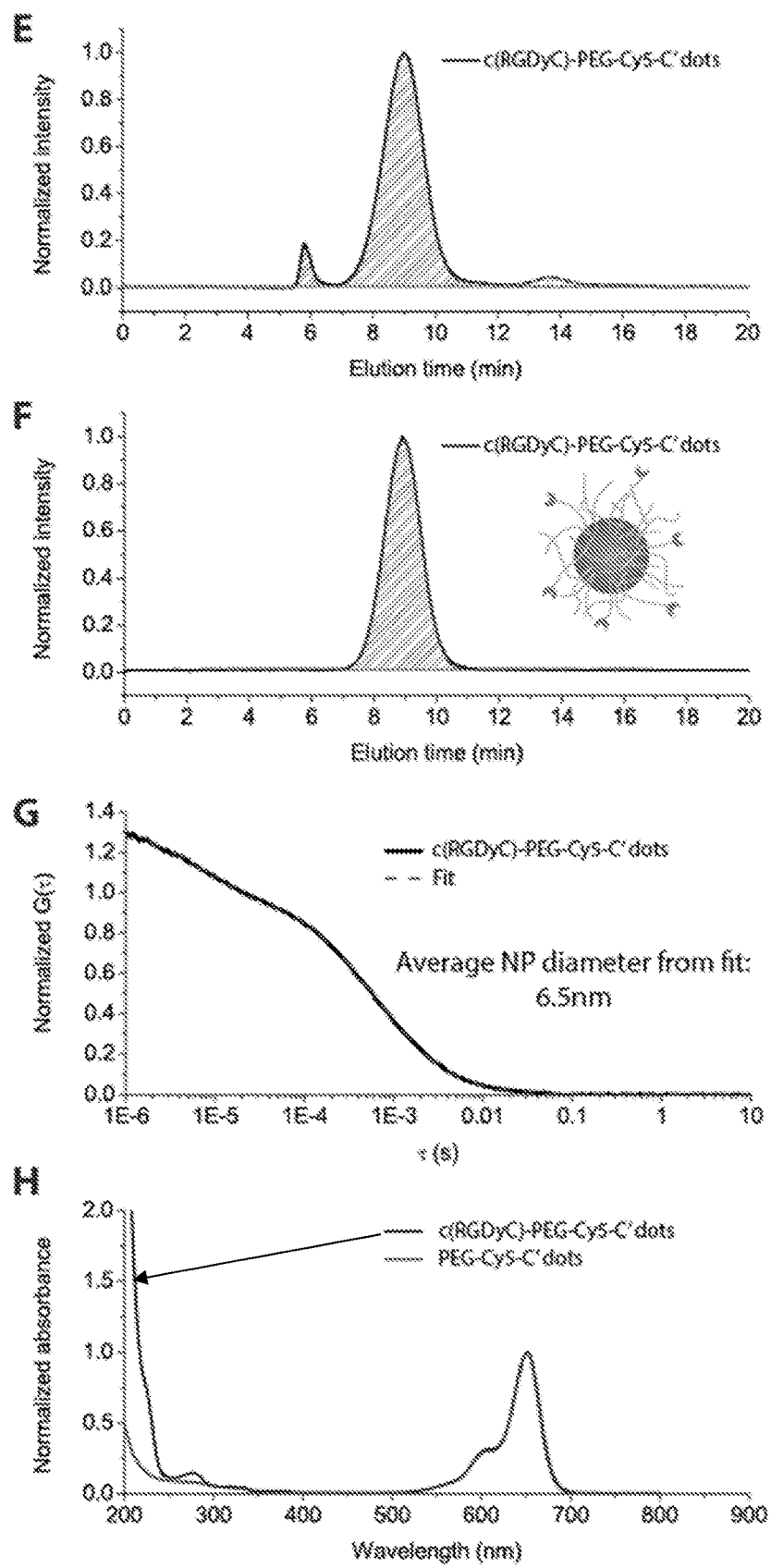
Figure 8:
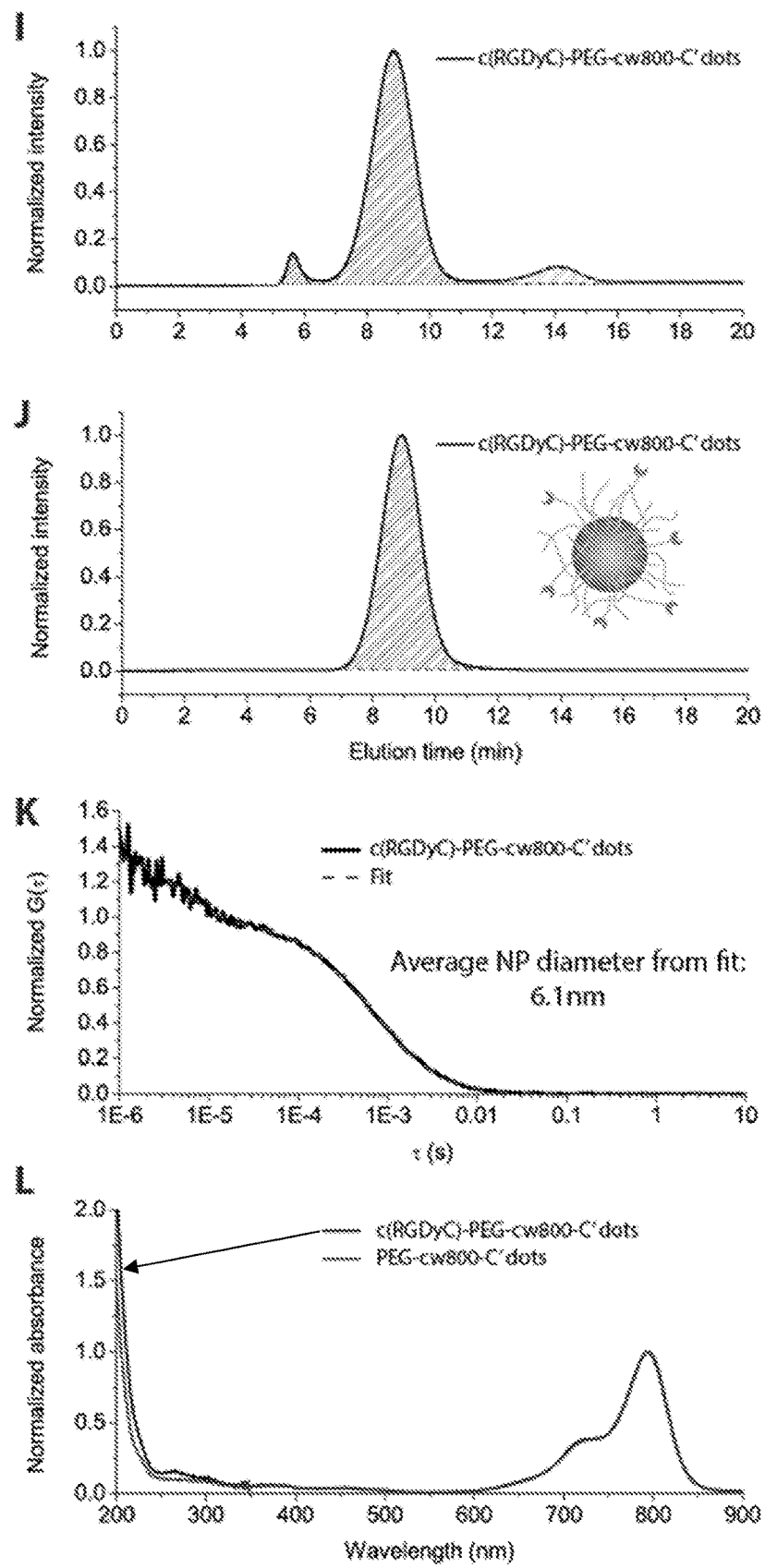

Results and Discussions. Synthesis and purification of c(RGDyC)-PEG-Cy5.5-C' dots. The previously reported synthesis of C' dots is a versatile approach enabling the functionalization of C' dots with different types of dyes and cancer targeting peptides (FIG. 8). For example, to produce C' dots functionalized with NIR dye Cy5.5 and $\alpha_v\beta_3$ integrin-targeting cyclic (arginine-glycine-aspartic acid-D-tyrosine-cysteine) peptides (c(RGDyC)), referred to as c(RGDyC)-PEG-Cy5.5-C' dots, tetramethyl orthosilicate (TMOS) and Cy5.5 silane conjugate (Cy5.5-silane) were first added into aqueous ammonium hydroxide solution at pH around 8 at room temperature. The hydrolyzed TMOS and Cy5.5-silane molecules condense together forming ultrasmall silica NPs with Cy5.5 dyes covalently encapsulated in the silica matrix. In the next step, silane functionalized PEG (PEG-silane) and c(RGDyC) peptide modified PEG-silane (c(RGDyC)-PEG-silane) were added together into the reaction mixture. Upon addition, c(RGDyC)-PEG-silane and PEG-silane are quickly adsorbed on the NP surfaces via hydrogen bonding between surface silanol groups and PEGs thereby terminating nanoparticle growth. After leaving the reaction mixture at room temperature overnight, the reaction temperature was increased to 80° C. where it was maintained overnight to enhance the covalent attachment of PEG-silane and c(RGDyC)-PEG-silane to the NP surface. The reaction mixture was then cooled down to room temperature and the c(RGDyC)-Cy5.5-C dots were finally purified using gel permeation chromatography (GPC) and subsequently filtered by means of sterile filters for final use.

Figure 2:
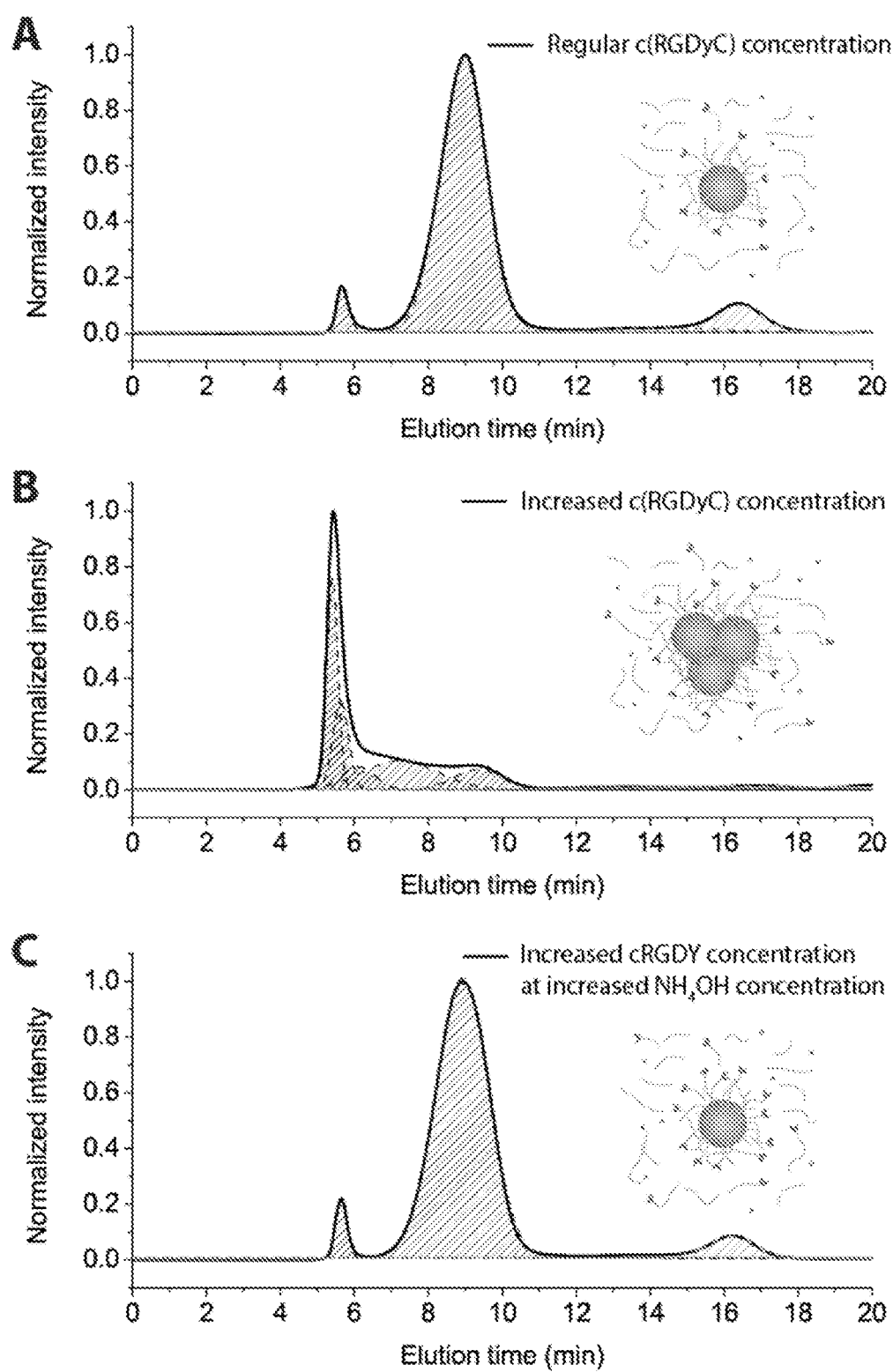
FIG. 2 shows c(RGDyC)-PEG-Cy5.5-C' dots with increased number of c(RGDyC) peptides per NP. (A to C) GPC elugrams of as synthesized c(RGDyC)-PEG-Cy5.5-C' dots, produced either using the standard C' dot synthesis protocol (A), or at increased c(RGDyC)-PEG-silane concentration (B), or at increased concentrations of both c(RGDyC)-PEG-silane and ammonium hydroxide (C). (D and E) GPC elugram (D) and FCS correlation curve (E) of the purified c(RGDyC)-PEG-Cy5.5-C' dots containing on average 58 c(RGDyC) peptides per particle. (F) Comparison of UV-vis absorbance spectra of c(RGDyC)-PEG-Cy5.5-C' dots with varying numbers of cRGDY ligands per NP as indicated in the inset.
Figure 2:
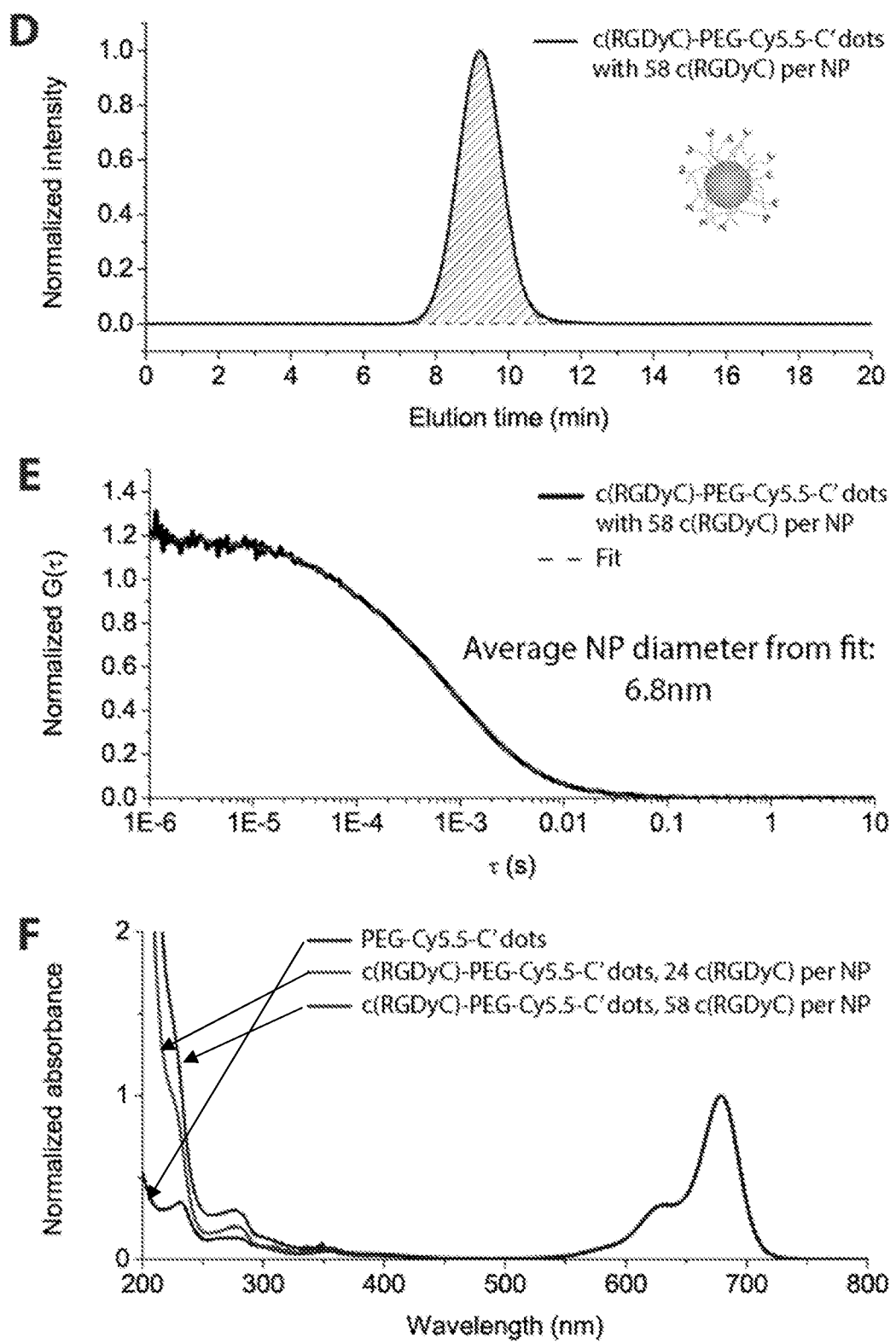

The GPC elugram of c(RGDyC)-PEG-Cy5.5-C' dots showed three peaks before purification (FIG. 2A and FIG. 8A). The main peak at about 9 min corresponded to c(RGDyC)-PEG-Cy5.5-C' dot nanoparticle product, while the peaks at about 5 min and 16 min corresponded to impurities from PEG reagents and unreacted Cy5.5-silane, respectively. The elution volume corresponding to the nanoparticle product was collected and run again over the GPC column to assure the highest possible purity. After GPC purification, the elugram of the final C' dot solution showed only a single peak at around 9 min indicating a GPC purity of about 100% (FIG. 8B). Furthermore, the product peak exhibited a narrow and highly symmetric shape without detectable skewness, and could be fitted using a single-component Gaussian distribution, indicating narrow size dispersity of the NP product.

The purified c(RGDyC)-PEG-Cy5.5-C' dots were then subjected to absorbance and fluorescence correlation spectroscopy (FCS) characterizations. The absorbance spectrum of c(RGDyC)-PEG-Cy5.5-C' dots showed a peak at around 675 nm corresponding to Cy5.5 dye and a small peak at around 275 nm (FIG. 8D) that was missing for PEGylated Cy5.5-C' dots without c(RGDyC) functionalization (PEG-Cy5.5-C' dots). The existence of this peak is therefore characteristic for c(RGDyC) peptides demonstrating the successful attachment of c(RGDyC) to the C' dot surface. The FCS curve of c(RGDyC)-PEG-Cy5.5-C' dots was well fitted using a single-modal FCS correlation function confirming the narrow size dispersity of the NP product (FIG. 8C). From the FCS fit, the hydrodynamic particle diameter and particle concentration can be determined. The numbers of Cy5.5 dyes and c(RGDyC) ligands per C dot were estimated by dividing the concentrations of Cy5.5 and c(RGDyC) obtained from absorbance measurements by the particle concentration obtained from FCS, respectively. The results indicated that the c(RGDyC)-PEG-Cy5.5-C' dots had an average diameter of about 6.4 nm and that there were about 1.6 Cy5.5 dyes and 24 c(RGDyC) peptides per NP (Table 1). Finally, a combination of FCS and absorbance measurements also allows estimation of particle brightness which suggest that the c(RGDyC)-PEG-Cy5.5-C' dots were about three times brighter than a free Cy5.5 dye in aqueous solution under the excitation condition of the FCS setup. The final c(RGDyC)-PEG-Cy5.5-C' dot product was stored in deionized (DI) water at 4° C. before further use.

Increasing c(RGDyC) surface ligand density via tuning PEGylation conditions. In the previously reported synthesis approach of clinically translated C' dots, c(RGDyC) cancer targeting peptides were introduced via the condensation of both c(RGDyC)-PEG-silane and PEG-silane onto the NP surface during the PEGylation step. Considering c(RGDyC)-PEG-silane is much more expensive than PEG-silane, c(RGDyC)-PEG-silane is always added into the reaction mixture before the addition of PEG-silane, allowing reaction with the pristine NP surface to achieve a desired conversion efficiency. Although this approach can be used to produce C' dots with up to around 20-25 c(RGDyC) ligands per NP, we observed that further increasing the concentration of c(RGDyC)-PEG-silane does not yield narrowly dispersed C' dots. Instead, the synthesis mixture immediately turns cloudy upon the addition of c(RGDyC)-PEG-silane at these higher concentrations indicating NP aggregation. Indeed, the GPC elugram of the reaction product shows broad peaks between 5 and 11 min attributed to NP aggregation (FIG. 2B). Even after numerous cycles of GPC purification, the GPC elugram of the NP product remains broadly distributed suggesting failure of the synthesis.

We found that the amount of c(RGDyC)-PEG-silane acceptable in the synthesis without causing NP aggregation is highly sensitive to the concentration of ammonium hydroxide, [$NH_3OH$]. If [$NH_3OH$] is increased from the standard 2 mM to 6 mM, the concentration of c(RGDyC)-PEG-silane can be increased up to a factor of three, while maintaining good NP product quality. The GPC elugram of C' dots synthesized at [$NH_3OH$] of 6 mM and three-fold c(RGDyC)-PEG-silane concentration (FIG. 2C) exhibited similar characteristics as for the regular conditions (FIG. 2A). Results suggest high quality NP product allowing for separation of C' dots from other impurities using GPC as described before. After purification, narrowly dispersed c(RGDyC)-PEG-Cy5.5-C' dots with an estimated 58 ligands per NP were successfully produced (FIGS. 2D to F). Compared to the lower ligand number c(RGDyC)-PEG-Cy5.5-C' dots, as expected the absorption at 275 nm in the UV-Vis spectrum is enhanced (FIG. 2F). According to FCS characterization, these particles had also slightly increased hydrodynamic size, i.e. 6.8 nm versus 6.4 nm (FIG. 2E and Table 1), over the lower ligand number (i.e. 24 c(RGDyC)'s) particles, likely due to the increased number of c(RGDyC) per particle (FIG. 2D) as opposed to a larger silica core.

The high sensitivity to [$NH_3OH$] for successful c(RGDyC) surface functionalization is probably caused by the fast adsorption of c(RGDyC) peptides to the bare silica surface and resulting changes in the electrostatic interactions between NPs. It has been demonstrated for the C' dot synthesis that during the PEGylation step both PEGs and PEG-peptide conjugates are quickly adsorbed to the bare silica NP surface likely via hydrogen bonds. This fast PEG adsorption is being utilized in the C' dot synthesis to efficiently terminate NP growth and to improve the conversion efficiency of c(RGDyC)-PEG-silane addition. However, since each c(RGDyC) peptide contains several amine groups which carry a positive charge at the reaction pH, i.e. they are a weak base, the adsorption of c(RGDyC) peptides can effectively screen the net negative charges of bare silica NPs resulting in the loss of electrostatic stability of NPs and thereby NP aggregation. In contrast, when [$NH_3OH$] is slightly increased, the average net positive charge of c(RGDyC) peptides is reduced allowing the ultrasmall silica NPs to adsorb more c(RGDyC)-PEG-silane during PEGylation without losing NP stability. Although more systematic studies are required to corroborate this hypothesis about the mechanism, the ability to improve the surface ligand density of cancer targeting peptides by a factor of more than two may further enhance the tumor targeting efficiency of C' dots.

Introducing secondary functional groups to C' dot surfaces via co-condensing ligand-PEG-silane conjugates during PEGylation. The reaction conditions developed for functionalizing C' dot surfaces with up to 58 c(RGDyC) ligands were also applied to introduce multiple types of other functional ligands to C' dot surfaces. This was achieved via replacing c(RGDyC)-PEG-silane by a combination of different ligand-PEG-silane and/or ligand-silane conjugates during the PEGylation step. However, the quality of the multifunctional C' dots synthesized, and therefore the success using this approach greatly depended on the characteristics of the functional ligands.

Figure 9:
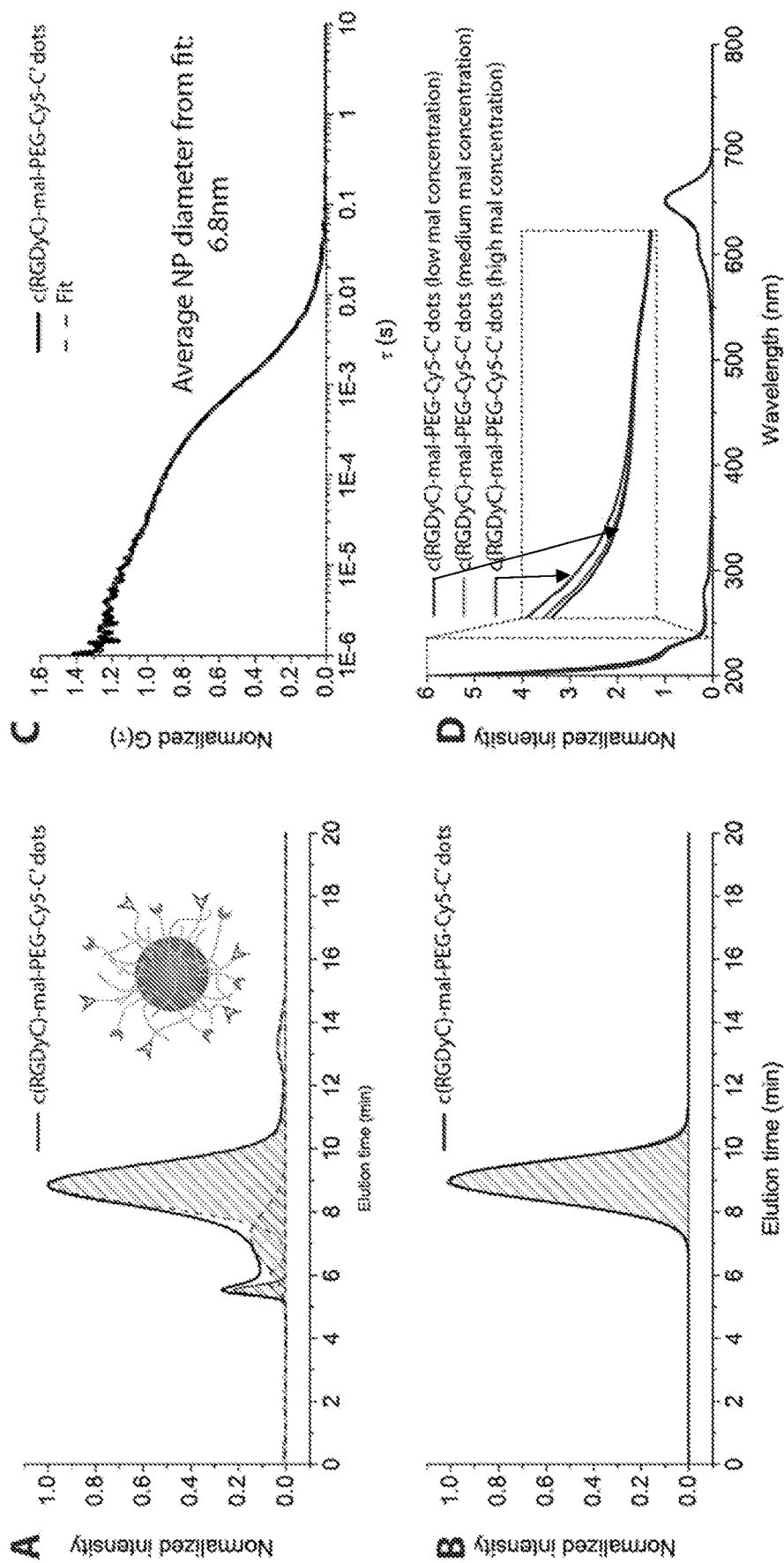
FIG. 9 shows characterization of multifunctional c(RGDyC)-mal-PEG-Cy5-C' dots prepared by introducing mal-PEG-silane during NP PEGylation. (A and B) GPC elugrams before (A) and after (B) purification. While the typical C' dot purification is conducted via two cycles of GPC runs, it requires a total of four cycles of GPC runs for the c(RGDyC)-mal-PEG-Cy5-C' dots to obtain the desired product purity as shown in (B). (C) Representative FCS correlation curve and fit of the purified c(RGDyC)-mal-PEG-Cy5-C' dots. (D) Comparison of UV-vis absorbance spectra of purified c(RGDyC)-mal-PEG-Cy5-C' dots that were synthesized using different mal-PEG-silane concentrations. The insert in (D) shows the absorption at shorter wavelengths which increases as the concentration of mal-PEG-silane is increased, which can be attributed to the increased NP loading with maleimide groups.
Figure 10:
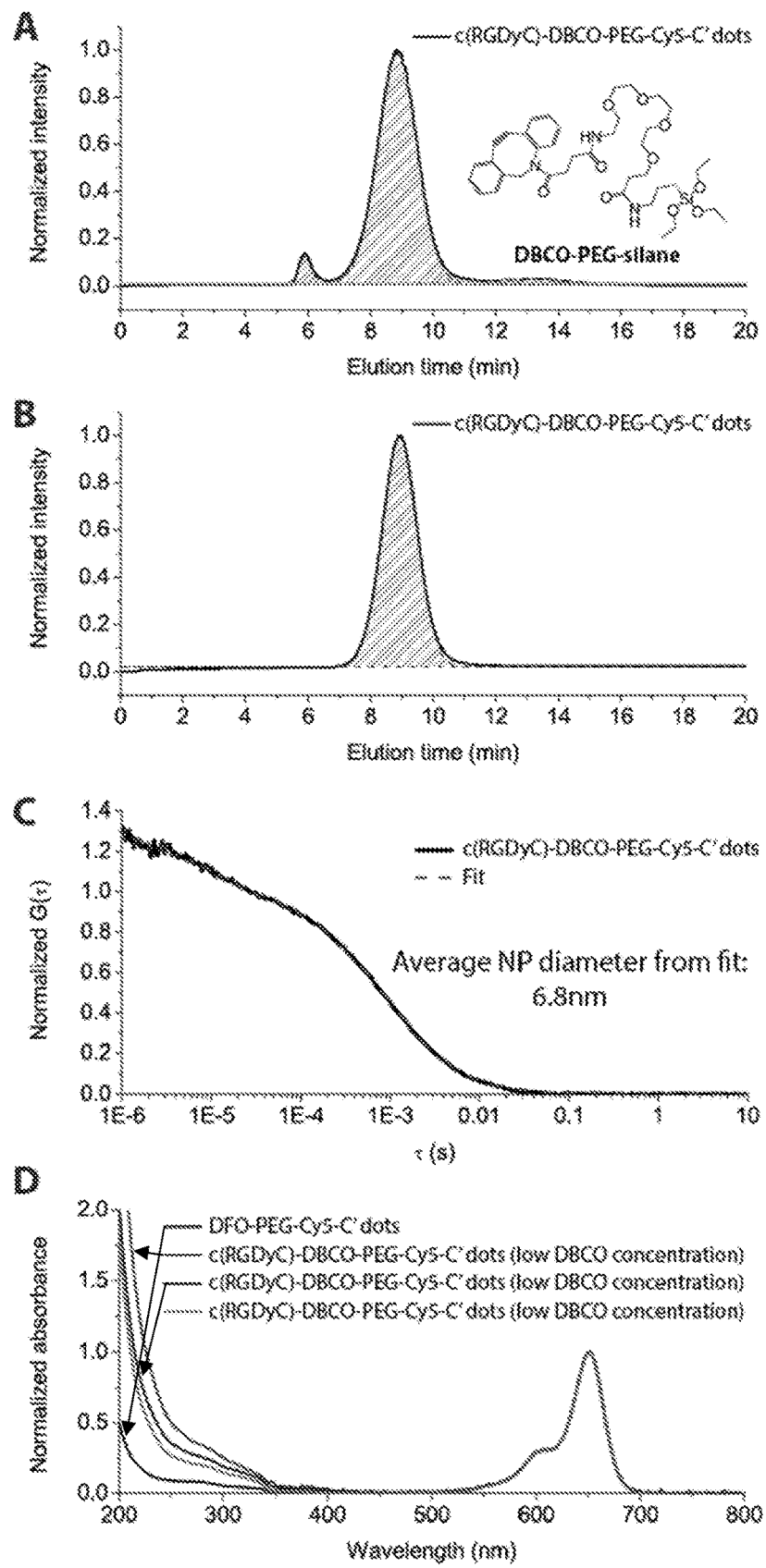
FIG. 10 shows characterization of multifunctional c(RGDyC)-DBCO-PEG-Cy5-C' dots and c(RGDyC)-DFO-PEG-Cy5-C' dots prepared by introducing DFO-silane and DBCO-PEG-silane during NP PEGylation. (A and B) GPC elugram before (A) and after (B) purification of c(RGDyC)-DBCO-PEG-Cy5-C' dots synthesized via co-condensing DBCO-PEG-silane with c(RGDyC)-PEG-silane and PEG-silane during the PEGylation step. (C) Representative FCS correlation curve and fit for purified c(RGDyC)-DBCO-PEG-Cy5-C' dots. (D) Comparison of UV-vis absorbance spectra of the purified c(RGDyC)-DBCO-PEG-Cy5-C' dots synthesized using different DBCO-PEG-silane concentrations. (E and F) GPC elugram before (E) and after (F) purification of c(RGDyC)-DFO-PEG-Cy5-C' dots synthesized via co-condensing DFO-silane with c(RGDyC)-PEG-silane and PEG-silane during the PEGylation step. (G) Representative FCS correlation curve and fit for purified c(RGDyC)-DFO-PEG-Cy5-C' dots. (H) Comparison of UV-vis absorbance spectra of the purified c(RGDyC)-DFO-PEG-Cy5-C' dots synthesized using different DFO-silane concentrations. The chemical structures of DBCO-silane and DFO-PEG-silane are shown as inserts in (A) and (E), respectively. Although monodisperse c(RGDyC)-DBCO-PEG-Cy5-C' dots and c(RGDyC)-DFO-PEG-Cy5-C' dots can be produced via this approach, the resulting NPs exhibited poor conjugation activities likely due to the limited ligand accessibility and undesired ligand distribution.
Figure 10:
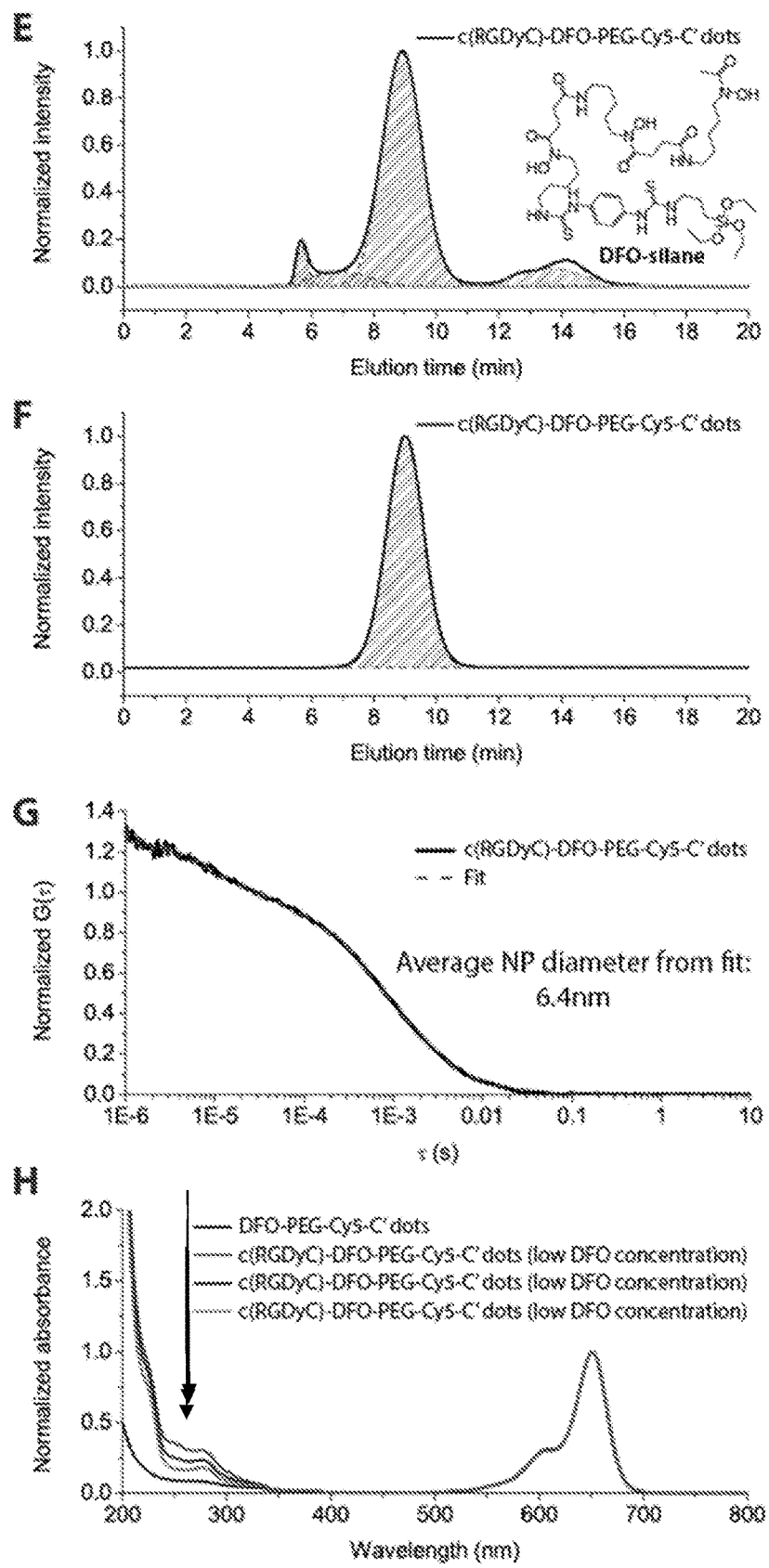

For example, a combination of c(RGDyC)-PEG-silane, maleimide (mal) functionalized PEG-silane (mal-PEG-silane) and PEG-silane was added into the reaction mixture of Cy5-based C' dots in this sequence during the PEGylation step. In addition to c(RGDyC) peptides, the resulting c(RGDyC)-mal-PEG-Cy5-C' dots contained maleimide groups on the PEGylated NP surface enabling C' dots to further react with e.g. thiol-functionalized drug-linker conjugates for theranostic applications (FIG. 1). Although the GPC elugram of as synthesized c(RGDyC)-mal-PEG-Cy5-C' dots (i.e. before GPC purification) showed a slightly skewed NP peak (FIG. 9A), a symmetric NP peak was obtained after four cycles of GPC purification together with satisfactory FCS characterization results (FIGS. 9B and C), suggesting acceptable quality of the NP synthesis product. Absorbance spectra of purified c(RGDyC)-mal-PEG-Cy5-C' dots obtained from different mal-PEG-silane concentrations showed not only a strong peak around 275 nm attributed to c(RGDyC) ligands, but also increasing absorption below 250 nm as compared to control NPs, which we attributed to the presence of maleimide functional groups (FIG. 9D). The c(RGDyC)-mal-PEG-Cy5-C' dots according to FCS had a hydrodynamic size around 6.8 nm (Table 1).

The synthesis of multifunctional C' dots may not be equally successful when other types of ligands are used. For example, maleimide groups were replaced by dibenzocyclooctyl (DBCO) groups that react with azide groups allowing for the modification of C' dots with other ligands via click chemistry. While according to GPC, UV-vis and FCS characterizations, monodisperse DBCO-c(RGDyC)-PEG-C' dots could be produced using this approach (FIGS. 10A to D, Table 1), no DBCO reactivity was observed in attempts to conjugate DBCO-c(RGDyC)-PEG-C' dots with azide-functionalizid groups. This suggests low accessibility of the DBCO ligands on C' dot surfaces. This in turn could be due to the increased hydrophobicity of DBCO ligands as compared to maleimide groups. The poor water solubility of DBCO ligands may cause them to remain associated with the silica surface of C' dots even after NP PEGylation, thereby limiting their accessibility and reactivity.

In our original trial, c(RGDyC)-PEG-Cy5-C dots were labeled with $^{124}I$ on the tyrosine residue of the c(RGDyC) peptide enabling the use of positron emission tomography (PET) imaging. In order to label C' dots with other radio-isotopes, e.g. Zirconium ($^{89}Zr$) or Lutetium ($^{177}Lu$), it is highly desirable to functionalize C' dots with specific chelator ligands. For example, deferoxamine (DFO) is one of the most efficient chelators for radio-labeling with $^{89}Zr$. In order to functionalize C' dots with DFO, isothiocyanate (NCS) functionalized DFO (NCS-DFO) was first conjugated with an amino-silane to produce DFO-silane, which was then added into the reaction mixture together with c(RGDyC)-PEG-silane and PEG-silane during PEGylation. Although narrowly dispersed DFO-c(RGDyC)-PEG-C' dots were produced through this approach (FIGS. 10E to H and Table 1), these NPs exhibited unfavorable results in biological experiments which we tentatively attributed to a heterogeneous distribution of DFO groups across different C' dots (data not shown).

Figure 3:
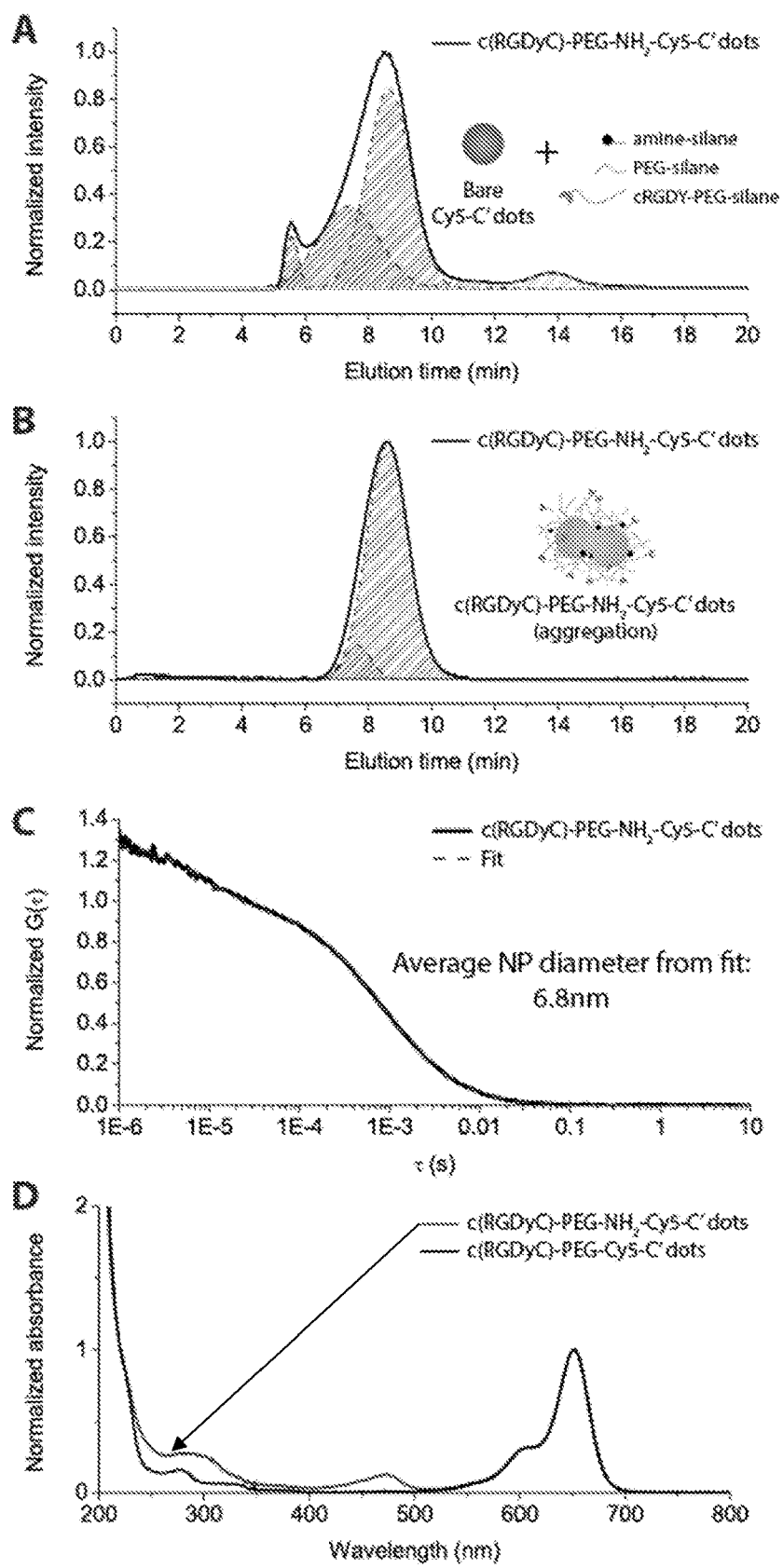
FIG. 3 shows characterization of c(RGDyC)-PEG-C' dots functionalized with amine groups during (left) or after (right) PEGylation. (A and B) GPC elugrams of c(RGDyC)-PEG-NH$_2$-Cy5-C' dots before (A) and after (B) four cycles of GPC purification, amine functionalized during the PEGylation step. (C) FCS correlation curve and fit of purified c(RGDyC)-PEG-NH$_2$-Cy5-C' dots. (D) Comparison of UV-vis spectra of c(RGDyC)-PEG-Cy5-C' dots with (red) and without (black) amine functionalization during PEGylation. (E and F) GPC elugrams of NH$_2$-cRGDY-PEG-Cy5-C' dots before (E) and after (F) purification, amine functionalized after PEGylation. (G) FCS correlation curve and fit of purified NH$_2$-cRGDY-PEG-Cy5-C' dots. (H) Comparison of UV-vis spectra of c(RGDyC)-PEG-Cy5-C' dots with (red) and without (black) amine functionalization after PEGylation step.
Figure 3:
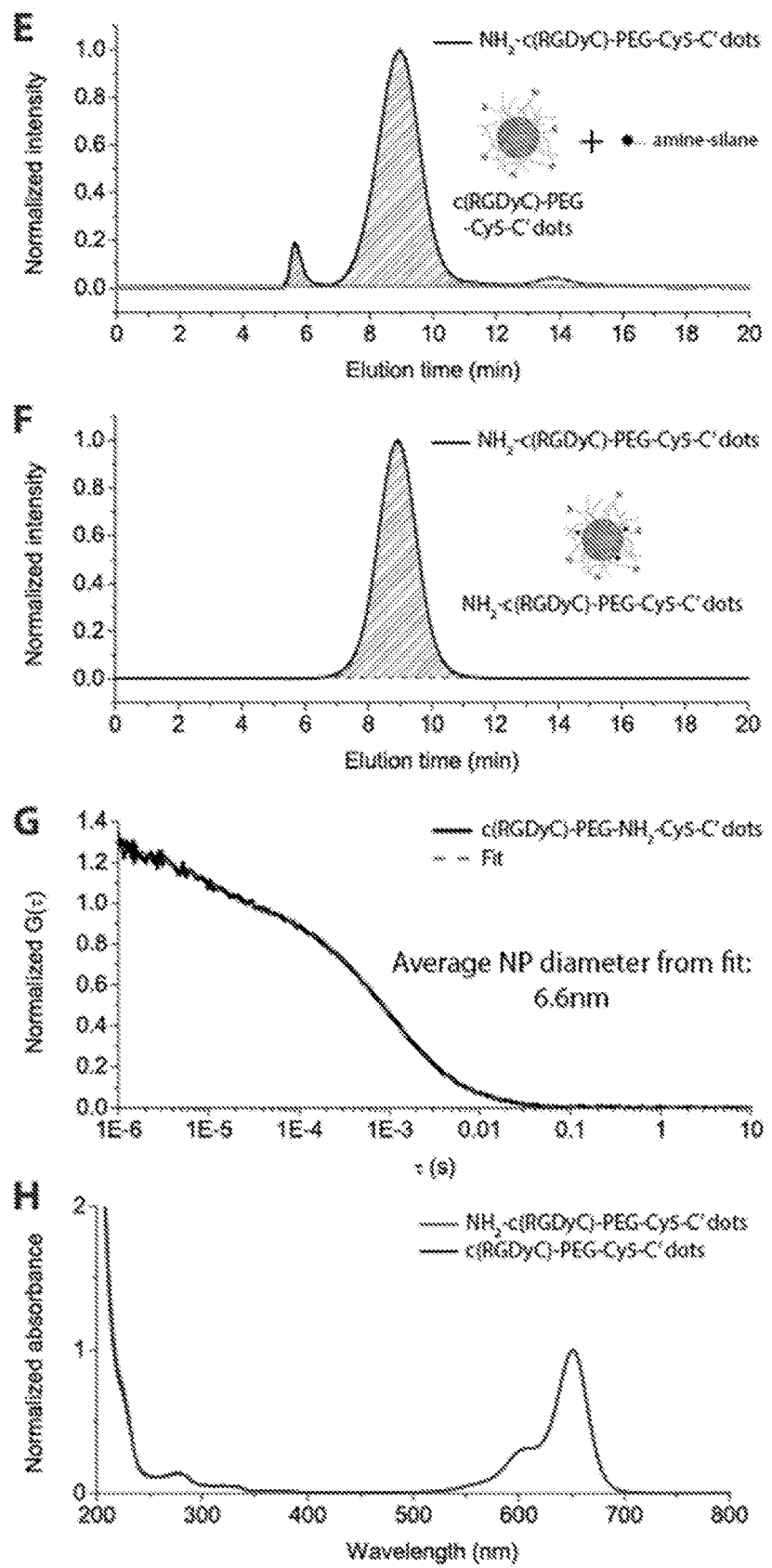

A final example is the functionalization of c(RGDyC)-PEG-C' dots with amine groups allowing for modifying C' dots with amine-reactive functional ligands. When an amino-silane like aminopropyl-trimethoxy-silane (APTMS) was introduced together with c(RGDyC)-PEG-silane and PEG-silane during PEGylation, the resulting c(RGDyC)-NH$_2$-PEG-C' dots exhibited a broadened particle peak in the GPC elugram (FIG. 3A). The peak remained skewed even after four cycles of GPC purification (FIG. 3B). The skewed GPC elugram indicates NP aggregation, which is likely caused by the attached amine groups catalyzing Si—O—Si bond formation leading to loss of NP stability. Although the average particle size remained at around 6.8 nm after GPC purification (FIG. 3C and Table 1) as suggested by FCS characterizations, this NP aggregation greatly affected both the yield and quality of the final C' dot product (FIG. 3B) since a parent aggregation peak was still observed for the purified NPs. Furthermore, the absorbance of c(RGDyC)-NH$_2$-PEG-Cy5-C' dots synthesized using this method showed an additional peak at around 480 nm as compared to the standard c(RGDyC)-PEG-Cy5-C' dots (FIG. 3D). This absorbance can be attributed to degradation products of Cy5 dyes, likely caused by the interaction between amine groups and Cy5 molecules close to the silica surface. This degradation of Cy5 dyes reduces the particle fluorescence brightness and is highly undesired for biomedical applications. Introducing secondary functional groups to C' dot surfaces via post-PEGylation surface modification by insertion (PPSMI). The challenge of introducing secondary functional groups to C' dot surfaces by co-condensing different ligand-silane conjugates during PEGylation is based on the dramatically varying affinity between different functional groups and bare silica NP surfaces. Many of the functional ligands of interest for biomedical applications carry considerable amounts of amine and/or hydroxyl groups, which have high affinity to silica. As described in the previous section, the strong association between such ligands and silica can potentially lead to their inaccessibility and heterogeneous distribution.

One possible solution to this challenge is to control the kinetics of the association between ligands and silica. In an ideal situation, it is favorable to have some degree of affinity between ligand and bare silica to enhance reaction conversion. On the other hand, too high an affinity may result in hindered ligand accessibility and heterogeneous ligand distribution. Relying on the control of the association kinetics is non-optimal for several reasons. First, the association between ligand and silica is highly sensitive to details of ligand molecular structure. It would be inefficient to optimize PEGylation conditions for every different ligand separately. Second, since bare silica NPs in water are electrostatically stabilized and their stability is highly sensitive to reaction conditions including ionic strength and pH, tuning PEGylation conditions may interfere with NP stability resulting in failed syntheses, vide supra.

In order to overcome these problems, rather than continuing to functionalize C' dots during the PEGylation step, we experimented with post-PEGylation surface modification by insertion (PPSMI) reactions. This PPSMI approach takes advantage of the well-established PEGylation protocol of C' dots. Particle PEGylation decelerates the association between additional ligands and the silica NP surface, leaving these ligands with more time to homogeneously disperse into the reaction mixture before reacting with silica NPs. Furthermore, the well-defined PEGylation endows C' dots with distinct steric stability protecting them from aggregation even under more extreme synthesis conditions. It therefore provides a wider window to tune reaction parameters for efficient surface modifications with additional ligands. Most importantly, it has recently been reported that the PEG layer of PEGylated NPs may still be penetrable by biomolecules like proteins depending on a number of parameters, including surface PEG density and NP surface curvature. Meanwhile, there are always remaining silanol groups at the interface between the silica core and the PEG layer of PEGylated silica nanoparticles even after PEGylation, potentially enabling further condensation with small silane molecules.

Figure 11:
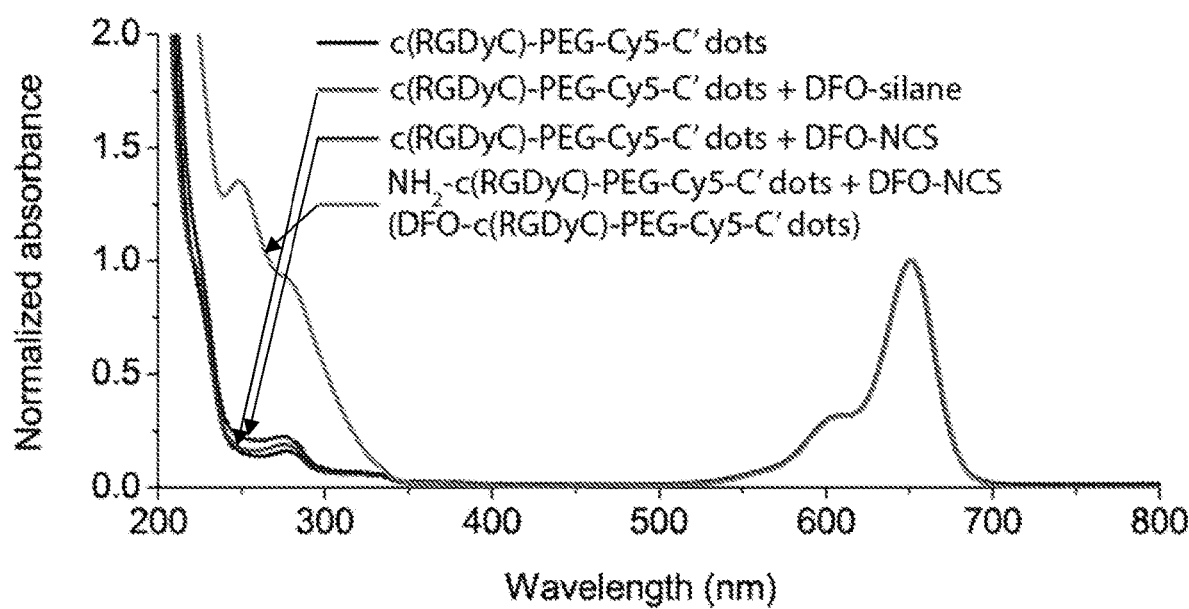
FIG. 11 shows comparison of UV-vis absorbance spectra of c(RGDyC)-PEG-Cy5-C' dots functionalized with DFO using various methods. When c(RGDyC)-PEG-Cy5-C' dots are mixed with DFO-silane conjugate, the absorbance spectrum of the resulting NPs exhibits no substantial difference as compared to that of unfunctionalized c(RGDyC)-PEG-Cy5-C' dots suggesting low reaction efficiency. Additionally, cRGDY peptide carries one primary amine group, which can potentially react with DFO-NCS. The absorbance spectrum of the reaction product of the synthesis between c(RGDyC)-PEG-Cy5-C' dots and DFO-NCS did not exhibit any additional absorption features at around 245 nm either, indicating negligible conversion yield of this DFO conjugation (results also suggest limited reactivity of the primary amine group on the c(RGDyC) peptide with DFO-NCS). The average number of DFO groups per C' dot from these experiments is below 0.5. In comparison, when DFO-NCS is mixed with amine-functionalized $NH_2$-c(RGDyC)-PEG-Cy5-C' dots derived from a post-PEGylation surface modification reaction with an amino-silane, the final C' dot product exhibits substantial absorbance below 300 nm suggesting significant DFO attachment which from calibration amounts to an average of ~20 DFO molecules per C' dot. These data suggest that the DFO groups on DFO-c(RGDyC)-PEG-Cy5-C' dots are mainly attached via the post-PEGylation introduced amine groups, instead of to the primary amine groups on the c(RGDyC) peptides.

To that end, in a first attempt we added DFO-silane into the reaction mixture of c(RGDyC)-PEG-Cy5-C' dots, i.e. after the PEGylation step. Unfortunately, the final product did not exhibit the expected increase of absorbance signal in the sub 300 nm regime, indicating low reaction efficiency with DFO-silane (FIG. 11). This could be due to a couple of reasons. First, since the DFO-silane conjugate has a molar mass even larger than PEG-silane used in the C' dot PEGylation, it may not efficiently diffuse through the PEG layer and react with the underlying silica surface silanol groups. This suggests a fairly dense PEG layer of the PEGylated C' dots consistent with our previous studies. Second, self-condensation of hydrolyzed DFO-silanes competes with their attachment to C' dots. The self-condensation may take over the reaction as the penetration of DFO-silane through the PEG layer is slow. Based on these initial results and conclusions we chose an alternative approach to functionalize c(RGDyC)-PEG-Cy5-C' dots with DFO, in which the surface modification was split into two steps (FIG. 1). In the first step, amino-silane was added into the reaction mixture. The amino-silane is a relatively small molecule and is therefore expected to diffuse faster into the PEG layer and attach to the silica surface underneath. The resulting NH$_2$-c(RGDyC)-PEG-Cy5-C' dots exhibited no substantial changes in particle characteristics as compared to the corresponding c(RGDyC)-PEG-Cy5-C' dot (Table 1, also compare FIGS. 3E to H with FIGS. 8E to H). For example, the absorbance spectra of c(RGDyC)-PEG-Cy5-C' dots and NH$_2$-c(RGDyC)-PEG-Cy5-C' dots almost perfectly overlap with each other, indicating that the attachment of amino-silane to c(RGDyC)-PEG-Cy5-C' dots does not have any effect on the optical characteristics of these particles (FIG. 3H).

Figure 4:
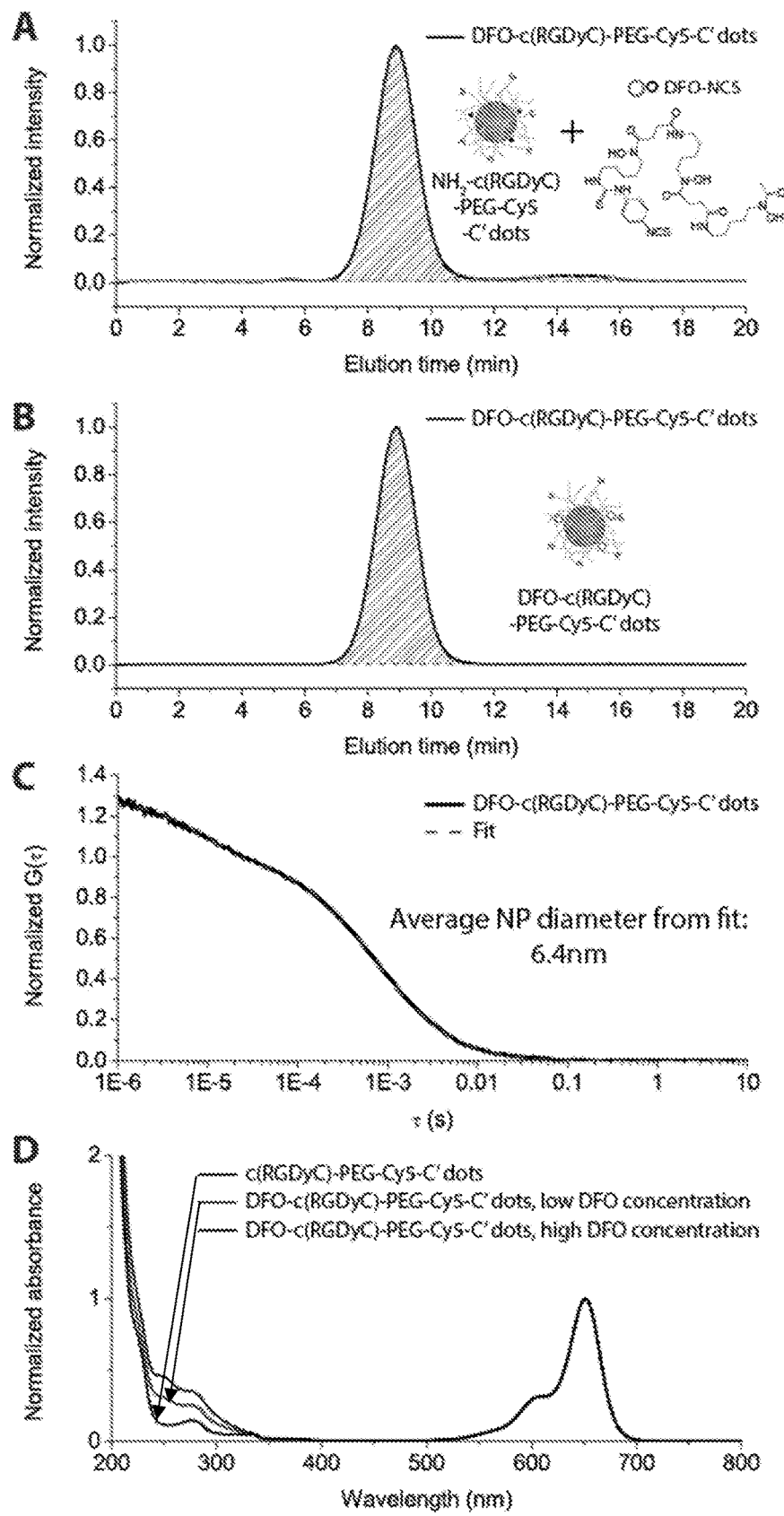
FIG. 4 shows PPSMI based surface functionalization of c(RGDyC)-PEG-C' dots with radioisotope chelators. (A and B) GPC elugrams of DFO-c(RGDyC)-PEG-Cy5-C' dots before (A) and after (B) purification, for which DFO ligands were introduced via further attaching DFO-NCS to the post PEGylation derived amine-functionalized NH$_2$-cRGDY-PEG-Cy5-C' dots during a one-pot NP synthesis. (C) FCS correlation curve and fit of the purified DFO-c(RGDyC)-PEG-Cy5-C' dots. (D) Comparison of UV-vis spectra of purified DFO-c(RGDyC)-PEG-Cy5-C' dots that were synthesized using two different DFO-NCS concentrations. (E and F) GPC elugrams of DOTA-c(RGDyC)-PEG-Cy5-C' dots before (E) and after (F) purification, for which DOTA ligands were introduced via further attaching DOTA-NCS to the post PEGylation derived amine-functionalized NH$_2$-c(RGDyC)-PEG-Cy5-C' dots during a one-pot NP synthesis. (G) FCS correlation curve and fit of the purified DOTA-c(RGDyC)-PEG-Cy5-C' dots. (H) Comparison of UV-vis spectra of purified DOTA-c(RGDyC)-PEG-Cy5-C' dots that were synthesized using two different DOTA-NCS concentrations. The chemical structures of DFO-NCS and DOTA-NCS chelators are shown as inserts in (A) and (E), respectively.
Figure 4:
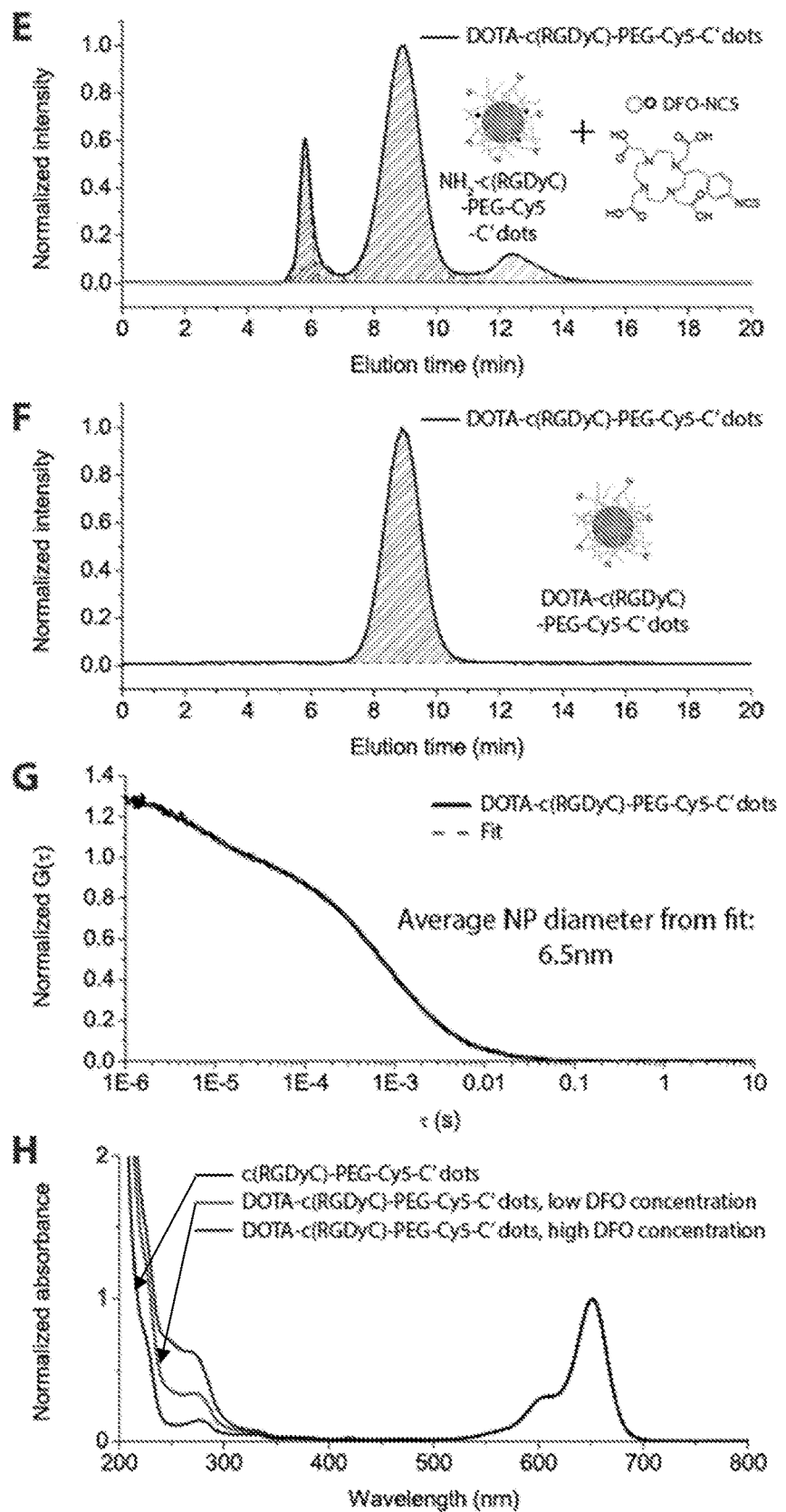
Figure 12:
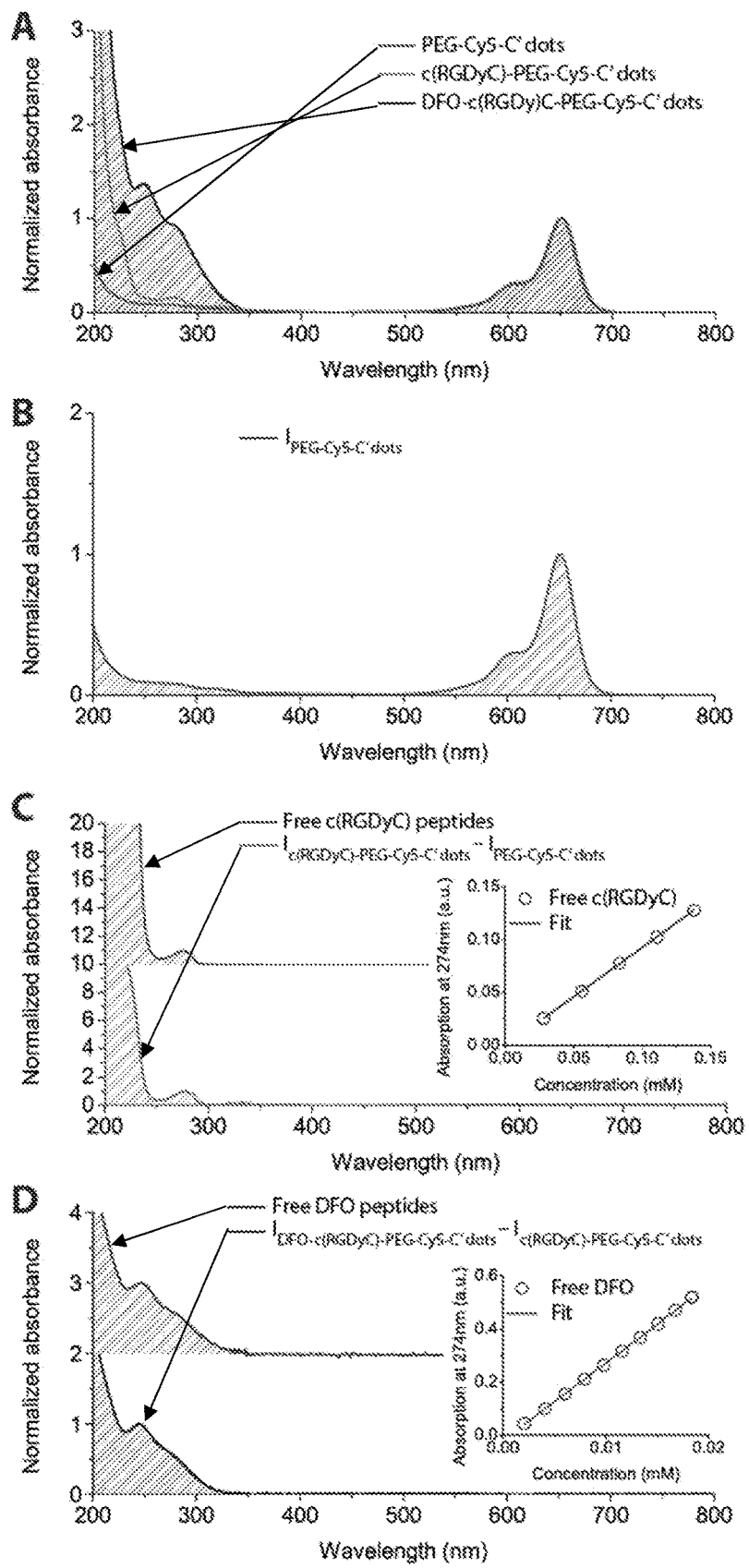
FIG. 12 shows estimation of the numbers of ligands per multifunctional C' dots that contain more than one type of functional ligand on their surface by deconvolution of the absorbance spectrum. (A) Comparison of UV-vis absorbance spectra of C' dots with step-by-step increased functionalities, based on which the absorbance spectra of each component of DFO-c(RGDyC)-PEG-Cy5-C' dots are generated (B to D). The absorbance signal of c(RGDyC) peptides on C' dot surfaces (green curve in C) is obtained via subtracting the absorption signal of PEG-Cy5-C' dots (red curve in AB) from that of c(RGDyC)-PEG-Cy5-C' dots (green curve in A). The absorbance of DFO chelator on C' dot surfaces (blue curve in D) is obtained via subtracting the absorption signal of cRGDY-PEG-Cy5-C' dots (green curve in A) from that of DFO-c(RGDyC)-PEG-Cy5-C' dots (blue curve in A). The resulting spectra of c(RGDyC) and DFO are then compared to the absorbance of free c(RGDyC) peptides (top green curve in C) and DFO-silane molecules (top blue curve in D), respectively (C and D), confirming the consistency in the spectra. The reason why conjugated DFO-silane was used instead of DFO-NCS molecules for the comparisons to DFO on the NPs is that the conjugation of DFO-NCS to amine-functionalized ligand, e.g. amine-silane, causes a substantial change in the absorbance spectrum (data not shown). Therefore, the absorbance of DFO-silane is more consistent with the DFO groups on C' dots than free DFO-NCS. The resulting standard spectra of PEG-Cy5-C' dots (B), c(RGDyC) on C' dots (lower green curve in C) and DFO on C' dots (lower blue curve in D) are normalized and then used as standards to fit the absorbance spectra of other DFO-c(RGDyC)-PEG-Cy5-C' dot samples (E). The fitting equation is a linear combination of the absorption intensity of different components, i.e. $F(A, B, C, D) = A*I_{PEG-Cy5-C' dots} + B*I_{c(RGDyC)} + C*I_{DFO} + D$, which well describes the sample spectrum (E). A parameter D is added to the fitting equation to correct for possible base line drift of the UV-vis setup. The fitting deconvolutes the sample spectrum (E) into the contributions of individual components (F to H), from which the number of Cy5, c(RGDyC), and DFO molecules per NP were estimated to be around 1.6, 23 and 4 using the extinction coefficients of Cy5 free dye, free c(RGDyC) peptide and free DFO-silane molecule, respectively. While the extinction coefficient of Cy5 was used as reported by the manufacturer, separate calibrations of extinction coefficients of free c(RGDyC) peptides and free DFO-silane molecules were performed with results inserted in (C) and (D), respectively.
Figure 12:
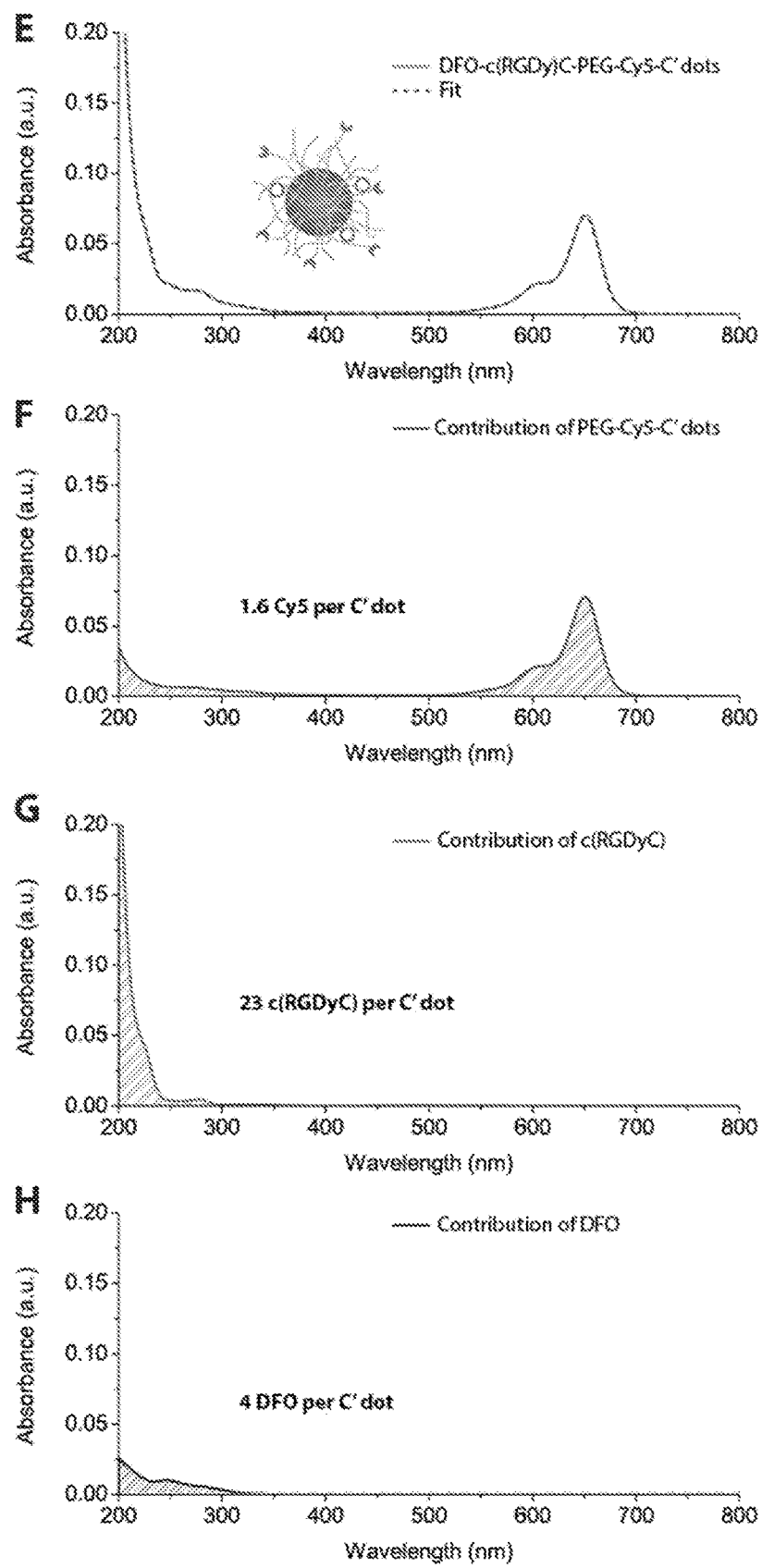

The additional surface amine groups can subsequently be used to introduce secondary functional ligands to the C' dot silica surface. To test this idea, following the addition of amino-silane, DFO-NCS was added in a subsequent step to react with the amine groups sitting under the PEG layer via amine-NCS reaction (FIG. 1). The advantage of this method is that a relatively high DFO concentration can now be applied to push the DFO-NCS molecules to penetrate the PEG layer, while extra DFO can be easily removed in the final purification steps via centrifugation and GPC. The GPC elugram of the resulting DFO-c(RGDyC)-PEG-Cy5-C' dots suggested a relatively clean sample with only one main peak of NP product (FIG. 4A). After purification narrowly dispersed C' dots with diameter of 6.4 nm were obtained (FIGS. 4B and C, Table 1). The purified DFO-c(RGDyC)-PEG- Cy5-C' dots had a distinct absorbance signature between 200 and 300 nm as compared to NH$_2$-c(RGDyC)-PEG-Cy5-C' dots (FIG. 4D). This absorbance signal corresponds to the absorbance by DFO molecules, and increases as the concentration of DFO-NCS used in the reaction is increased. The absorbance of DFO-c(RGDyC)-PEG-Cy5-C' dots was deconvoluted into individual contributions from each component through fitting the spectrum using a set of absorbance standards (FIG. 12). The number of Cy5, c(RGDyC) and DFO molecules per particles were then estimated to be around 1.6, 23, and 4, respectively, for C' dots synthesized using a DFO-NCS concentration of around 0.2 mM (FIG. 12 and Table 1). These optical spectroscopy results demonstrate the successful attachment of DFO to NH$_2$-c(RGDyC)-PEG-Cy5-C' dots and confirm the accessibility of the amine groups on NH$_2$-c(RGDyC)-PEG-Cy5-C' dots for further reactions. Other than the attachment of DFO molecules, no substantial change is observed in further GPC and FCS based C' dot characterizations relative to c(RGDyC)-PEG-Cy5-C' dots or NH$_2$-c(RGDyC)-PEG-Cy5-C' dots (Table 1) suggesting that this room-temperature, post-PEGylation modification has only minor effects on the properties of regular c(RGDyC)-PEG-Cy5-C' dots thereby maximizing the chance for clinical translation.

Figure 13:
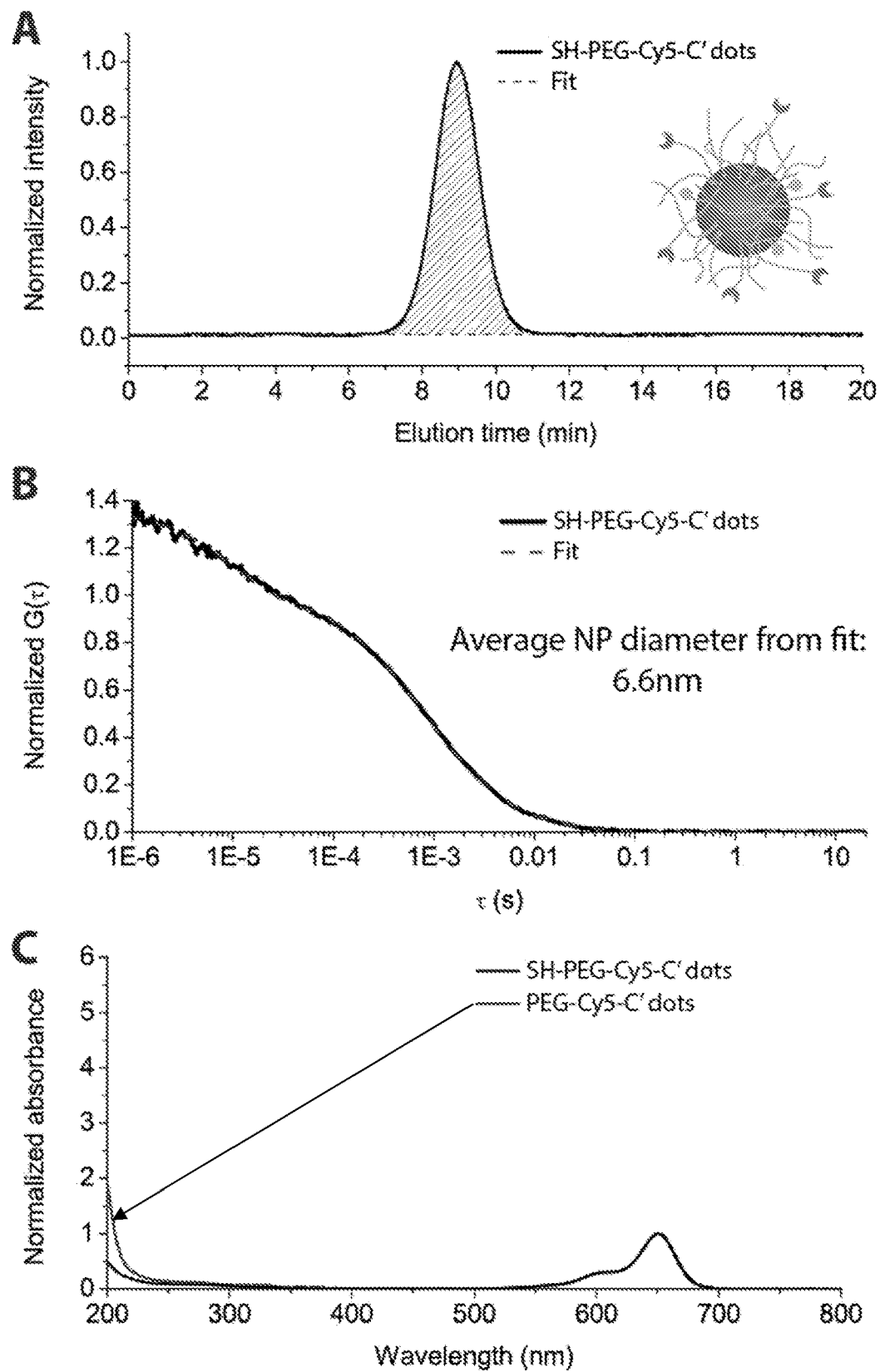
FIG. 13 shows generalization of the post-PEGylation surface modification by using other types of conjugation chemistries. (A to C) GPC elugram (A), FCS correlation curve and fit (B), and UV-vis absorbance spectrum (C) of purified thiol-functionalized SH-PEG-Cy5-C' dots, which were synthesized via introducing thiol-silane to the reaction mixture of PEG-Cy5-C' dots after NP PEGylation but before purification. A slightly increased absorption below 250 nm was observed (C) as compared to the NPs without additional thiol functionalization. (D to F) GPC elugram (D), FCS correlation curve and fit (E), and UV-vis absorbance spectrum (F) of purified FITC-PEG-Cy5-C' dots, which were synthesized via further introducing FITC-NCS dye to the reaction mixture of thiol-functionalized SH-PEG-Cy5-C' dots after thiol-silane addition but before NP purification. The absorption signal of FITC-PEG-Cy5-C' dots substantially increases at the wavelength around 450 nm as compared to that of the same synthesis using PEG-Cy5-C' dots without thiol-functionalization (F). This signal corresponds to the absorbance signal of FITC dye in DI water, confirming the successful attachment of FITC and the accessibility of the thiol groups on SH-PEG-Cy5-C' dots. Please note that a low FITC signal is also observed in the sample without thiol-functionalization and is likely due to either the non-specific adsorption of FITC dyes to C' dots or to residual thiol groups from the standard C' dot synthesis resulting from the excess of thiol-silane used in the Cy5 dye silane conjugation step.
Figure 13:
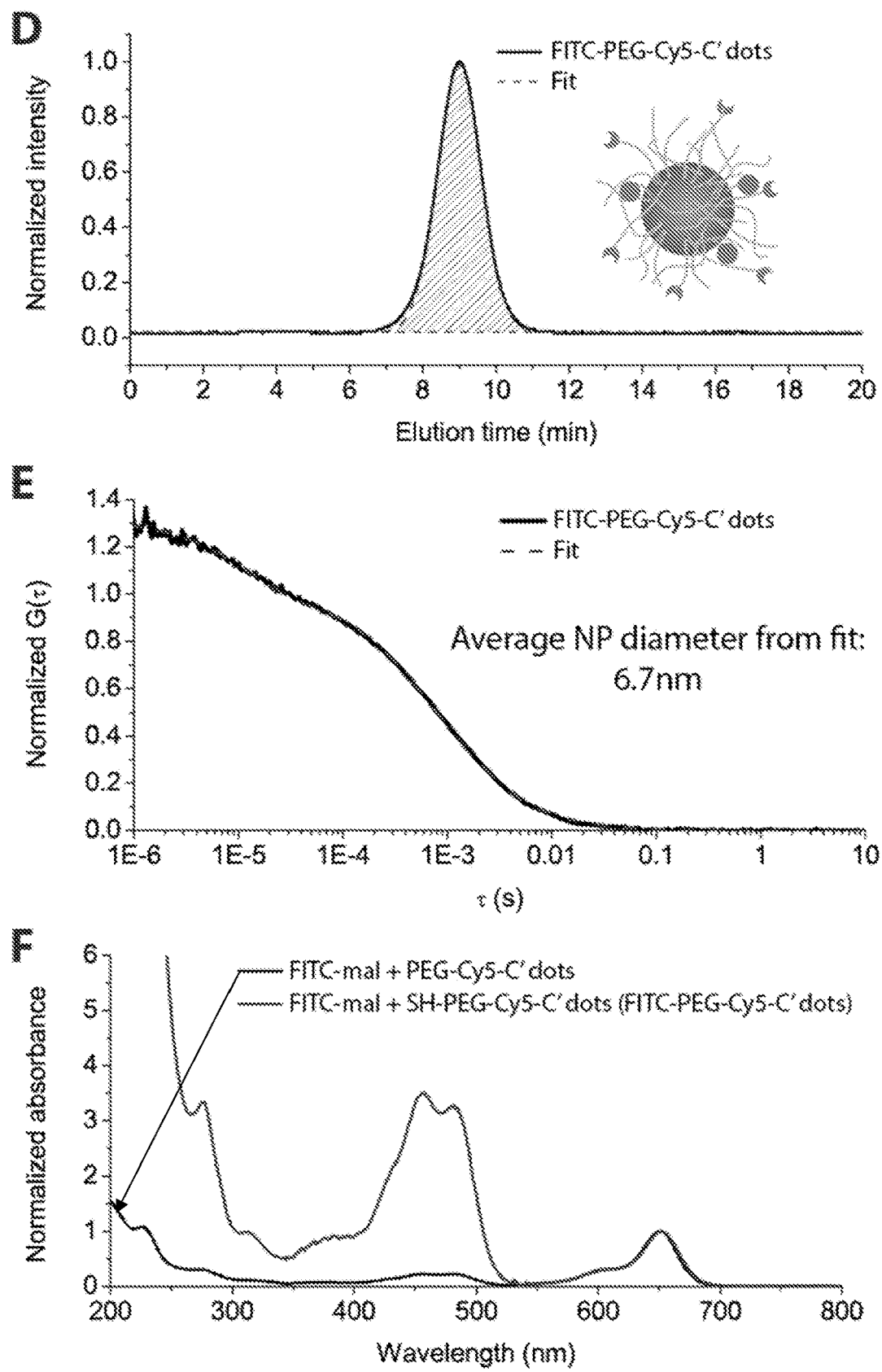

Generalization of the PPSMI method. A similar approach to attaching DFO to c(RGDyC)-PEG-C' dots can also be used to introduce other types of functional ligands. For example, 1,4,7,10-tetraazacyclododecane-1,4,7,10-tetraacetic acid (DOTA) is one of the most efficient chelators for radio-labeling with radioisotopes like $^{177}$Lu. Via replacing DFO-NCS by DOTA-NCS, narrowly dispersed DOTA functionalized c(RGDyC)-PEG-C' dots, i.e. DOTA-c(RGDyC)-PEG-C' dots, were produced thereby enabling, e.g. $^{177}$Lu radio-labeling (FIGS. 4E to H). This approach can also be applied to other types of conjugation chemistries. For example, by replacing amino-silane with thiol-silane in the post-PEGylation surface modification step, thiol-functionalized C' dots can be produced in which the additional thiol groups can further react, via thiol-ene click reaction, with e.g. maleimido-functionalized ligands. As proof-of-principle, thiol-silane was introduced onto the silica surface of PEG-Cy5-C' dots via this approach, generating narrowly dispersed SH-PEG-Cy5-C' dots (FIGS. 13A to C, Table 1). Afterwards, maleimide functionalized FITC dye (mal-FITC) was added into the reaction mixture of SH-PEG-Cy5-C' dots before the purification step to functionalize the NPs with pH sensing FITC dyes via thiol-maleimide conjugation (FIG. 1). The resulting FITC-PEG-Cy5-C' dots exhibited a clean GPC elugram after purification indicating a high quality NP product (FIG. 13D). FCS characterization indicated an average particle size of 6.7 nm (FIG. 13E, Table 1). The purified FITC-PEG-Cy5-C' dots showed an additional absorption feature at wavelengths around 450 nm as compared to PEG-Cy5-C' dots corresponding to the characteristic absorption of FITC dye (FIG. 13F). Results demonstrate successful attachment of FITC dye through thiol-ene click reaction and the accessibility of the thiol groups on thiol-PEG-Cy5-C' dots.

In addition to the amine-silane/NCS-ligand and thiol-silane/mal-ligand chemistries described above, other types of conjugation chemistries could also be applied using a similar approach, e.g. azide-silane/alkyne-ligands (vide infra).

Figure 14:
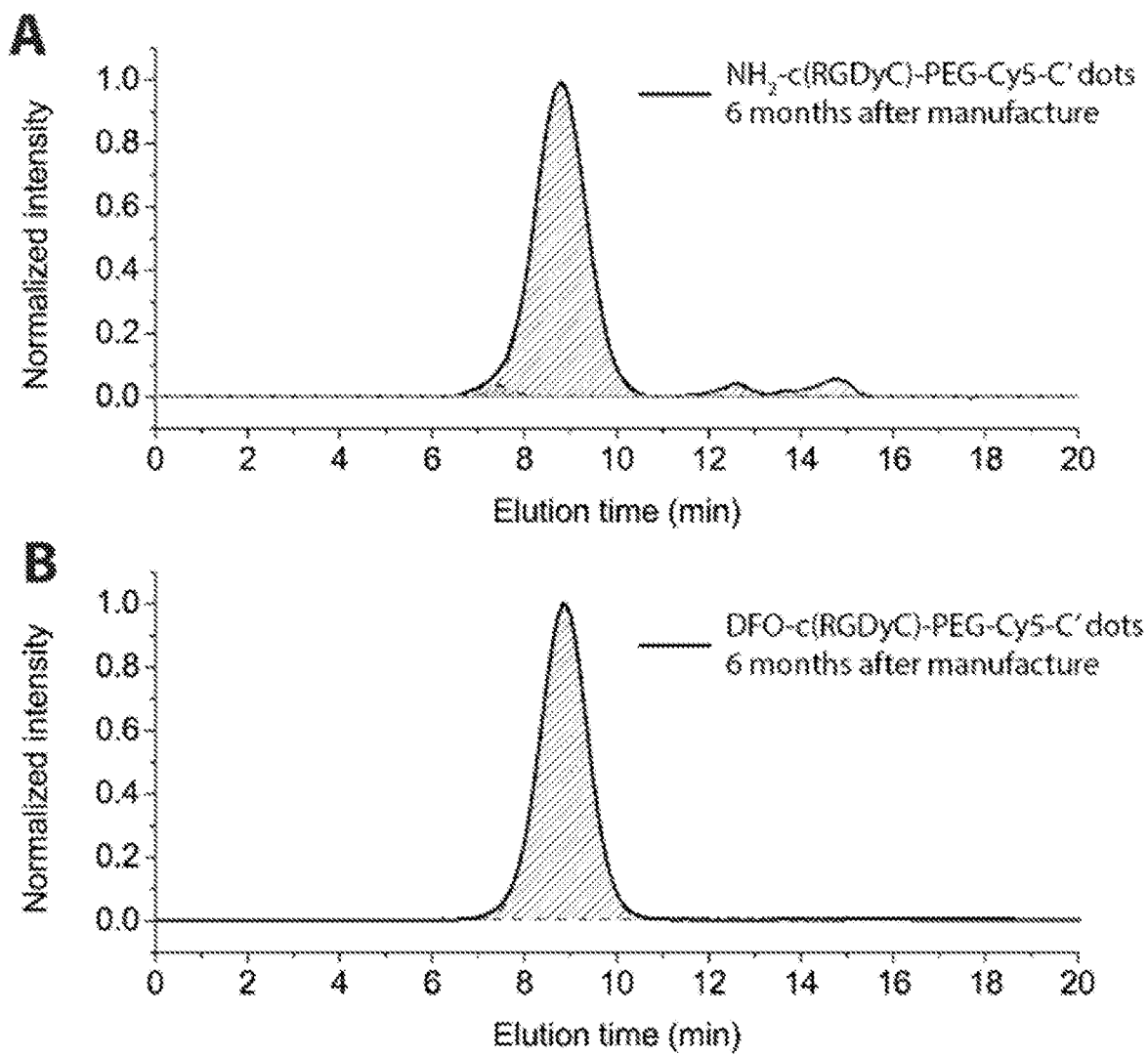
FIG. 14 shows stability of amine-functionalized multi-functional C' dots. GPC elugram of purified NH$_2$-c(RGDyC)-PEG-Cy5-C' dots (A) and DFO-c(RGDyC)-PEG-Cy5-C' dots (B) at 6 month time point after NP manufacture. In both cases NPs were stored in PBS buffer at 4° C. during the stability tests. The elugram of NH$_2$-c(RGDyC)-PEG-Cy5-C' dots (A) showed small additional peaks associated with smaller molar mass products, indicating NP degradation likely caused by the primary amine groups on the silica surface. In comparison, the DFO-c(RGDyC)-PEG-Cy5-C' dots (B) remained stable during the entire period of the stability test.

The PPSMI synthesis approach enables the production of a family of C' dots with different functionalities, including amine- and thiol-functionalized C' dots. These reactive C' dots may become useful platforms allowing for subsequent modifications, i.e. after NP manufacture, using a variety of ligands depending on the targeted application. One of the disadvantages of working in particular with NH$_2$-c(RGDyC)-Cy5-C' dots is, however, that they exhibit reduced NP stability. For NH$_2$-c(RGDyC)-Cy5-C' dots, peaks associated with small molar mass species started to appear in the GPC elugrams 6 months after NP manufacture (FIG. 14A). This may be due to e.g. peptide groups released from the NP surface. In comparison, the regular c(RGDyC)-PEG-C' dots exhibit distinct NP stability over a period of at least two years without change in either NP characteristics or in-vivo performance. Therefore, we suspect that the degradation of aminated C' dots is probably caused by the localized high pH environment around the primary amine groups accelerating silane hydrolysis.

In contrast, no substantial change was observed in GPC elugram and FCS characterization for DFO-c(RGDyC)-Cy5-C' dots 6 months after NP manufacture using the amine based PPSMI approach, indicating the desired NP stability (FIG. 14B). This is likely due to DFO-NCS terminating the primary amine groups during the post-PEGylation modification reaction thereby shortening the life time of C' dots with active primary amine groups. For this reason, although the amine- and thiol-functionalized C' dots can in principle be produced separately for further modification after NP manufacture, it is most desirable to directly react these functional groups via the introduction of additional functional NP ligands during NP manufacture to quickly convert these reactive groups for desired NP stability and long product shelf-life.

Tetra-functional C' dots with three types of functional surface ligands: Modularity of the PPSMI approach. The different conjugation chemistries described above can be combined during post-PEGylation surface modification reactions to provide modular pathways to multifunctional C' dots, all in a one-pot synthesis.

Figure 5:
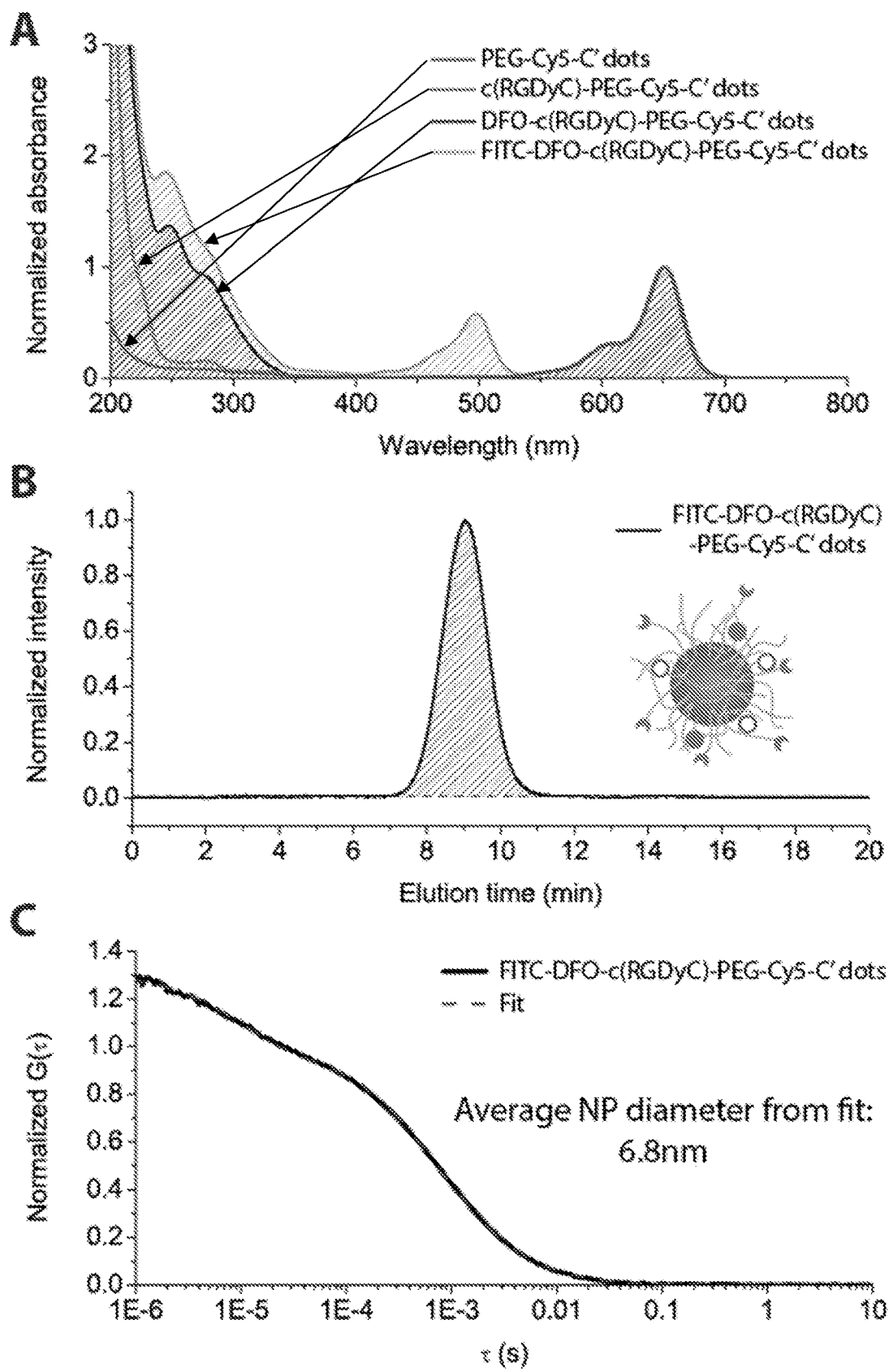
FIG. 5 shows tetra-functional C' dots containing three types of functional ligands on the NP surface. (A) Comparison of C' dots with step-by-step increased functionalities as indicated in the inset. (B and C) GPC elugram (B) and FCS correlation curve with fit (C) of purified FITC-DFO-c(RGDyC)-PEG-C' dots. (D and E) Emission spectra of purified FITC-DFO-c(RGDyC)-PEG-C' dots with excitation wavelengths of 500 nm (D) and 650 nm (E), respectively. (F) Ratiometric calibration curve obtained via dividing the peak sensor emission intensity (525 nm) by the peak reference emission intensity (660 nm) versus pH. The UV-vis absorbance spectra shown in (A) were measured in PBS buffer solution for a desired FITC signal to estimate the number of FITC dyes per NP.
Figure 5:
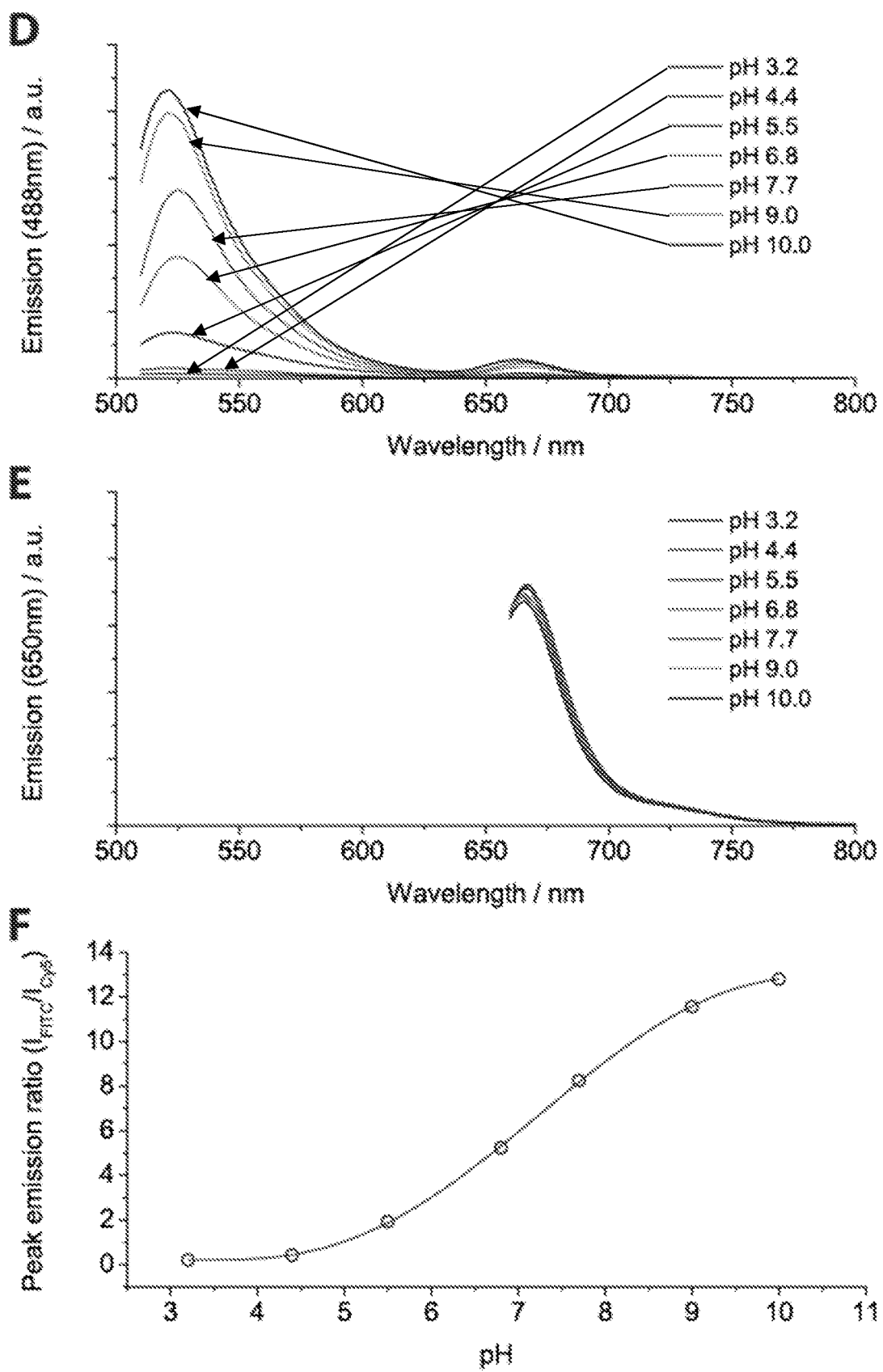
Figure 15:
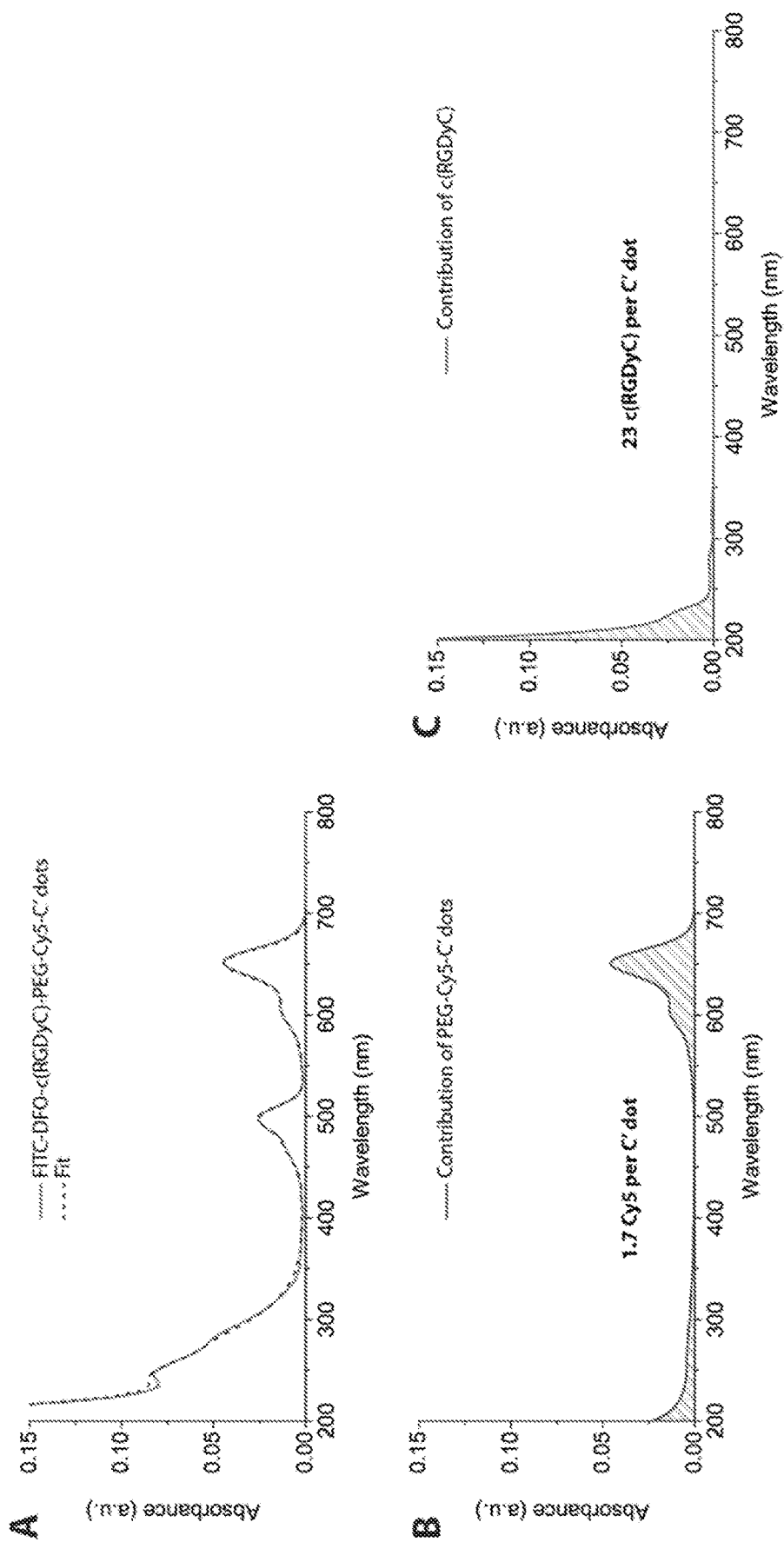
FIG. 15 shows deconvolution of the absorbance spectrum of multifunctional C' dots containing three types of functional ligands on NP surface. (A) UV-vis absorbance spectrum of FITC-DFO-c(RGDyC)-PEG-Cy5-C' dots which can be well fitted using a linear combination of absorption signals from PEG-Cy5-C' dots, c(RGDyC), DFO, and FITC. The deconvolution is similar to that described for DFO-c(RGDyC)-PEG-Cy5-C' dots in FIG. 12, but further includes the UV-vis signal of FITC in the analysis. Based on the fit, the spectrum (A) is deconvoluted into contributions from PEG-Cy5-C' dots (B), c(RGDyC) (C), DFO (D), and FITC (E). From these contributions in the fit, the numbers of Cy5, c(RGDyC), DFO, and FITC molecules per NP are then estimated to be around 1.7, 23, 19 and 4, respectively.
Figure 15:
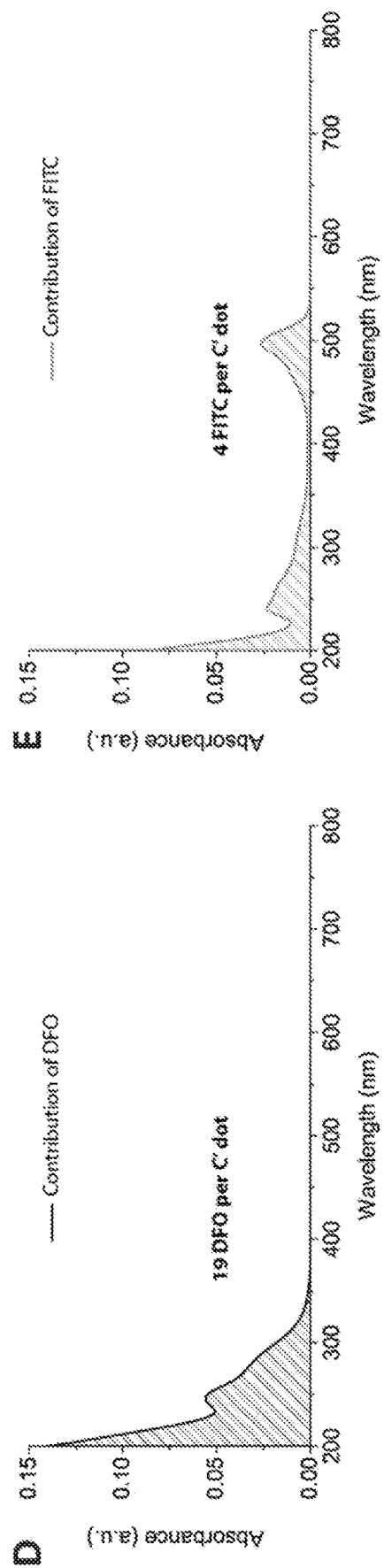

As proof-of-principle, c(RGDyC)-PEG-Cy5-C' dots were first functionalized with amine groups after PEGylation, generating NH$_2$-c(RGDyC)-PEG-Cy5-C' dots. DFO-NCS chelators were then attached to these C' dots via amine-NCS conjugation thereby terminating the primary amine groups. Afterwards, the resulting DFO-c(RGDyC)-PEG-Cy5-C' dots were further functionalized with thiol-silane generating SH-DFO-c(RGDyC)-PEG-Cy5-C' dots. FITC-mal pH sensing dyes were finally inserted into the PEG layer and attached to the C' dot silica surface via thiol-ene click reaction terminating the reactive thiol groups (FIG. 1). The resulting narrowly dispersed FITC-DFO-c(RGDyC)-PEG-Cy5-C' dots integrated a total of four functional groups as confirmed by absorbance measurements (FIG. 5A), while the particle size of 6.8 nm remained narrowly distributed and below 7 nm as suggested by both, GPC and FCS characterizations (FIGS. 5B and C). The numbers of Cy5, c(RGDyC), DFO and FITC groups per NP were estimated according to the deconvolution approach described above using a set of absorbance standards for each individual component (FIG. 15 and Table 1). The c(RGDyC) peptides were attached to the outside of the C' dot PEG layer enabling active tumor targeting. The DFO and FITC ligands allowing for radioisotope chelating and pH sensing, respectively, were inserted into the PEG layer. This design ensures their accessibility to small ions, but at the same time diminishes potential negative side effects to the in-vivo performance of C' dots. The NPs exhibited varying fluorescence intensity at around 525 nm at different pH when being excited at 488 nm (FIG. 5D). This fluorescence can be assigned to the emission of pH sensitive FITC dye inserted into the PEG layer. In comparison, the NPs exhibited pH independent fluorescence at around 675 nm when being excited at 645 nm (FIG. 5E). This fluorescence corresponds to the Cy5 dyes inside the silica core. This bright NIR fluorescence not only enables optical imaging using the C' dots e.g. for image-guided surgery, but also can be used as a reference signal for ratiometric pH sensing. To that end, a ratiometric calibration curve was obtained via dividing the peak sensor emission intensity (525 nm) by the peak reference emission intensity (660 nm) as a function of pH (FIG. 5F).

It is interesting to note that the pH response of FITC-DFO-c(RGDyC)-PEG-Cy5-C' dots covers a wider pH range (FIG. 5E), i.e. from pH 4 to pH 10 with middle pH around 7, as compared to that of the previously reported pH sensing C dots, i.e. from pH 4.5 to pH 8 with middle pH around 6.5.[41] This is likely caused by the terminated secondary amine groups under the PEG layer of FITC-DFO-c(RGDyC)-PEG-Cy5-C' dots affecting the local acidity around the FITC dyes. The colocalization of FITC and amine groups in the PEG layer endows C' dots with distinct pH sensitivity, in addition to other particle functions. This design strategy also provides a concept to further tailor the optical properties of C' dots via carefully tuning the chemical environments surrounding the dyes, i.e. the silica core and the PEG layer.

Orthogonality of the PPSMI approach. One of the most significant advantages of the PPSMI approach described above is the fact that it is supported by a rich toolbox of well-established, modular, as well as orthogonal conjugation chemistries. For example, in addition to the amine-silane/NCS-ligand and thiol-silane/mal-ligand chemistries described above, other types of conjugation chemistries can also be applied using a similar approach, e.g. azide-silane/alkyne-ligands. Furthermore, since these conjugation reactions using different chemistries usually do not interfere with each other, different functional ligands can be simultaneously attached to C' dots.

Figure 16:
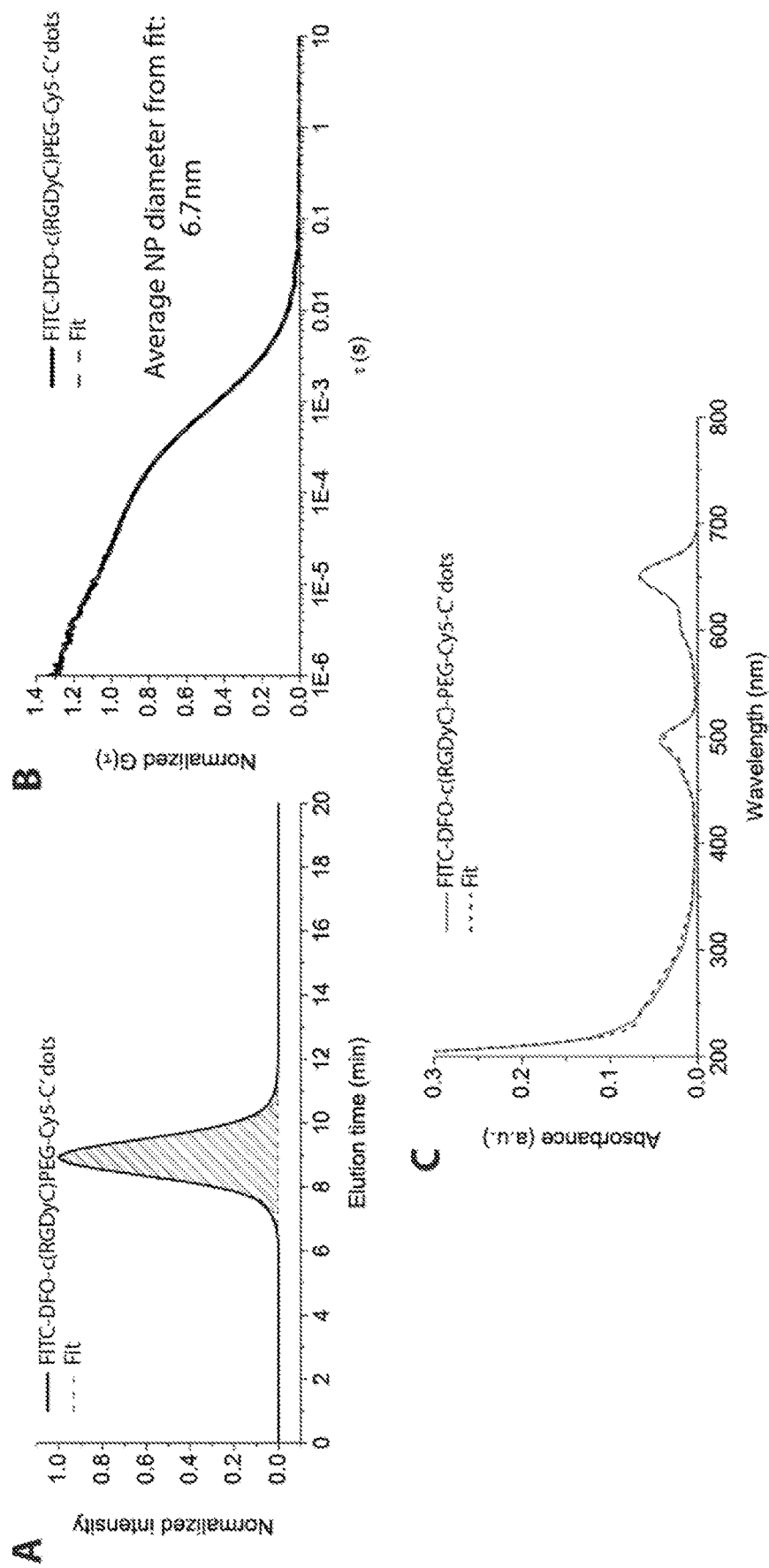
FIG. 16 shows characterization of tetra-functional C' dots synthesized via orthogonal surface functionalization and deconvolution of the absorbance spectrum. (A to C) GPC elugram (A), FCS correlation curve with fit (B), and UV-vis spectrum (C) with fit from deconvolution of tetra-functional FITC-DFO-c(RGDyC)-PEG-Cy5-C' dots, in which FITC and DFO groups were introduced simultaneously instead of being attached step by step (compare to results in FIG. 15). (D to G) Deconvolution of the UV-vis spectrum (C) into contributions from PEG-Cy5-C' dots (D), c(RGDyC) (E), DFO (F), and FITC (G). From these contributions in the fit, the numbers of Cy5, c(RGDyC), DFO, and FITC molecules per NP are then estimated to be around 1.9, 22, 4 and 3, respectively.
Figure 16:
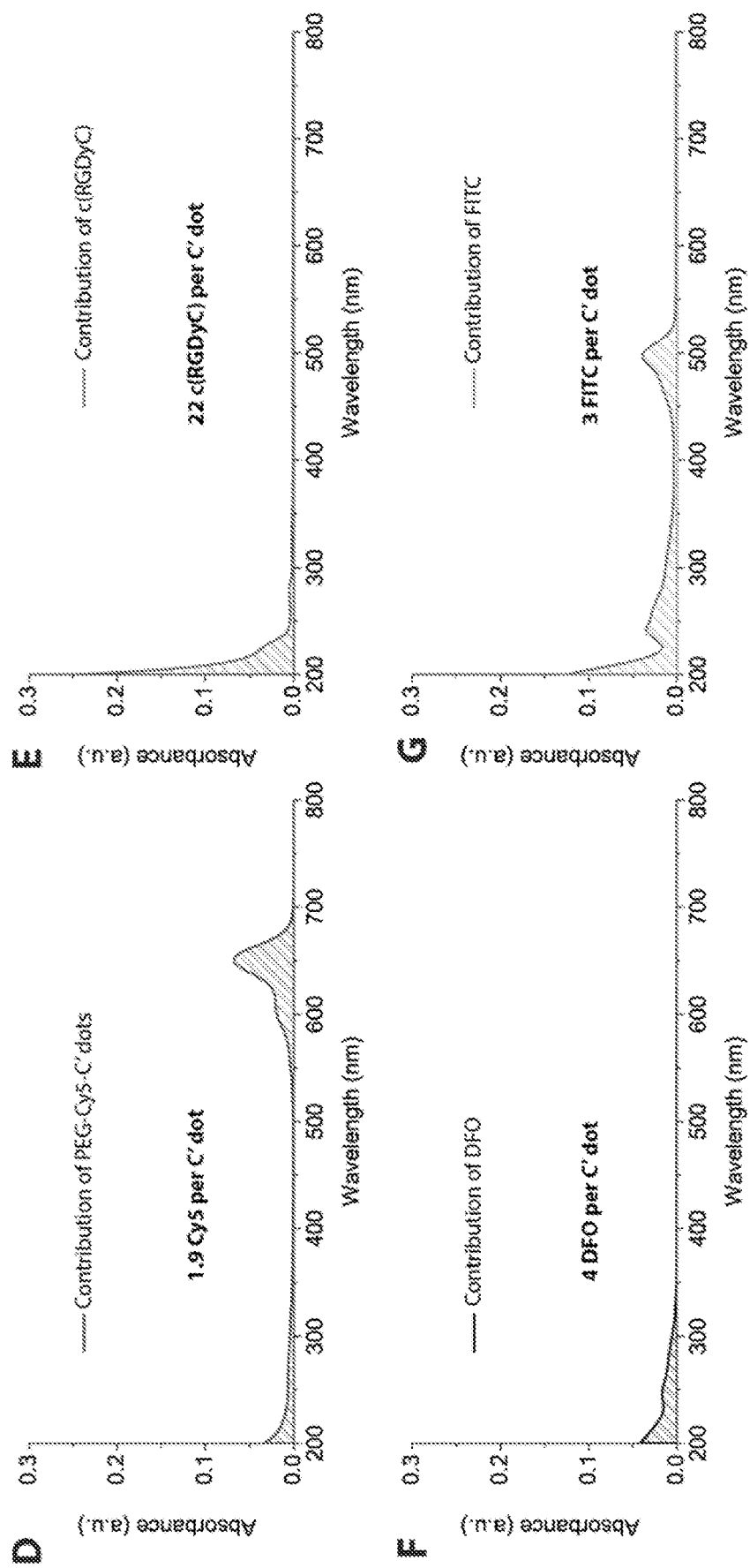

As proof-of-principle, instead of sequential addition of amine-silane, DFO-NCS, thiol-silane and FITC-mal, amine-silane and thiol-silane were added together to the c(RGDyC)-PEG-Cy5-C' dot reaction to simultaneously functionalize C' dots with both amine and thiol groups. DFO-NCS and FITC-mal were then added together to simultaneously convert the amine and thiol groups into functional ligands. The resulting FITC-DFO-c(RGDyC)-Cy5-C' dots exhibited the desired GPC elugram after purification, and had an average diameter around 6.7 nm per FCS characterization (FIGS. 16A and B). By fitting the UV-vis spectrum (FIG. 16C) of the purified particles, the absorption of each individual component was deconvoluted, including Cy5, c(RGDyC), DFO and FITC (FIGS. 16D to G). This indicated the successful surface modification with DFO and FITC using simultaneous conjugation reactions. The PPSMI approach is a powerful method for functionalizing PEGylated silica NPs, since the orthogonality of conjugations using PPSMI significantly shortens the reaction time required for surface modification thereby further simplifying the manufacture of multifunctional silica NPs.

Penta-functional C' dots with four types of functional surface ligands via combinations of surface modifications during and post PEGylation. We have described that different types of functional groups can be introduced to the C' dot surface either during the PEGylation step or via post-PEGylation surface modifications. The combination of these two approaches provides modular and orthogonal pathways to multifunctional C' dots with the highest number of surface functional groups, all in a one-pot synthesis approach in aqueous media. To that end, as proof-of-principle we synthesized a penta-functional C' dot with a total of four different functional ligands on the NP surface (FIG. 1) allowing for simultaneous optical tracing, specific cell targeting, ratiometric sensing, radiometal chelating and potential drug delivery.

Figure 17:
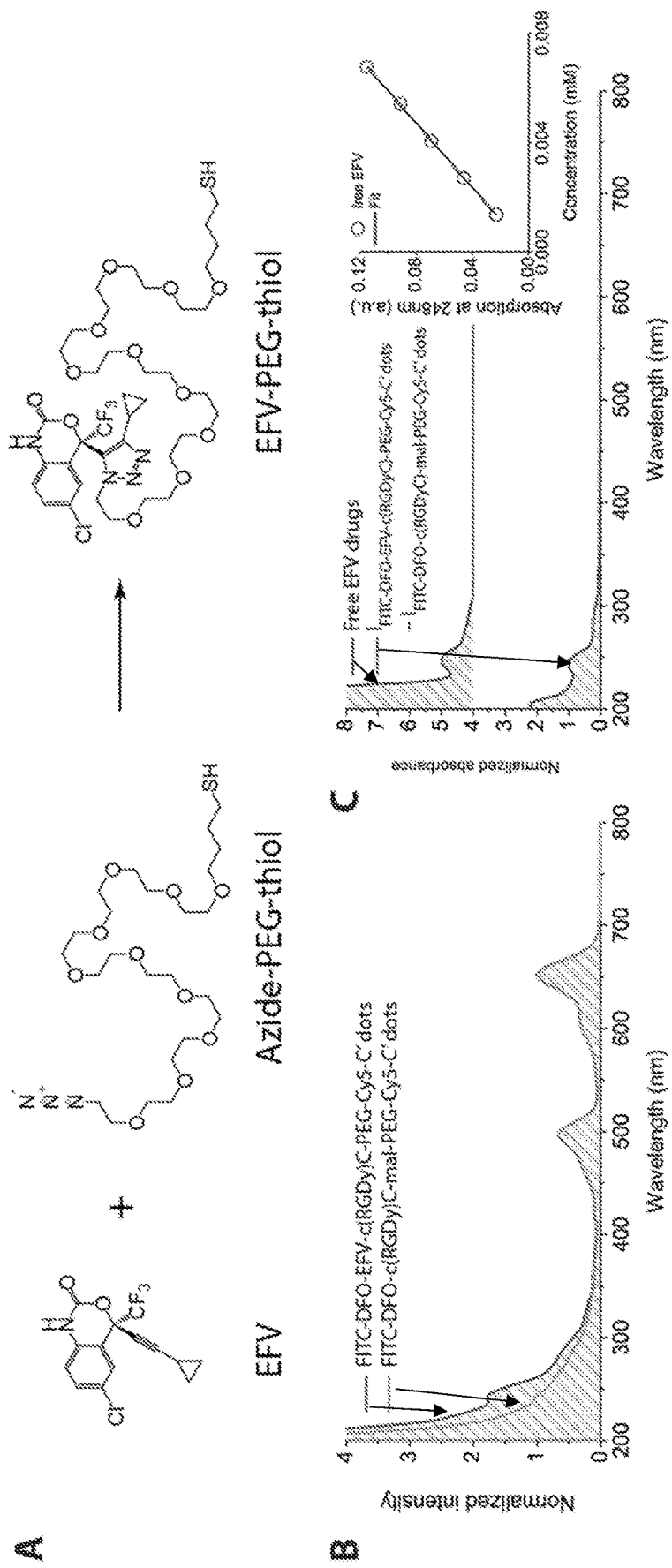
FIG. 17 shows attachment of small therapeutic drugs for the preparation of penta-functional C' dots. (A) Conjugation reaction of EFV and azide-PEG-thiol to functionalize EFV drug molecules with thiol groups. The resulting EFV-PEG-thiol molecules were then attached to c(RGDyC)-mal-PEG-Cy5-C' dots via thiol-ene reaction after NP PEGylation and before the introduction of DFO and FITC. (B) Comparison of UV-vis spectra of FITC-DFO-EFV-c(RGDyC)-PEG-Cy5-C' dots and FITC-DFO-c(RGDyC)-mal-PEG-Cy5-C' dots. The two samples were obtained from the same reaction batch with and without the addition of EFV-PEG-thiol. (C) Standard absorbance spectrum of EFV on C' dots, which is obtained via subtracting the absorbance of FITC-DFO-c(RGDyC)-mal-PEG-Cy5-C' dots from the absorbance of FITC-DFO-EFV-c(RGDyC)-PEG-Cy5-C' dots. The resulting spectrum is consistent with the UV-vis spectrum of free EFV drugs indicating the successful attachment of EFV to C' dots. The calibration of extinction coefficients of free EFV drug molecules is inserted in (C).

In order to synthesize the penta-functional C' dots, the NP surface was first modified with specific cell targeting groups, i.e. c(RGDyC) peptides, and maleimide groups during the PEGylation step via co-condensing c(RGDyC)-PEG-silane, mal-PEG-silane, and PEG-silane onto the surface of silica cores as described above. After PEGylation, thiol-modified small drug molecules were added into the reaction mixture to attach to (thereby terminating) the maleimide groups on the C' dot surface via thiol-ene click reaction. For proof-of-principle, we selected Efavirenz (EFV, see FIG. 6A for molecular structure) as an example of a small therapeutic drug, which is a well-known antiretroviral medication used to treat and prevent HIV/AIDS. EFV contains an alkyne group which in a separate step was reacted with heterobifunctional azide-PEG-thiol through click chemistry to modify EFV with thiol groups (FIG. 17A). Additionally, EFV exhibits unique absorbance characteristics in the sub-300 nm wavelength range which can be differentiated from the absorbance of the other functional groups on the penta-functional C' dots (FIGS. 17B and C). It should be noted that other drug linger conjugation strategies could be used here, including enzyme cleavable drug-linker conjugates described by us earlier. After attaching thiol-modified EFV to c(RGDyC)-mal-PEG-Cy5-C' dots, amine-silane, DFO-NCS, thiol-silane and FITC-mal were added into the reaction mixture in a sequence following the PPSMI synthesis approach to tetra-functional C' dots described above to further introduce DFO and FITC groups to EFV-c(RGDyC)-PEG-Cy5-C' dots enabling radiometal chelating and ratiometric pH sensing, respectively.

Figure 6:
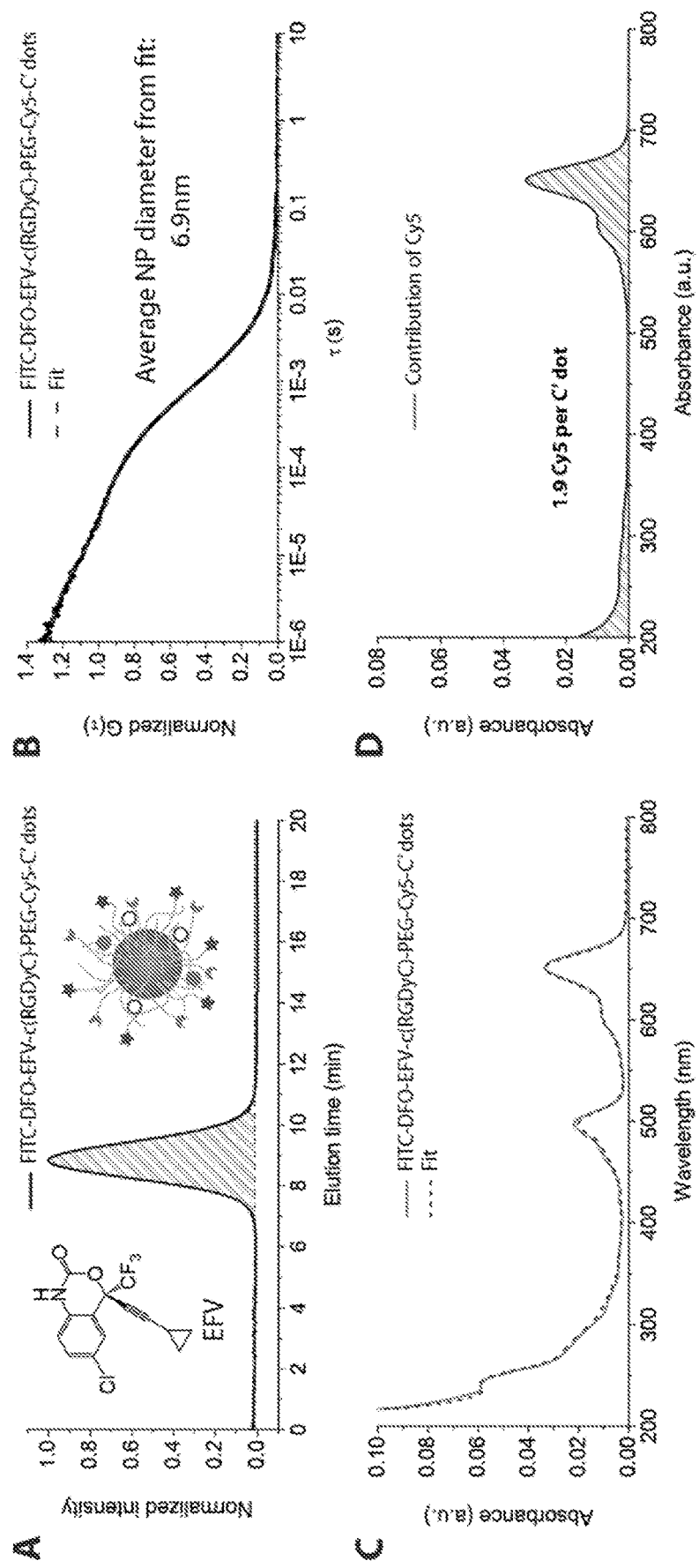
FIG. 6 shows penta-functional C' dots containing four types of functional ligands on the NP surface. (A to C) GPC elugram (A), FCS correlation curve (B), and UV-vis spectra with fit (C) of penta-functional FITC-DFO-EFV-c(RGDyC)-PEG-Cy5-C' dots. The chemical structure of EFV drug is instead in (A). (D to H) Deconvolution of the UV-vis spectra (C) into contributions from PEG-Cy5-C' dots (D), c(RGDyC) (E), EFV (F), DFO (G), and FITC (H). The deconvolution was obtained via fitting the UV-vis spectra (C) using a set of standard spectra of each individual component (FIGS. 12B to D, FIG. 15E and FIG. 17C).
Figure 6:
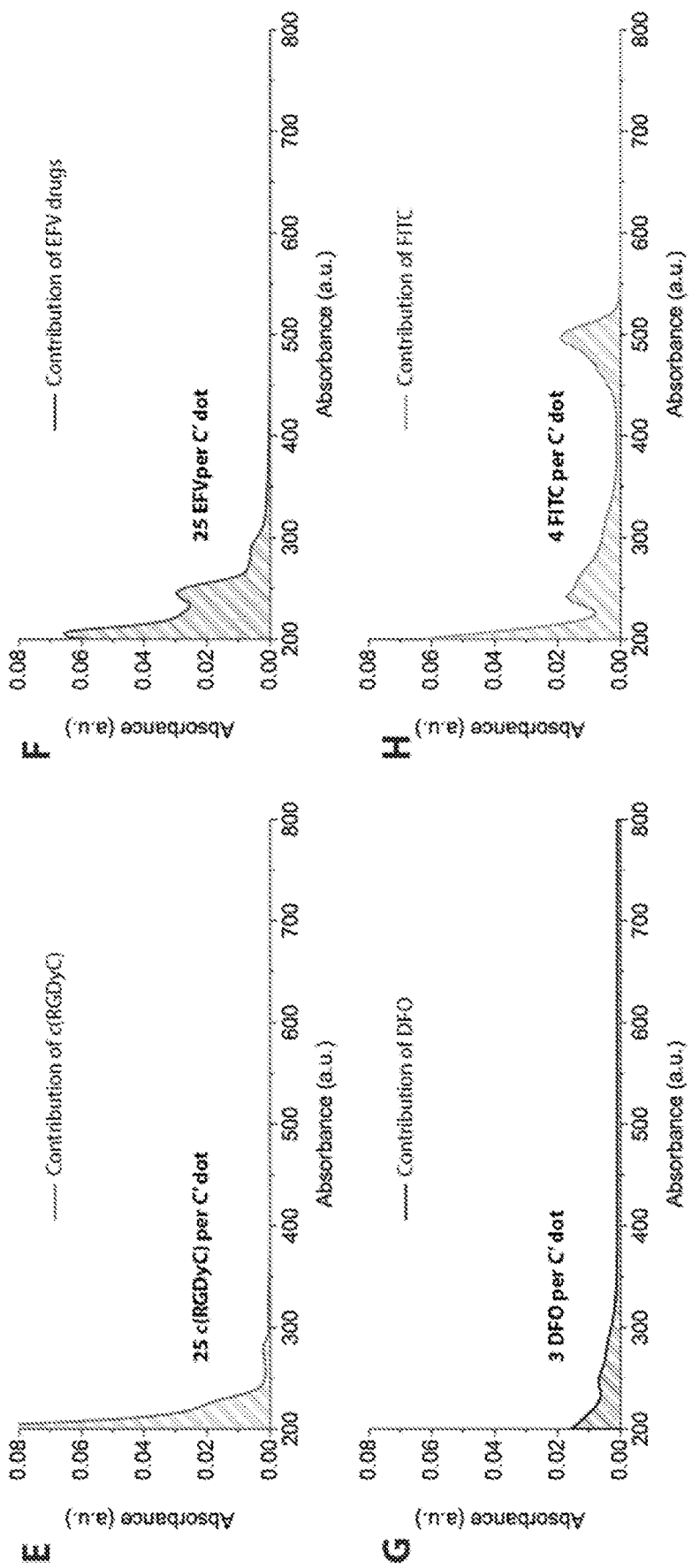

The resulting FITC-DFO-EFV-c(RGDyC)-PEG-Cy5-C' dots showed the desired GPC elugram after purification indicating high particle purity (FIG. 6A). The FCS autocorrelation curve was well fitted using a single-mode correlation function indicating a narrow particle size distribution (FIG. 6B). The absorbance of FITC-DFO-EFV-c(RGDyC)-PEG-Cy5-C' dots exhibited multiple peaks across the spectrum, which could be successfully deconvoluted into individual contributions from each component through fitting the spectrum using a set of absorbance spectrum standards (FIGS. 6D to H). The specific average numbers for each of the functional groups on the C' dots were then estimated through dividing the concentrations of each component by the concentration of NPs obtained from FCS (Table 1 and FIGS. 6C to H) similar to what has been described above. Although a total of four types of different functional groups are attached to the C' dot surface, with 6.9 nm the average particle diameter remained below 7 nm, still very close to the size of clinically translated C' dots (Table 1).

In this example, we describe a one-pot type synthesis approach to introduce, in a modular and partially orthogonal way, multiple (here: up to four) types of functional ligands onto the surface of fluorescent ultrasmall (<10 nm diameter) PEGylated silica based nanoparticles (here C' dots). Different types of functional groups can be introduced during the PEGylation step via co-condensing different heterobifunctional PEG-silanes onto the surface of the silica cores. We have demonstrated, however, that this and similar approaches where functional groups are introduced during the PEGylation step, are limited and often lead to undesired properties like particle aggregation. These limitations can be overcome by moving to post-PEGylation surface modification by insertion (PPSMI) reactions. After PEGylation, small and orthogonally reactive ligands, e.g. amino- and/or thiol-silane molecules, can be inserted into the PEG layer and attached to the silica surface via silane condensation allowing for modular NP modifications with functionalities beyond fluorescence for particle tracing and tumor targeting ligands. For example, DFO and DOTA, which are some of the most efficient chelators, e.g. for $^{89}$Zr and $^{177}$Lu labeling, respectively, can be attached between the PEG chains and to the silica surface of C' dots through the reaction with amine or thiol groups. The PPSMI method to functionalize C' dot-type PEGylated silica nanoparticles can be generalized by adopting other types of widely used conjugation chemistries, including thiol-ene and azide-alkyne click reactions. Furthermore, post-PEGylation surface modifications by insertion using different conjugation chemistries can be combined to provide modular and orthogonal access to multifunctional C' dots. Finally, in order to maximize surface functionality, post-PEGylation surface modifications via insertion of ligands between PEG chains can be combined with those during the PEGylation step leading to surface ligands on the outside of the surface bound PEG chains. As proof-of-principle, we synthesized penta-functional DFO-FITC-EFV-c(RGDyC)-PEG-Cy5-C' dots which combined a total of five types of ligand groups/functionalities on a single particle: NIR fluorescent dyes in the particle core enabling optical particle imaging, peptide ligands allowing specific tumor cell targeting, pH sensing dyes enabling quantitative ratiometric sensing, radio-metal chelators allowing access to positron emission tomography (PET) imaging as well as radiotherapy, and ligand-drug conjugates making the particles theranostic and enabling disease treatment capabilities. All this is achieved while at the same time maintaining nanoparticle properties like ultrasmall particle size below 7 nm, high PEGylation density, good colloidal stability, and control over individual ligand numbers/surface density that should maintain favorable biodistribution and PK characteristics required for particle translation into the clinic. While multiple specific C' dots have already been IND approved by the FDA for human clinical trials, this work opens a gate for further diversification of the clinical applications of C' dots.

Chemicals and reagents. All materials were used as received. Dimethyl sulfoxide (DMSO), isopropanol, (3-mercaptopropyl) trimethoxysilane (MPTMS), (3-aminopropyl) triethoxysilane (APTES), (3-aminopropyl)trimethoxysilane (APTMS), tetramethyl orthosilicate (TMOS), Efavirenz (EFV) and 2.0 M ammonia in ethanol were purchased from Sigma Aldrich. Methoxy-terminated poly(ethylene glycol) chains (PEG-silane, molar mass around 500) were purchased from Gelest. Heterobifunctional PEGs with maleimide and NHS ester groups (mal-PEG-NHS, molar mass around 870) were purchased from Quanta BioDesign. Heterofunctional azide-PEG-thiol (molar mass around 600) was purchased from Nanocs Inc. Cy5 and Cy5.5 florescent dyes were purchased from GE and CW800 florescent dye was purchased from Li-cor. S-2-(4-isothiocyanatobenzyl)-1,4,7,10-tetraazacyclododecantetraacetic acid (DOTA-NCS) and 1-(4-isothiocyanatophenyl)-3-[6,17-dihydroxy-7,10,18,21-tetraoxo-27-(N-acetylhydroxylamino)-6,11,17,22-tetraaza-heptaeicosine] thiourea (DFO-NCS) were purchased from Macrocyclics. Cyclic(arginine-glycine-aspartic acid-D-tyrosine-cysteine) peptides (c(RGDyC)) was purchased from Peptide International. De-ionized water (DI water) was generated using a Millipore Milli-Q system.

Figure 7:
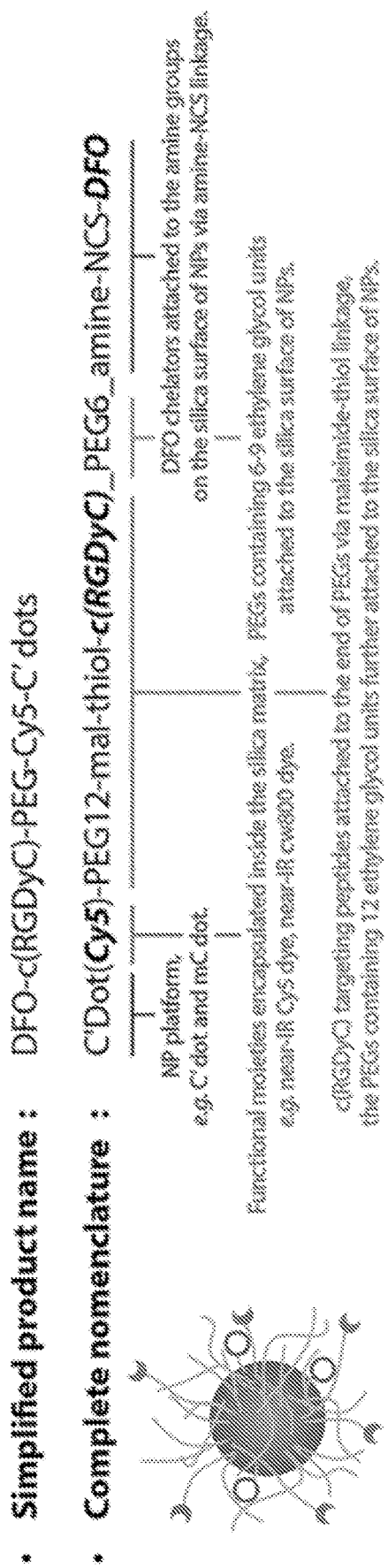
FIG. 7 shows nomenclature of multifunctional C' dots. A tri-functional DFO-c(RGDyC)-PEG-Cy5-C' dot is used as an example whose particle structure illustration is inserted at the bottom-left.

Comprehensive nomenclature to describe different C' dot chemistries. The nomenclature introduced here and used below to differentiate between different C' dot chemistries is illustrated in FIG. 7 (see also Table 1). In detail, the first term from the left, indicates the NP product platform, e.g. water based C' dots or single pore mesoporous silica nanoparticles, mC dots.[34] The specific dye covalently encapsulated into the silica matrix is specified in brackets following the NP platform (e.g. Cy5 in FIG. 7). The content on the right side of the bracket describes the components attached to the NP surface, in sequence of their attachment (since the dots are synthesized first, they appear on the very left, rather than on the right as in the existing, abbreviated nomenclature). In order to highlight the connectivity of functional groups on the particle surface we introduce the following distinctions: a component appearing on the right side of a dash indicates that it is directly attached to the component on the left side of that dash. In contrast, if a component appears on the right side of an underscore, this component is directly attached to the silica NP surface, rather than attached to the previous component on the left side of that underscore. In contrast to the groups used for the conjugation chemistry (e.g. mal-thiol describing conjugation between a maleimide and a thiol group), the components defining the function, e.g. targeting ligands or other fluorescent dyes, are bolded and italicized (see FIG. 7 and Table 1). If a functional group is connected via a PEG chain to the silica NP surface, the number of ethylene glycol monomer units is indicated, e.g. PEG6 or PEG12. As outlined in the introduction, in this way the nanoparticle name carries precise information about: (i) NP platform, (ii) encapsulated fluorescent dye, (iii) specific surface functionality and its connectivity to the particle, (iv) specific conjugation chemistry, (v) synthesis sequence, or (vi) specific PEG chain length.

Synthesis of C'Dot(dye)-PEG12-mal-thiol-c(RGDyC) PEG6 functionalized with different types of NIR dyes. The detailed synthesis of c(RGDyC) functionalized C' dots is described in our previous publication. To encapsulate different types of NIR dyes, the silane functionalized dyes, i.e. Cy5-silane, Cy5.5-silane and CW800-silane were added into the reaction mixture together with TMOS during the first step of C' dot synthesis. The rest of the NP synthesis remained the same as the previously reported protocol for c(RGDyC) functionalized C' dots.

Synthesis of C'Dot(dye)-PEG12-mal-thiol-c(RGDyC) PEG6 with increasing numbers of c(RGDyC) per particle. The concentration of c(RGDyC)-PEG-silane was increased from the original 0.69 mM, which typically results in numbers of c(RGDyC) peptides per C' dot between 16 and 25, to 1.73 mM to further increase the number of c(RGDyC) per NP. To prevent NP aggregation, the reaction concentration of ammonium hydroxide was also increased from 2 mM to 6 mM. This could be achieved by either starting the C' dot synthesis at the ammonium hydroxide concentration of 6 mM, or adding additional ammonium hydroxide right before the PEGylation step to increase the concentration of ammonium hydroxide to 6 mM. Only minor differences of the final C' dot products produced via these two slightly different approaches were observed. Therefore, starting the synthesis with the ammonium concentration of 6 mM is preferred for simplifying the manufacture process.

Synthesis of C'Dot(dye)-PEG12-mal-thiol-c(RGDyC)_PEG12-mal_PEG6, C'Dot(dye)-PEG12-mal-thiol-c(RGDyC)_amine-NCS-DFO_PEG6 and C'Dot(dye)-PEG12-mal-thiol-c(RGDyC)_PEG4-DBCO_PEG6. To introduce additional functional ligands to C'Dot(dye)-PEG12-mal-thiol-c(RGDyC)_PEG6, ligand-silane conjugates were added into the reaction mixture together with c(RGDyC)-PEG-silane and PEG-silane during the PEGylation step. These ligand-silane conjugates included maleimido-functionalized heterobifunctional PEG-silane (mal-PEG-silane), DFO-functionalized silane (DFO-NCS-amine-silane) and DBCO-functionalized heterobifunctional PEG-silane (DBCO-PEG-silane). The concentration of these ligand-silane conjugates ranged from 0.01 mM to 0.34 mM depending on the requirement for surface ligand density. The C'Dot(dye)-PEG12-mal-thiol-c(RGDyC)_PEG12-mal_PEG6 produced via this approach exhibited the desired reactivity with thiol-functionalized ligands. However, the C'Dot(dye)-PEG12-mal-thiol-c(RGDyC)_amine-NCS-DFO_PEG6 and C'Dot(dye)-PEG12-mal-thiol-c(RGDyC)_PEG4-DBCO_PEG6 exhibited undesired property profiles or heterogeneous ligand distributions.

Synthesis of C'Dot(dye)-amine_PEG12-mal-thiol-c(RGDyC) PEG6 and C'Dot(dye)-PEG12-mal-thiol-c(RGDyC) PEG6 amine. To introduce amine groups to C' dots, amino-silane, i.e. APTMS, was introduced into the reaction mixture during different steps of the C' dot synthesis. In one way, APTMS was added into the reaction mixture under vigorous stirring right before the addition of c(RGDyC)-PEG-silane and PEG-silane at a concentration of 1.7 mM, while the rest of the synthesis remained the same. The resulting C'Dot(dye)-amine_PEG12-mal-thiol-c(RGDyC)_PEG6 exhibited a broadened NP size distribution. At the same time, degradation of Cy5 dye was observed. In the post-PEGylation approach, APTMS was added after the PEGylation step. This was done by first reducing the reaction temperature from 80° C. to room temperature at the end of the PEGylation step, followed by the addition of APTMS under vigorous stirring at a concentration of 2.3 mM. The reaction mixture was then left at room temperature under vigorous stirring overnight before purification. The resulting C'Dot(dye)-PEG12-mal-thiol-c(RGDyC)_PEG6_amine exhibited the desired NP size distribution and favorable absorbance characteristics, as indicated by GPC and UV-vis characterizations. In this approach, the C'Dot(dye)-PEG12-mal-thiol-c(RGDyC)_PEG6_amine could be successfully produced with APTMS concentrations as low as 0.3 mM without the NP products losing their reactivity with amine-reactive ligands.

PPSMI based synthesis of C'Dot(dye)-PEG12-mal-thiol-c(RGDyC)_PEG6_amine-NCS-DFO and C'Dot(dye)-PEG12-mal-thiol-c(RGDyC)_PEG6_amine-NCS-DOTA. C'Dot(dye)-PEG12-mal-thiol-c(RGDyC)_PEG6_amine-NCS-DFO and C'Dot(dye)-PEG12-mal-thiol-c(RGDyC)_PEG6_amine-NCS-DOTA were synthesized via adding DFO-NCS or DOTA-NCS, respectively, into the reaction mixture of C'Dot(dye)-PEG12-mal-thiol-c(RGDyC)_PEG6_amine at room temperature under vigorous stirring one day after the addition of amino-silane. The reaction was left under vigorous stirring at room temperature over night before purification. The concentrations of DFO-NCS and DOTA-NCS were varied between roughly 0.02 mM to 0.4 mM to vary the number of DFO or DBCO per NP. Both the concentrations of APTMS and DFO could be varied to control the number of DFO per NP.

PPSMI based synthesis of C'Dot(dye)-PEG6 thiol and C'Dot(dye)-PEG6_thiol-mal-FITC. To introduce thiol groups to PEG-C' dots to generate thiol-functionalized C'Dot(dye)-PEG6 thiol, the synthesis of C'Dot(dye)-PEG12-mal-thiol-c(RGDyC)_PEG6_amine was modified via replacing amine-silane by thiol-silane and using C'Dot(dye)-PEG6 as the base NPs instead of C'Dot(dye)-PEG12-mal-thiol-c(RGDyC)_PEG6. The rest of the NP synthesis remained the same as that of C'Dot(dye)-PEG12-mal-thiol-c(RGDyC)_PEG6_amine. To further attach FITC dyes to C'Dot(dye)-PEG6_thiol to generate C'Dot(dye)-PEG6_thiol-mal-FITC, the synthesis of C'Dot(dye)-PEG12-mal-thiol-c(RGDyC)_PEG6_amine-NCS-DFO was modified via replacing DFO-NCS by FITC-mal and using C'Dot(dye)-PEG6_thiol as the base NPs instead of C'Dot(dye)-PEG12-mal-thiol-c(RGDyC)_PEG6_amine. The rest of the NP synthesis remained the same as that of C'Dot(dye)-PEG12-mal-thiol-c(RGDyC)_PEG6_amine-NCS-DFO.

PPSMI based synthesis of tetra-functional C'Dot(Cy5)-PEG12-mal-thiol-c(RGDyC)_PEG6_amine-NCS-DFO_thiol-mal-FITC. C'Dot(Cy5)-PEG12-mal-thiol-c(RGDyC)_PEG6_amine-NCS-DFO_thiol-mal-FITC was synthesized by first introducing DFO groups to C'Dot(Cy5)-PEG12-mal-thiol-c(RGDyC)_PEG6 via the synthesis approach described for C'Dot(dye)-PEG12-mal-thiol-c(RGDyC)_PEG6_amine-NCS-DFO. Afterwards, thiol groups were added via the synthesis approach to C'Dot(dye)-PEG6_thiol generating C'Dot(Cy5)-PEG12-mal-thiol-c(RGDyC)_PEG6_amine-NCS-DFO_thiol. In the last step, FITC dyes were attached via the synthesis approach to C'Dot(dye)-PEG6_thiol-mal-FITC. The resulting C'Dot(Cy5)-PEG12-mal-thiol-c(RGDyC)_PEG6_amine-NCS-DFO_thiol-mal-FITC was finally purified by GPC and subjected to FCS and optical characterizations. The same C'Dot(Cy5)-PEG12-mal-thiol-c(RGDyC)_PEG6_amine-NCS-DFO_thiol-mal-FITC was also synthesized via an alternative approach in which amine-silane and thiol-silane were added into the reaction mixture together, instead of by sequential addition. The reaction was then left at room temperature under vigorous stirring for four hours, followed by the simultaneous addition of DFO-NCS and FITC-mal. The rest of the reaction remained the same.

Synthesis of C'Dot(Cy5)-PEG12-mal-thiol-c(RGDyC)_PEG12-mal-thiol-PEG10-EVF_PEG6_amine-NC S-DFO_thiol-mal-FITC. C'Dot(Cy5)-PEG12-mal-thiol-c(RGDyC)_PEG12-mal-thiol-PEG10-EVF_PEG6_amine-NCS-DFO_thiol-mal-FITC was synthesized by first conjugating EFV with azide-PEG-thiol through azide-alkyne click chemistry in DMSO at molar ratio 4 EFV: 1 azide-PEG-thiol with EFV concentration around 0.021 M. The reaction mixture was left under nitrogen for 6 days to achieve the desired conjugation yield. The resulting thiol-functionalized EFV was then added into the reaction mixture of C'Dot(Cy5)-PEG12-mal-thiol-c(RGDyC)_PEG12-mal_PEG6 at concentration 1.15 mM right after the PEGylation step, i.e. after the 80° C. heat treatment step. The reaction mixture was then left under vigorous stirring at room temperature for another 6 days to attach thiol-functionalized EFV to the maleimide groups on C'Dot(Cy5)-PEG12-mal-thiol-c(RGDyC)_PEG12-mal_PEG6, generating C'Dot(Cy5)-PEG12-mal-thiol-c(RGDyC)_PEG12-mal-thiol-PEG10-EVF_PEG6. Afterwards, DFO and FITC were introduced following the same procedure described above for C'Dot(Cy5)-PEG12-mal-thiol-c(RGDyC)_PEG6_amine-NCS-DFO_thiol-mal-FITC.

GPC characterization and purification of c(RGDyC)-PEG-C' dots. The detailed GPC characterization and purification steps of C' dots are described in our previous publications.

UV-vis and FCS measurements. Absorbance spectra of samples were measured on a Varian Cary 5000 spectrophotometer. FCS measurements were conducted using a home-built FCS/FCCS set-up as previously described. A 635 nm solid-state laser was used to excite the Cy5 and Cy5.5 dots, while a 785 nm solid-state laser was used to excite the cw800 dots.

Comprehensive nomenclature to describe different C' dot chemistries. The nomenclature introduced here and used below to differentiate between different C' dot chemistries is illustrated in FIG. 7 (see also Table 1). In detail, the first term from the left, indicates the NP product platform, e.g. water based C' dots or single pore mesoporous silica nanoparticles, mC dots. The specific dye covalently encapsulated into the silica matrix is specified in brackets following the NP platform (e.g. Cy5 in FIG. 7). The content on the right side of the bracket describes the components attached to the NP surface, in sequence of their attachment (since the dots are synthesized first, they appear on the very left, rather than on the right as in our existing nomenclature). In order to highlight the connectivity of functional groups on the particle surface we introduce the following distinctions: a component appearing on the right side of a dash indicates that it is directly attached to the component on the left side of that dash. In contrast, if a component appears on the right side of an underscore, this component is directly attached to the silica NP surface, rather than attached to the previous component on the left side of that underscore. In contrast to the groups used for the conjugation chemistry (e.g. mal-thiol describing conjugation between a maleimide and a thiol group), the components defining the function, e.g. targeting ligands or other fluorescent dyes, are bolded and italicized (see FIG. 7 and Table 1). If a functional group is connected via a PEG chain to the silica NP surface, the number of ethylene glycol monomer units is indicated, e.g. PEG6 or PEG12. As outlined in the introduction, in this way the nanoparticle name carries precise information about: (i) NP platform, (ii) encapsulated fluorescent dye, (iii) specific surface functionality and its connectivity to the particle, (iv) specific conjugation chemistry, (v) synthesis sequence, or (vi) specific PEG chain length.

Example 2

This example provides examples of methods and compositions of the present disclosure and uses of same.

Figure 18:
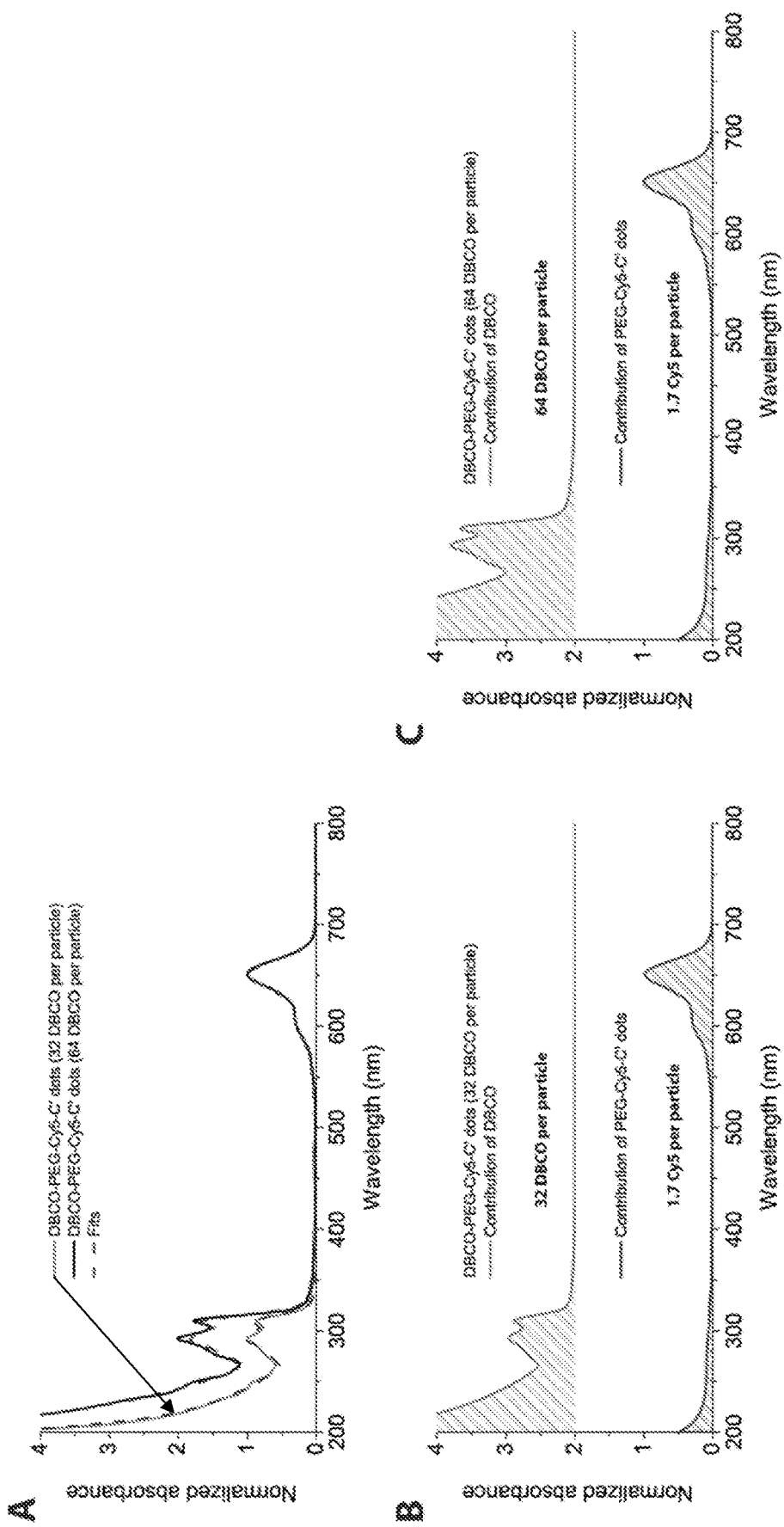
FIG. 18 shows characterization of DBCO-PEG-Cy5-C' dots. (A) Comparison of UV-Vis absorbance spectra with deconvolution fits of DBCO-PEG-Cy5-C' dots with different DBCO ligand numbers. (B to G) UV-Vis absorbance deconvolution (B and C), GPC elugram with fits (D and E), and FCS correlation curves with fits (F and G) of DBCO-PEG-Cy5-C' dots with 32 (B, D, and F) and 64 (C, E and G) DBCO groups per particle, respectively.
Figure 18:
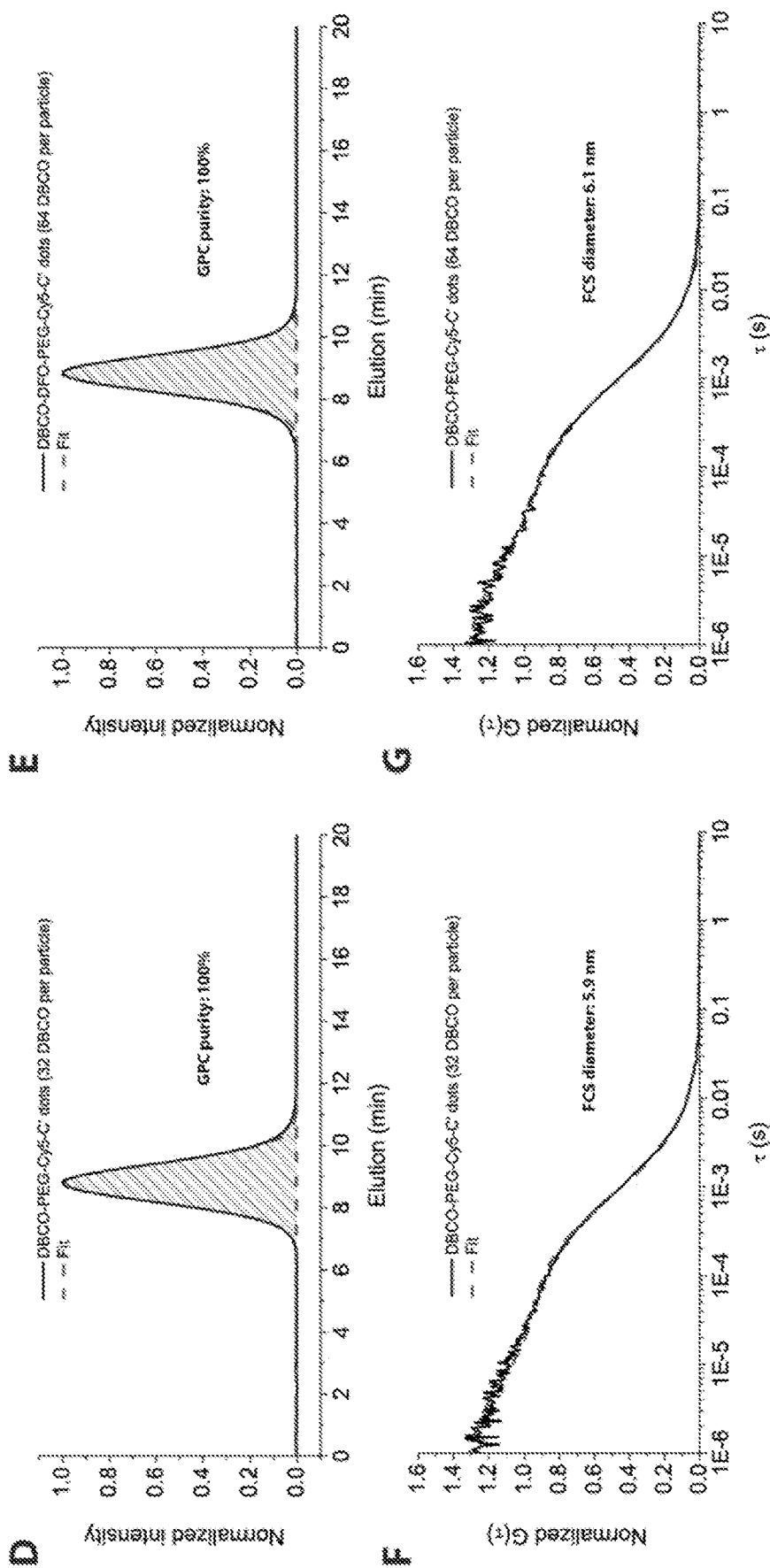

Described is an example of functional C' dots synthesized via PPSMI approach, i.e. DBCO-PEG-Cy5-C' dots, is described (FIG. 18). The DBCO-PEG-Cy5-C' dots contain DBCO reactive groups between the PEG chains on C' dot surface. The DBCO groups can further react with azide-conjugated functional ligands via click chemistry to introduce additional functional groups to C' dots. To produce DBCO-PEG-Cy5-C' dots, silane-conjugated Cy5 fluorescent dye was first covalently encapsulated in the silica nanoparticles during the formation of C' dot silica cores. PEG-silane was then covalently attached to the surface of the silica nanoparticles, forming PEGylated PEG-Cy5-C' dots. After the PEGylation step, amine-silane was added into the reaction mixture to covalently attach to the remaining silanol groups under the PEG layer of C' dots via silane condensation, introducing reactive amine groups. DBCO-PEG4-NHS ester was then added to further react with the amine groups under the PEG layer of C' dots via amine-NETS ester conjugation reaction. Different concentrations of DBCO-PEG4-NHS ester were used to vary the DBCO ligand numbers of DBCO-PEG-Cy5-C' dots.

Example 3

This example provides examples of methods and compositions of the present disclosure and uses of same.

Figure 19:
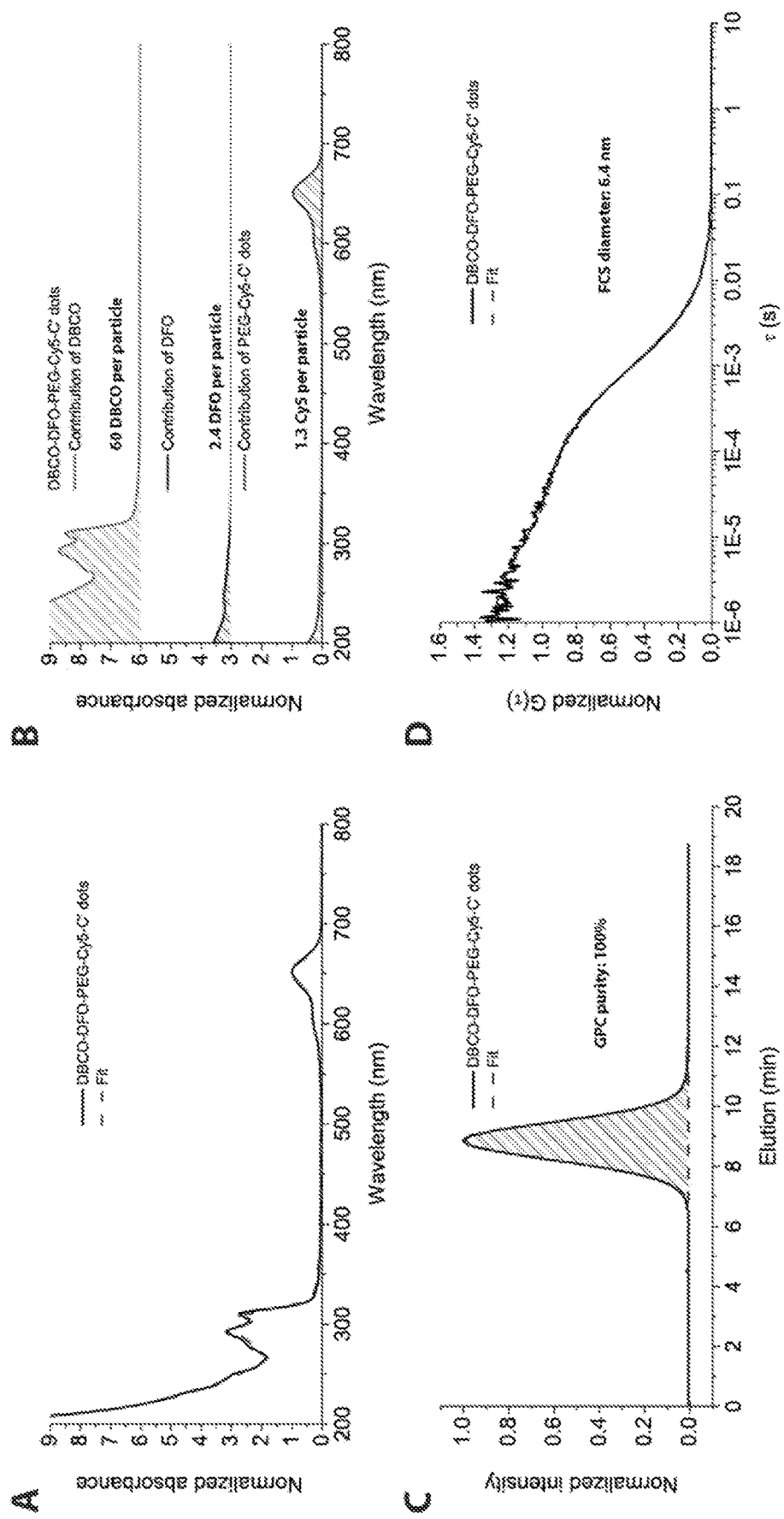
FIG. 19 shows characterization of DBCO-DFO-PEG-Cy5-C' dots. (A) UV-Vis absorbance spectra with deconvolution fit. (B) UV-Vis absorbance deconvolution. (C) GPC elugram with fit. (D) FCS correlation curve with fit.

Described is an example of functional C' dots synthesized via PPSMI approach, i.e. DBCO-DFO-PEG-Cy5-C' dots, is described (FIG. 19). The DBCO-DFO-PEG-Cy5-C' dots contain both DBCO reactive groups and DFO chelator groups between the PEG chains on C' dot surface. While the DBCO groups can further react with azide-conjugated functional ligands via click chemistry to introduce additional functional groups to C' dots, the DFO groups can chelate radio-metals to enable C' dots to be used as positron emission tomography (PET) probes. To produce DBCO-DFO-PEG-Cy5-C' dots, silane-conjugated Cy5 fluorescent dye was first covalently encapsulated in the silica nanoparticle during the formation of C' dot silica cores. PEG-silane was then covalently attached to the surface of the silica nanoparticles, forming PEGylated PEG-Cy5-C' dots. After the PEGylation step, amine-silane was added into the reaction mixture to covalently attach to the remaining silanol groups under the PEG layer of C' dots via silane condensation, introducing reactive amine groups. SCN-functioned DFO (DFO-SCN) was then added into the reaction mixture to react with the amine groups under the PEG layer of C' dots via amine-SCN conjugation reaction. A low concentration of DFO-SCN was used to introduce only less than 5 DFO chelators to each C' dot. Thus, the remaining amine groups on C' dot surface can be used for DBCO attachment as described above. One day after the addition of DFO-SCN, DBCO-PEG4-NHS ester was then added into the reaction mixture to further react with the remaining amine groups under the PEG layer of C' dots via amine-NETS ester conjugation reaction. As a result, both DFO and DBCO were covalently attached to C' dot surface between the PEG chains via PPSMI method.

Example 4

This example provides a summary of reaction conditions of the present disclosure.

The synthesis system can be extended to at least nine orthogonal and modular functionalization pathways to selectively combine different functional groups onto a single nanoparticle platform. The nanoparticle platforms to which these functionalization approaches are applicable include, but are not limited to, C' dot, AlC' dots and mC dots. ([1] in Table 2)

In addition to Cy5, Cy5.5 and cw800, other types of dyes can be functionalized with silane groups via conjugation chemistries including, but not limited to, thiol-ene, amine-NHS ester, azide-alkyne chemistries. The dye-silane conjugates can then be added during the core formation step to endow nanoparticles with different fluorescence properties. The different types of dyes include, but are not limited to, DACM, DEAC, RHG, TMR, TRITC, FITC, Cy3, ATTO647N, ATTO680 and DY782. ([2] in Table 2)

In addition to c(RGDyC) cancer targeting peptides, other ligands that perform specific application functions can be attached to heterobifunctional PEG-silane via conjugation chemistries including, but not limited to, thiol-ene, amine-NETS este, azide-alkyne chemistries. The resulting ligand-PEG-silane conjugates can then be added during the PEGylation step to endow nanoparticles with different functions. The different functional ligands include, but are not limited to, peptides, antibody fragments, DNA molecules, RNA molecules, fluorescent dyes, sensing molecules, drug molecules and chelator molecules. ([3] in Table 2)

In addition to maleimide functionalized heterobifunctional PEG-silane, other heterobifunctional PEG-silanes containing a reactive group can be attached to nanoparticle surfaces during the PEGylation step, allowing for further modifying the nanoparticles with additional functional ligands at the PEG chain ends. The reactive groups include, but are not limited to, maleimide groups, NHS ester groups, azide groups, amine groups, thiol groups, alkyne groups and DBCO groups. ([4] in Table 2)

In addition to EFV-PEG-SH, after PEGylation, other ligands that perform specific application functions can be attached to the reactive groups that are already present at the PEG chain ends on nanoparticle surfaces, via conjugation chemistries including, but not limited to, thiol-ene reaction, amine-NETS ester reaction, or azide-alkyne reaction. The different functional ligands include, but are not limited to, peptides, antibody fragments, DNA molecules, RNA molecules, fluorescent dyes, sensing molecules, drug molecules, and chelator molecules. ([5] in Table 2)

In addition to thiol-silane and amino-silane, other silane conjugates containing a reactive group can be inserted into the PEG layer after PEGylation and attached to the silica surface underneath, allowing for further modifying the nanoparticles with additional functional ligands between the PEG chains. The reactive groups include but are not limited to, maleimide groups, NHS ester groups, azide groups, amine groups, thiol groups, alkyne groups and DBCO groups. ([6] in Table 2)

In addition to DFO, DOTA and FITC, after PEGylation, other ligands that perform specific application functions can be attached to the reactive groups that are already inserted into the PEG layer. The different functional ligands include, but are not limited to, peptides, antibody fragments, DNA molecules, RNA molecules, fluorescent dyes, sensing molecules, and chelator molecules. ([7] in Table 2)

Other silane conjugates containing a small ligand that performs specific application functions can be inserted into the PEG layer after PEGylation and attached to the silica surface underneath. The different functional ligands include, but are not limited to, peptides, antibody fragments, DNA molecules, RNA molecules, fluorescent dyes, sensing molecules and chelator molecules. ([8] in Table 2)

TABLE 2

Summary of reaction conditions used in each orthogonal functionalization pathway.

| Synthesis steps | Orthogonal pathways[1] | Functionalities | 1st ligand Type | Concentration | 2nd ligand (if applicable) Type | Concentration | # of ligand per particle |
|---|---|---|---|---|---|---|---|
| Core formation | 1st | Fluorescence dye | Cy5-silane<br>Cy5.5-silane<br>Cw800-silane<br>Other dye-silane conjugates[2] | 0-0.6 mM<br>0-0.6 mM<br>0-0.6 mM<br>0-0.6 mM | | | 0-4 Cy5<br>0-4Cy5.5<br>0-4 cw800<br>0-4 dyes |
| PEGylation | 2nd | Cancer targeting | c(RGDyC)-PEG-silane | 0-2.1 mM | | | 0-70 c(RGDyC) peptides |
| | 3rd | Other functionalities including, but not limited to, optical tracing, disease targeting, radioisotopes chelating, sensing and therapeutics | Other functional ligands attached to heterobifunctional PEG- silane[3] | 0-2.1 mM | | | 0-70 functional ligands |
| | 4th | Enabling further modifications with functional ligands | mal-PEG-silane | 0-2.1 mM | | | 0-70 mal groups |
| | | Therapeutics | mal-PEG-silane | 0-2.1 mM | EFV-PEG-SH | 0-6 mM | 0-50 EFV drugs |
| | | Other functionalities including, but not limited to, optical tracing, disease targeting, radioisotopes chelating, sensing and therapeutics | mal-PEG-silane | 0-2.1 mM | Other functional ligands that can attach to maleimide groups[5] | 0-6 mM | 0-50 unctional ligands |
| | 5th | Enabling further modifications with functional ligands | Other reactive groups attached to heterobifunctional PEG- silane[4] | 0-2.1 mM | | | 0-70 reactive groups |
| | | Other functionalities including, but not limited to, optical tracing, disease targeting, radioisotopes chelating, sensing and therapeutics | Other reactive groups attached to heterobifunctional PEG- silane[4] | 0-2.1 mM | Other functional ligands that can attach to the earlier introduced reactive groups[5] | 0-6 mM | 0-50 functional ligands |
| Post-PEGylation surface modification | 6th | Enabling further modifications with functional ligands | amine-silane | 0-2.3 mM | | | 0-40 amine groups |
| | | Radioisotope chelating | amine-silane | 0-2.3 mM | DFO-NCS | 0-1.3 mM | 0-40 DFO chelators |

TABLE 2-continued

Summary of reaction conditions used in each orthogonal functionalization pathway.

| Synthesis steps | Orthogonal pathways[1] | Functionalities | 1st ligand Type | 1st ligand Concentration | 2nd ligand (if applicable) Type | 2nd ligand Concentration | # of ligand per particle |
|---|---|---|---|---|---|---|---|
| | | Radioisotope chelating | amine-silane | 0-2.3 mM | DOTA-NCS | 0-1.3 mM | 0-40 DOTA chelators |
| | | Other functionalities including, but not limited to, optical tracing, disease targeting, radioisotopes chelating, sensing and therapeutics | amine-silane | 0-2.3 mM | Other functional ligands that can attach to amine groups | 0-1.3 mM | 0-40 reactive groups |
| | 7th | Enabling further modifications with functional ligands | thiol-silane | 0-2.3 mM | | | |
| | | Sensing | thiol-silane | 0-2.3 mM | FITC-NCS | 0-1.3 mM | 0-20 FITC dyes |
| | | Other functionalities including, but not limited to, optical tracing, disease targeting, radioisotopes chelating, sensing and therapeutics | thiol-silane | 0-2.3 mM | Other functional ligands that can to thiol groups[7] | 0-1.3 mM | 0-40 functional ligands |
| | 8th | Enabling further modifications with functional ligands | Other reactive groups attached to silane[6] | 0-2.3 mM | | | 0-40 reactive groups |
| | | Other functionalities including, but not limited to, optical tracing, disease targeting, radioisotopes chelating, sensing and therapeutics | Other reactive groups attached to silane[6] | 0-2.3 mM | Other functional ligands that can attach to the earlier introduced reactive groups[7] | 0-1.3 mM | 0-40 functional ligands |
| | 9th | Other functionalities including, but not limited to, optical tracing, disease targeting, radioisotopes chelating, sensing and therapeutics | Other functional ligands attached to silane[8] | 0-2.3 mM | | | 0-40 functional ligands |

The invention claimed is:

1. A method of forming a functionalized PEGylated silica nanoparticle comprising:

functionalizing a silica nanoparticle using a post PEGylation surface modification by insertion (PPSMI) step, wherein the nanoparticle has a diameter of 2 to 15 nm and comprises a plurality of polyethylene glycol (PEG) groups covalently bound to the surface of the nanoparticle, wherein the PPSMI step comprises inserting a functionalizing precursor between PEG groups on the nanoparticle and covalently binding the precursor to the surface of the nanoparticle, wherein the functionalizing precursor comprises a silane group and a reactive group, and wherein the PPSMI step is carried out in an aqueous reaction medium, thereby forming a functionalized PEGylated silica nanoparticle comprising a reactive group covalently bound to the surface of the nanoparticle.

2. The method of claim 1, further comprising inserting one more additional functionalizing precursors between PEG groups on the nanoparticle and covalently binding the one or more additional precursors to the surface of the nanoparticle, wherein the one or more additional precursors each comprise a silane group and a reactive group.

3. The method of claim 2, wherein each additional functionalizing precursor is inserted in the same reaction mixture.

4. The method of claim 2, wherein the inserting for an additional functionalizing precursor is carried out in a separate reaction mixture.

5. The method of claim 1, wherein the reactive group is chosen from an amine group, a thiol group, a carboxylic acid group, a carboxylate group, an ester group, a maleimide group, an allyl group, a terminal alkyne group, an azide group, a thiocyanate group, and combinations thereof.

6. The method of claim 1, wherein the silane group is:

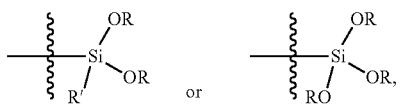

wherein R is, independently at each occurrence, a $C_1$ to $C_4$ alkyl group, and
R' is H or a $C_1$ to $C_4$ alkyl group.

7. The method of claim 1, wherein the functionalizing precursor has the following structure:

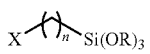

wherein X is a an amine group, a thiol group, a carboxylic acid group, a carboxylate group, an ester group, a maleimide group, an allyl group, a terminal alkyne group, an azide group, or a thiocyanate group,
n is 1 to 8, and
R is, independently at each occurrence, a $C_1$ to $C_4$ alkyl group.

8. The method of claim 1, wherein the nanoparticle is a core-shell silica nanoparticle.

9. The method of claim 1, wherein the nanoparticle has a diameter of 2 to 10 nm.

10. The method of claim 1, further comprising a step of reacting the reactive group covalently bound to the surface of the nanoparticle with a functional group precursor.

11. The method of claim 10, wherein the functional group precursor comprises a dye, a chelator, a targeting group, or a drug.

12. The method of claim 11, wherein the drug comprises a chemotherapeutic agent.

13. The method of claim 11, wherein the targeting group has a specific binding affinity to tumor cells.

14. The method of claim 11, wherein the targeting group comprises a linear or cyclic peptide, or an antibody fragment.

15. The method of claim 10, wherein the functional group precursor comprises a maleimide group, an NHS ester group, an azide group, an amine group, a thiol group, or an alkyne group.

16. The method of claim 1, wherein the aqueous reaction medium does not contain organic solvents other than polar aprotic solvents at 10% or greater.

17. The method of claim 1, wherein the nanoparticle comprises one or more fluorescent dye molecules encapsulated therein.

18. The method of claim 17, wherein the fluorescent dye molecule is Cy5 or Cy5.5.

19. The method of claim 10, wherein the reacting comprises click chemistry.

* * * * *